(12) United States Patent
Chung et al.

(10) Patent No.: US 11,576,772 B2
(45) Date of Patent: Feb. 14, 2023

(54) ONE-PIECE HEART VALVE STENTS ADAPTED FOR POST-IMPLANT EXPANSION

(71) Applicant: Edwards Lifesciences Corporation, Irvine, CA (US)

(72) Inventors: Visith Chung, Chino, CA (US); Da-Yu Chang, Irvine, CA (US); Brian S. Conklin, Orange, CA (US); Grace Myong Kim, Seal Beach, CA (US); Louis A. Campbell, Santa Ana, CA (US); Donald E. Bobo, Jr., Santa Ana, CA (US); Myron Howanec, Jr., Corona, CA (US); David S. Lin, Irvine, CA (US); Peng Norasing, Corona, CA (US); Francis M. Tran, Irvine, CA (US); Mark Van Nest, Rancho Santa Margarita, CA (US); Thomas Chien, Irvine, CA (US); Harvey H. Chen, Irvine, CA (US); Isidro L. Guerrero, Orange, CA (US); Derrick Johnson, Orange, CA (US); Paul A. Schmidt, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 481 days.

(21) Appl. No.: 16/773,802

(22) Filed: Jan. 27, 2020

(65) Prior Publication Data
US 2020/0155309 A1    May 21, 2020

Related U.S. Application Data

(63) Continuation of application No. 16/007,879, filed on Jun. 13, 2018, now Pat. No. 10,543,085, which is a
(Continued)

(51) Int. Cl.
*A61F 2/24*       (2006.01)

(52) U.S. Cl.
CPC .......... *A61F 2/2418* (2013.01); *A61F 2/2409* (2013.01); *A61F 2/2445* (2013.01);
(Continued)

(58) Field of Classification Search
CPC .... A61F 2/2418; A61F 2/2409; A61F 2/2445; A61F 2/2433; A61F 2210/0004;
(Continued)

(56) References Cited

U.S. PATENT DOCUMENTS

| 3,656,185 A | 4/1972 | Carpentier |
| 4,055,861 A | 11/1977 | Carpentier et al. |

(Continued)

FOREIGN PATENT DOCUMENTS

| EP | 0338994 A1 | 10/1989 |
| EP | 1034753 A1 | 9/2000 |

(Continued)

*Primary Examiner* — William H Matthews
(74) *Attorney, Agent, or Firm* — Guy Cumberbatch

(57) ABSTRACT

A prosthetic heart valve configured to replace a native heart valve and having a support frame configured to be reshaped into an expanded form in order to receive and/or support an expandable prosthetic heart valve therein is disclosed, together with methods of using same. The prosthetic heart valve may be configured to have a generally rigid and/or expansion-resistant configuration when initially implanted to replace a native valve (or other prosthetic heart valve), but to assume a generally expanded form when subjected to an outward force such as that provided by a dilation balloon or other mechanical expander.

20 Claims, 27 Drawing Sheets

Related U.S. Application Data continuation-in-part of application No. 15/624,427, filed on Jun. 15, 2017, now Pat. No. 10,485,661, which is a continuation of application No. 15/190,094, filed on Jun. 22, 2016, now Pat. No. 10,052,200, which is a continuation of application No. 14/136,318, filed on Dec. 20, 2013, now Pat. No. 9,375,310.

(60) Provisional application No. 61/748,022, filed on Dec. 31, 2012.

(52) U.S. Cl.
CPC ..... *A61F 2/2433* (2013.01); *A61F 2210/0004* (2013.01); *A61F 2220/0033* (2013.01); *A61F 2220/0075* (2013.01); *A61F 2230/0054* (2013.01); *A61F 2250/001* (2013.01); *A61F 2250/0004* (2013.01); *A61F 2250/006* (2013.01); *A61F 2250/0063* (2013.01); *A61F 2250/0071* (2013.01); *A61F 2310/00011* (2013.01)

(58) Field of Classification Search
CPC ...... A61F 2220/0033; A61F 2220/0075; A61F 2250/0004; A61F 2250/001; A61F 2250/006; A61F 2250/0063; A61F 2250/0071; A61F 2310/00011
See application file for complete search history.

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,602,911 A | 7/1986 | Ahmadi et al. |
| 4,759,759 A * | 7/1988 | Walker ............... A61F 2/2412 623/2.16 |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,147,391 A | 9/1992 | Lane |
| 5,201,880 A | 4/1993 | Wright et al. |
| 5,258,021 A | 11/1993 | Duran |
| 5,306,296 A | 4/1994 | Wright et al. |
| 5,450,860 A | 9/1995 | O'Connor |
| 5,496,336 A | 3/1996 | Cosgrove et al. |
| 5,593,435 A | 1/1997 | Carpentier et al. |
| 5,607,471 A | 3/1997 | Seguin et al. |
| 5,674,279 A | 10/1997 | Wright et al. |
| 5,697,382 A | 12/1997 | Love et al. |
| 5,716,417 A | 2/1998 | Girard et al. |
| 5,776,189 A | 7/1998 | Khalid |
| 5,824,066 A | 10/1998 | Gross |
| 5,888,240 A | 3/1999 | Carpentier et al. |
| 5,972,030 A | 10/1999 | Garrison et al. |
| 5,984,973 A * | 11/1999 | Girard ............... A61F 2/2418 623/2.38 |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 * | 2/2001 | Wright ............... A61F 2/2448 623/2.36 |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,332,893 B1 | 12/2001 | Mortier et al. |
| 6,348,068 B1 | 2/2002 | Campbell |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,425,916 B1 | 7/2002 | Garrison et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,261,732 B2 | 8/2007 | Justino |
| 7,276,084 B2 | 10/2007 | Yang et al. |
| 7,294,148 B2 | 11/2007 | McCarthy |
| 7,381,218 B2 | 6/2008 | Schreck |
| 7,393,360 B2 | 7/2008 | Spenser et al. |
| 7,399,315 B2 | 7/2008 | Iobbi |
| 7,452,376 B2 | 11/2008 | Lim et al. |
| 7,462,191 B2 | 12/2008 | Spenser et al. |
| 7,470,285 B2 | 12/2008 | Nugent et al. |
| 7,510,575 B2 | 3/2009 | Spenser et al. |
| 7,524,330 B2 | 4/2009 | Berreklouw |
| 7,534,261 B2 | 5/2009 | Friedman |
| 7,556,646 B2 | 7/2009 | Yang et al. |
| 7,585,321 B2 | 9/2009 | Cribier |
| 7,625,403 B2 | 12/2009 | Krivoruchko |
| 7,758,640 B2 | 7/2010 | Vesely |
| 7,780,723 B2 | 8/2010 | Taylor |
| 7,806,927 B2 | 10/2010 | Styrc |
| 7,871,436 B2 | 1/2011 | Ryan et al. |
| 8,025,695 B2 | 9/2011 | Fogarty et al. |
| 8,034,104 B2 | 10/2011 | Carpentier et al. |
| 8,226,707 B2 | 7/2012 | White |
| 8,236,045 B2 | 8/2012 | Benichou et al. |
| 8,246,677 B2 | 8/2012 | Ryan |
| 8,246,762 B2 | 8/2012 | Janko et al. |
| 8,496,700 B2 | 7/2013 | Edoga et al. |
| 8,500,802 B2 | 8/2013 | Lane et al. |
| 8,888,836 B2 | 11/2014 | Berglund |
| 2001/0021874 A1 | 9/2001 | Carpentier et al. |
| 2002/0062150 A1 | 5/2002 | Campbell et al. |
| 2003/0033009 A1 | 2/2003 | Gabbay |
| 2003/0040793 A1 | 2/2003 | Marquez |
| 2003/0199971 A1 | 10/2003 | Tower et al. |
| 2004/0122514 A1 | 6/2004 | Fogarty et al. |
| 2004/0210305 A1 | 10/2004 | Shu et al. |
| 2004/0249452 A1 | 12/2004 | Adams et al. |
| 2004/0249453 A1 | 12/2004 | Cartledge et al. |
| 2005/0010283 A1 * | 1/2005 | Vijay ............... A61F 2/2448 623/2.11 |
| 2005/0096739 A1 | 5/2005 | Cao |
| 2005/0131533 A1 | 6/2005 | Alfieri et al. |
| 2005/0240200 A1 | 10/2005 | Bergheim |
| 2005/0251251 A1 | 11/2005 | Cribier |
| 2005/0256567 A1 | 11/2005 | Lim et al. |
| 2005/0256568 A1 | 11/2005 | Lim et al. |
| 2005/0267572 A1 | 12/2005 | Schoon et al. |
| 2005/0278022 A1 | 12/2005 | Lim |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025858 A1 | 2/2006 | Alameddine |
| 2006/0030885 A1 | 2/2006 | Hyde |
| 2006/0052867 A1 | 3/2006 | Revuelta et al. |
| 2006/0241748 A1 | 10/2006 | Lee et al. |

(56) References Cited

U.S. PATENT DOCUMENTS

| | | |
|---|---|---|
| 2007/0016287 A1 | 1/2007 | Cartledge et al. |
| 2007/0067029 A1 | 3/2007 | Gabbay |
| 2007/0100441 A1 | 5/2007 | Kron et al. |
| 2007/0142907 A1 | 6/2007 | Moaddeb et al. |
| 2007/0162111 A1 | 7/2007 | Fukamachi et al. |
| 2007/0244546 A1 | 10/2007 | Francis |
| 2008/0027483 A1 | 1/2008 | Cartledge et al. |
| 2008/0097575 A1 | 4/2008 | Cottone |
| 2008/0114452 A1 | 5/2008 | Gabbay |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0183285 A1 | 7/2008 | Shaoulian et al. |
| 2008/0200980 A1 | 8/2008 | Robin et al. |
| 2008/0208327 A1 | 8/2008 | Rowe |
| 2008/0208329 A1 | 8/2008 | Bishop et al. |
| 2008/0215144 A1 | 9/2008 | Ryan et al. |
| 2008/0228263 A1 | 9/2008 | Ryan |
| 2008/0243246 A1 | 10/2008 | Ryan et al. |
| 2008/0269878 A1 | 10/2008 | Iobbi |
| 2008/0275549 A1 | 11/2008 | Rowe |
| 2009/0005863 A1 | 1/2009 | Goetz et al. |
| 2009/0082857 A1 | 3/2009 | Lashinski et al. |
| 2009/0093876 A1 | 4/2009 | Nitzan et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192606 A1 | 7/2009 | Gloss et al. |
| 2009/0216322 A1 | 8/2009 | Le et al. |
| 2009/0264989 A1 | 10/2009 | Bonhoeffer et al. |
| 2009/0281609 A1 | 11/2009 | Benichou et al. |
| 2010/0076548 A1* | 3/2010 | Konno ............ A61F 2/2412 623/2.11 |
| 2010/0076549 A1 | 3/2010 | Keidar et al. |
| 2011/0137409 A1 | 6/2011 | Yang et al. |
| 2011/0137410 A1 | 6/2011 | Hacohen |
| 2011/0166636 A1 | 7/2011 | Rowe |
| 2011/0178597 A9 | 7/2011 | Navia et al. |
| 2011/0224781 A1 | 9/2011 | White |
| 2011/0230956 A1 | 9/2011 | White |
| 2011/0245918 A1 | 10/2011 | White |
| 2011/0264207 A1 | 10/2011 | Bonhoeffer et al. |
| 2011/0288629 A1 | 11/2011 | White |
| 2011/0288632 A1 | 11/2011 | White |
| 2012/0277854 A1 | 11/2012 | Ryan |
| 2012/0283820 A1 | 11/2012 | Tseng et al. |
| 2012/0303113 A1 | 11/2012 | Benichou et al. |

FOREIGN PATENT DOCUMENTS

| | | | |
|---|---|---|---|
| EP | 1755459 A2 | 2/2007 | |
| EP | 1804726 A1 | 7/2007 | |
| EP | 1958598 A1 | 8/2008 | |
| EP | 2094194 B1 | 9/2015 | |
| WO | 0041649 A1 | 7/2000 | |
| WO | 2004006810 A1 | 1/2004 | |
| WO | 2012018779 A2 | 2/2012 | |
| WO | WO-2012018779 A2 * | 2/2012 | ........... A61F 2/2418 |

* cited by examiner

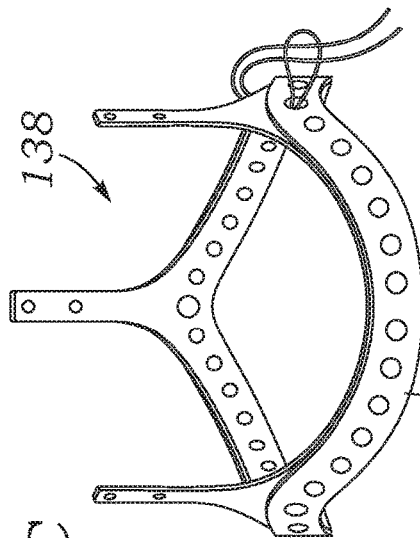
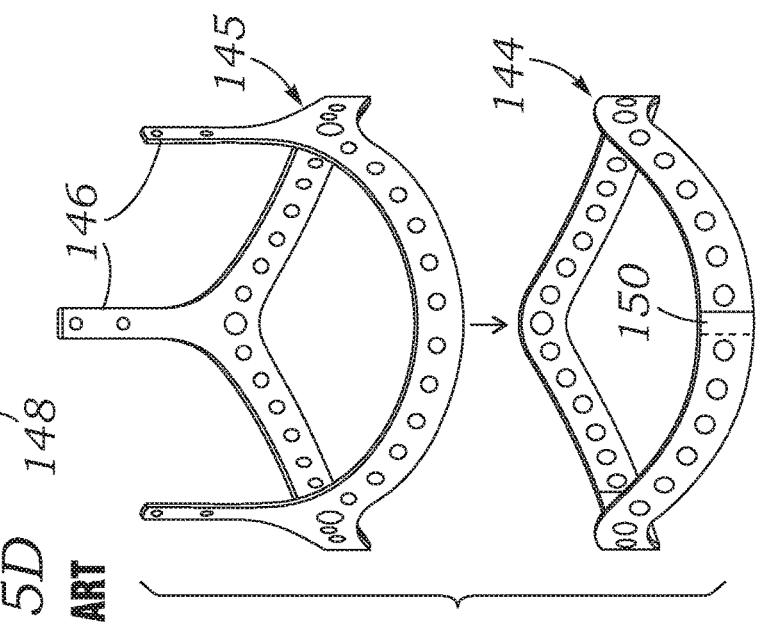
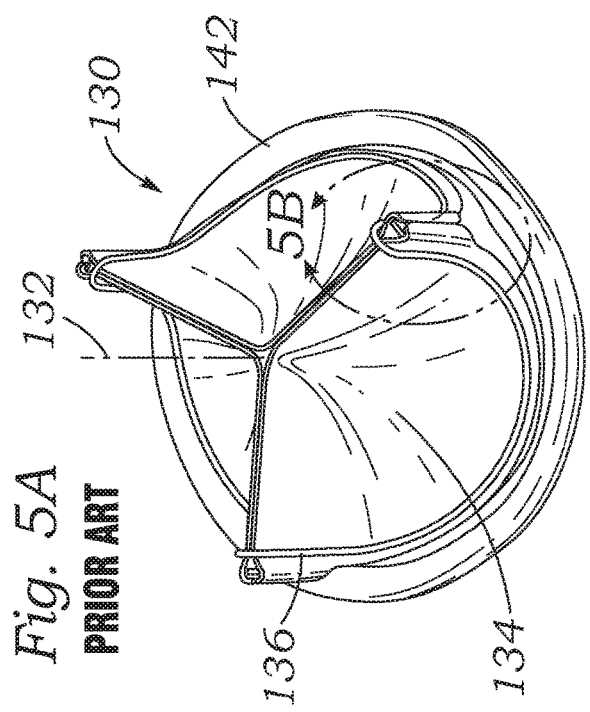
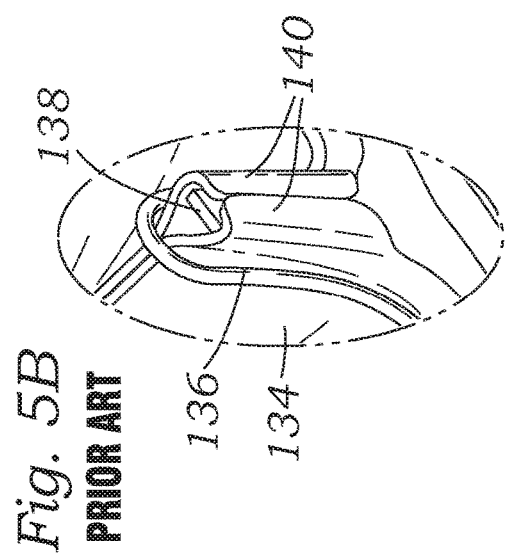
Fig. 5A PRIOR ART
Fig. 5B PRIOR ART
Fig. 5C PRIOR ART
Fig. 5D PRIOR ART

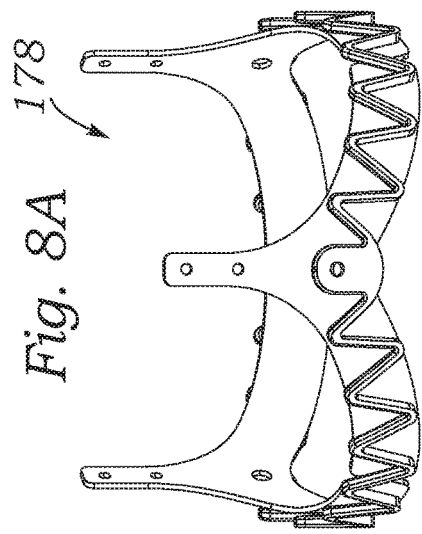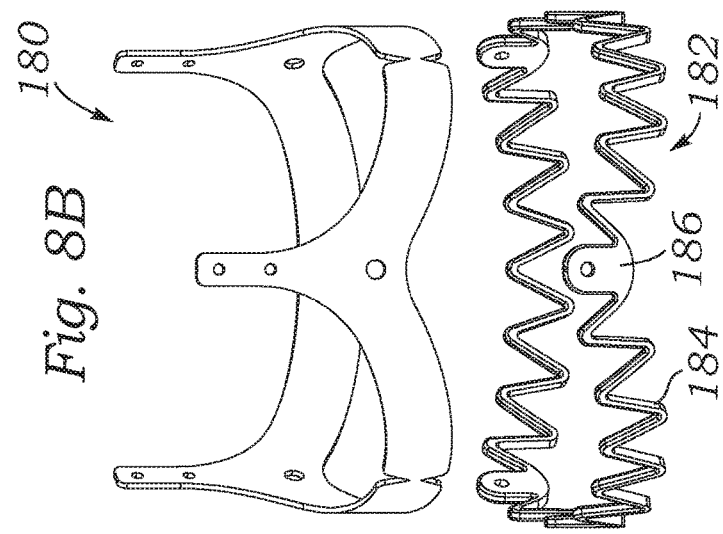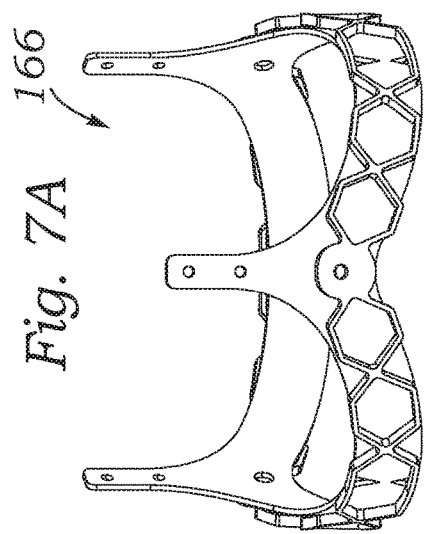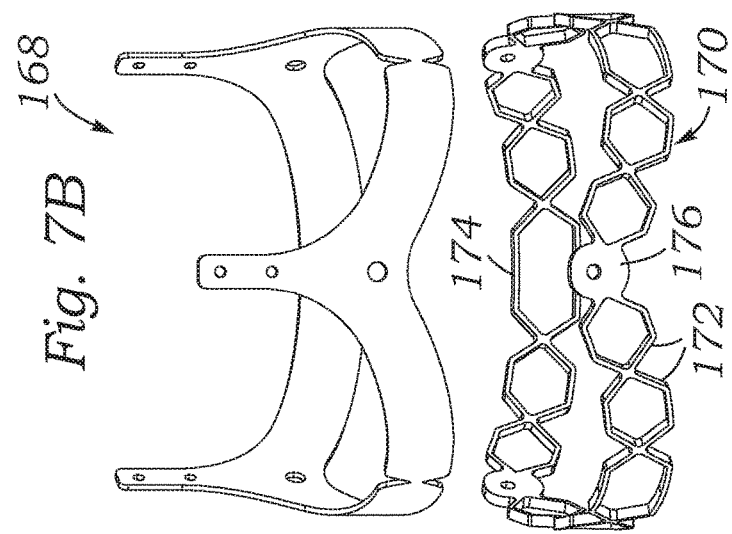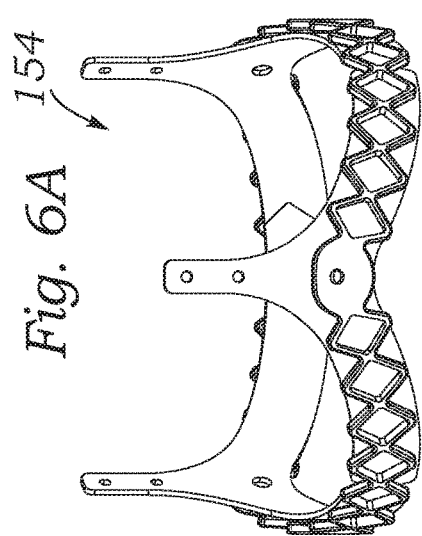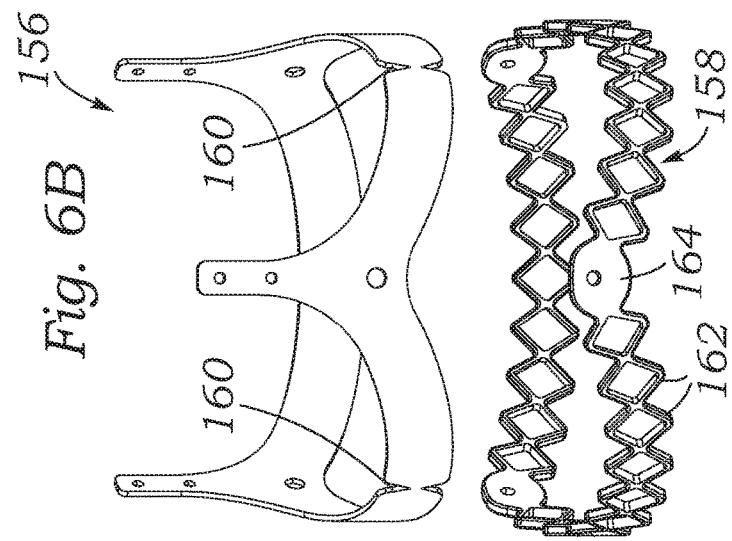

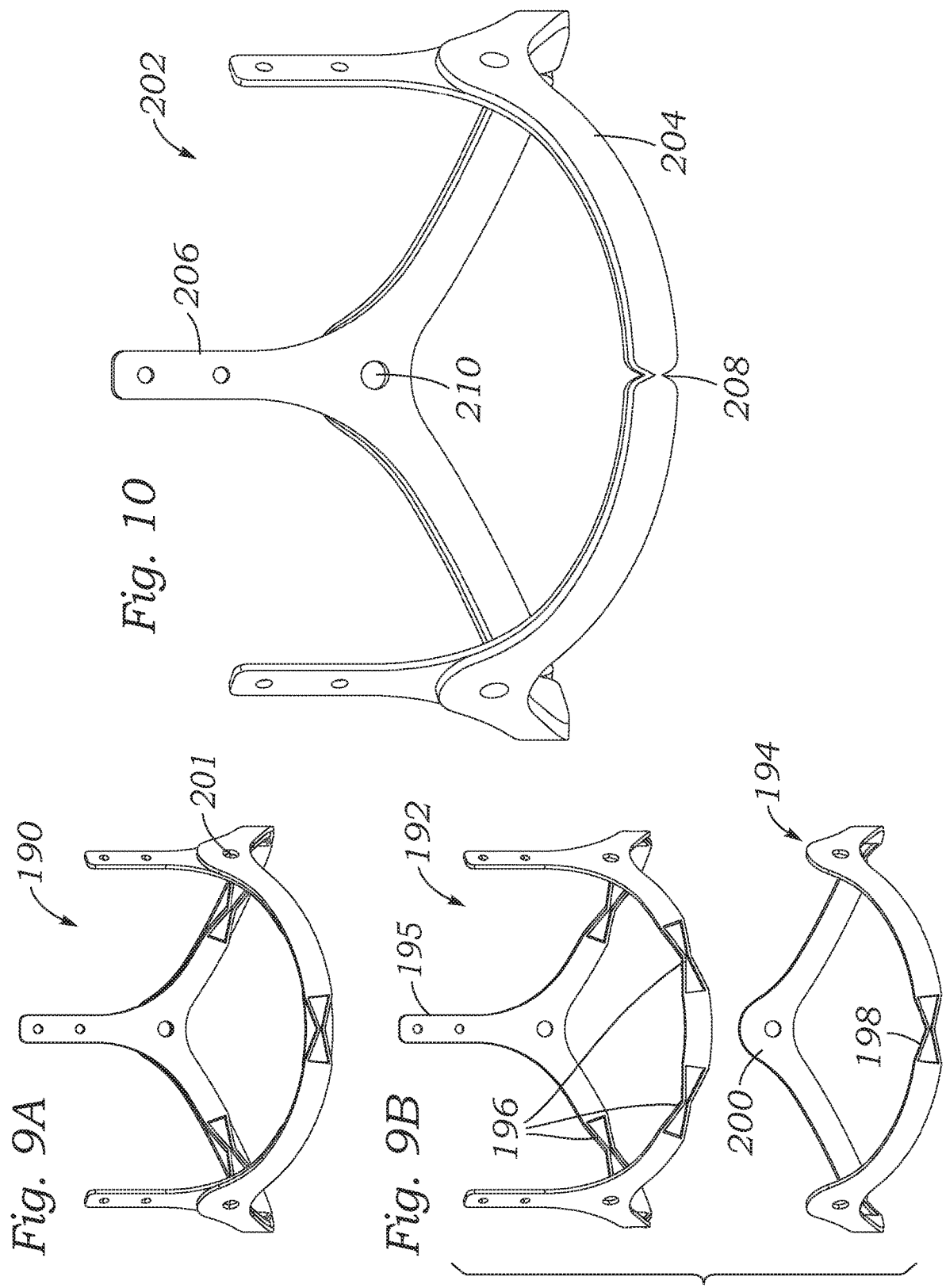

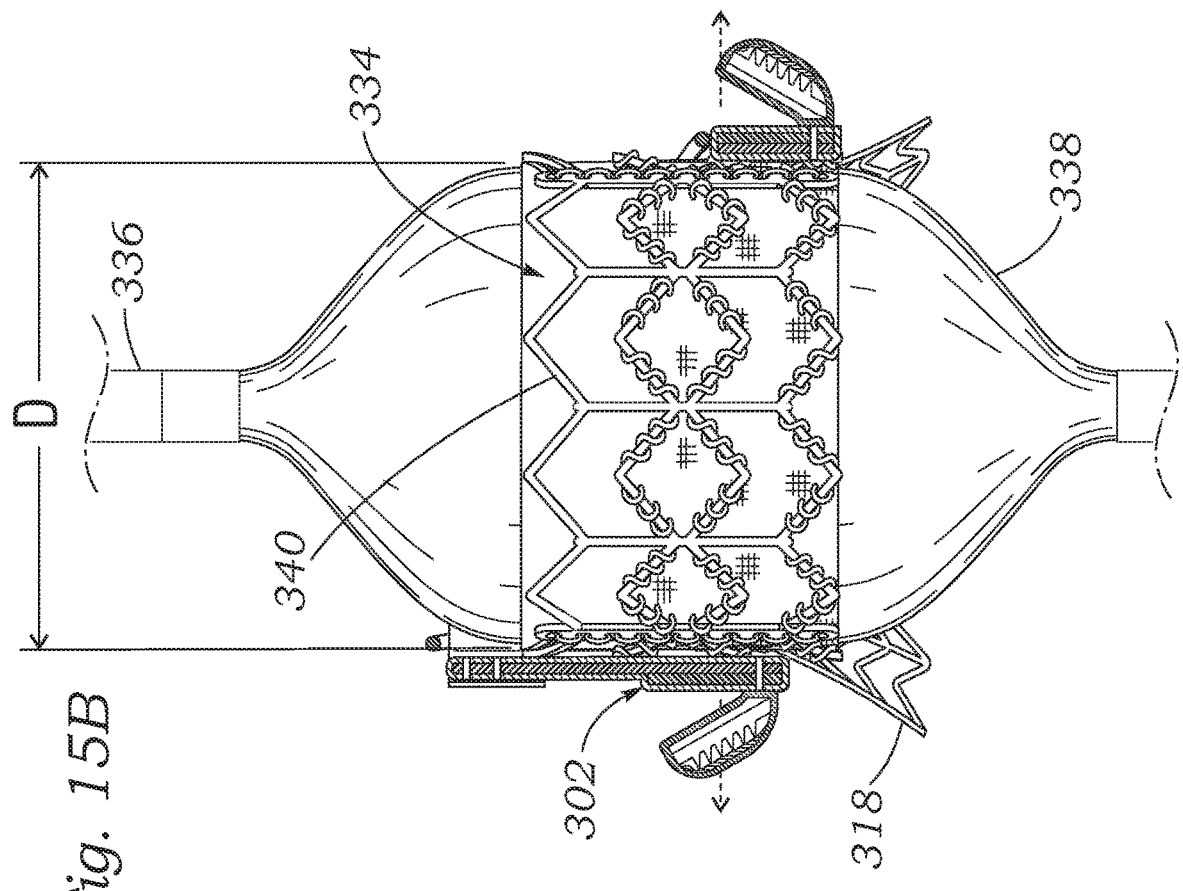
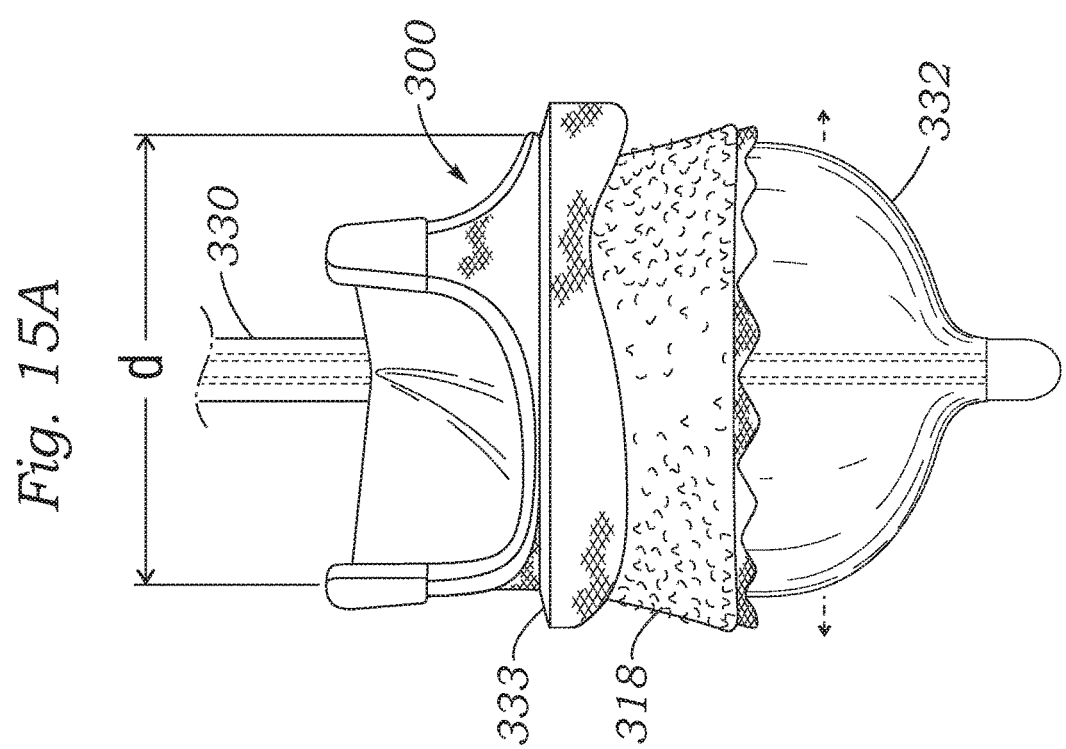
Fig. 15A
Fig. 15B

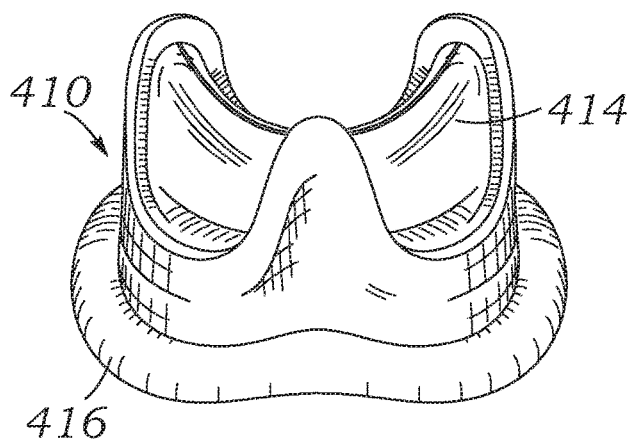
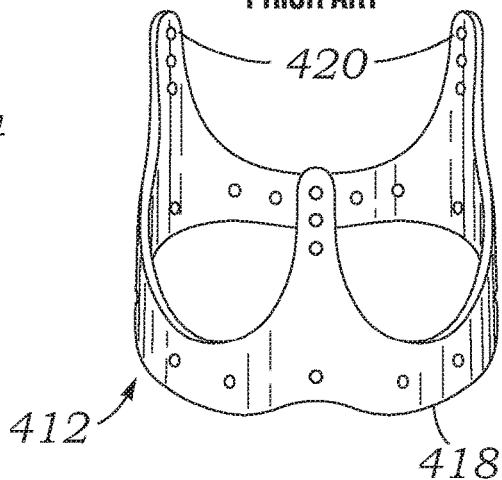
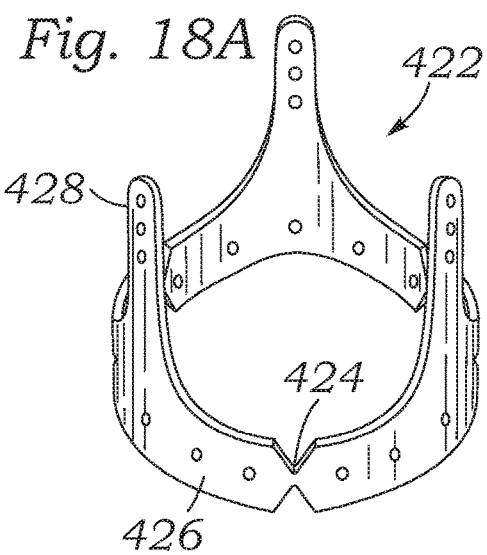
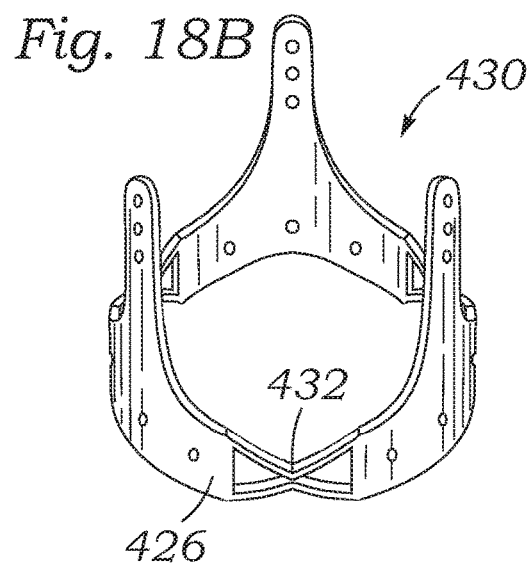
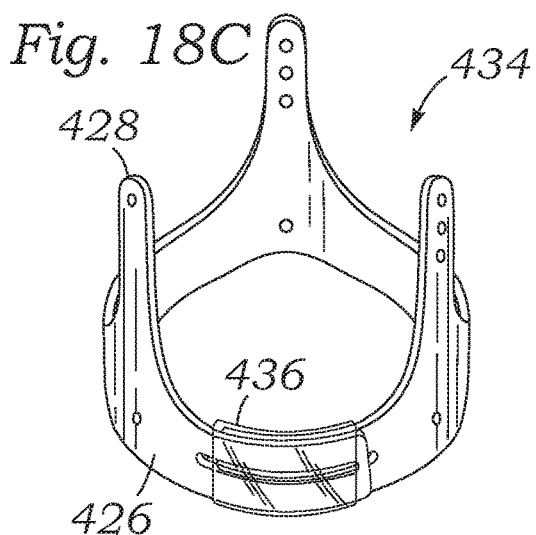
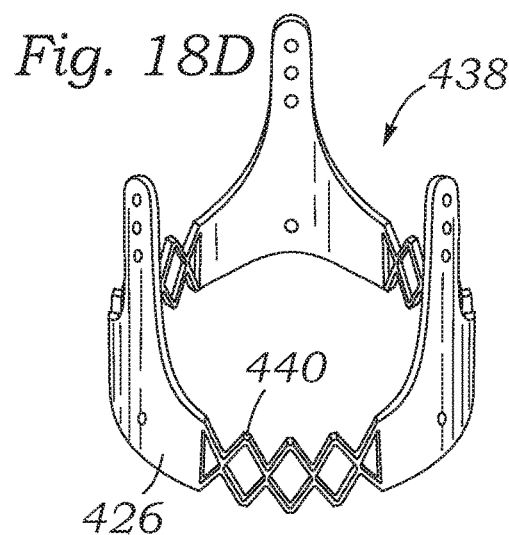

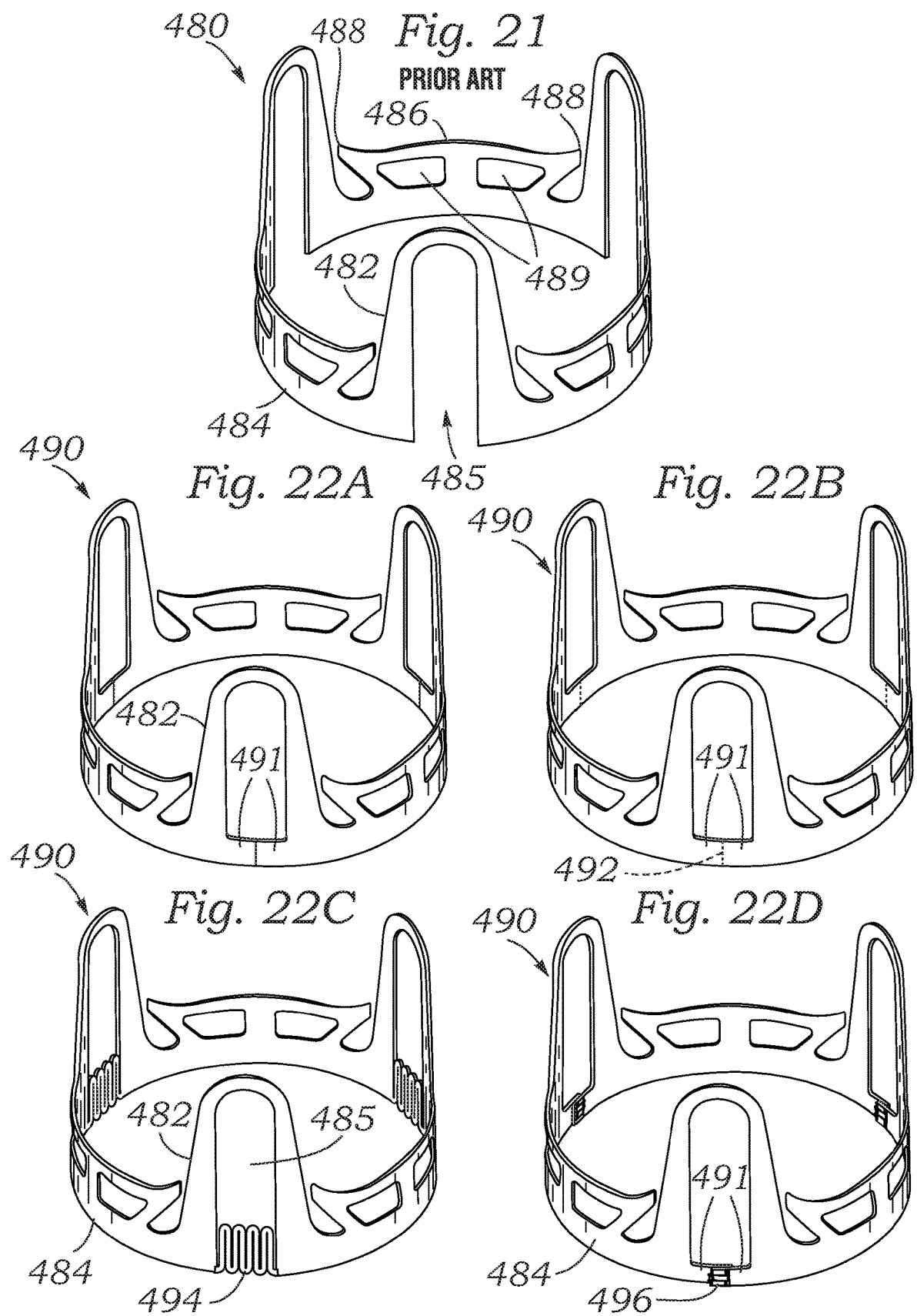

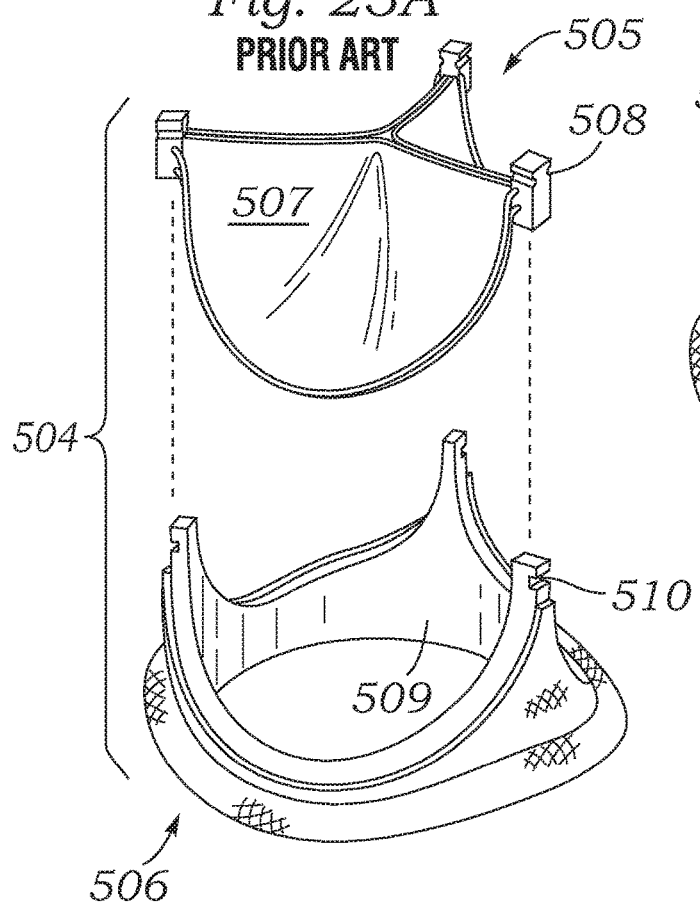
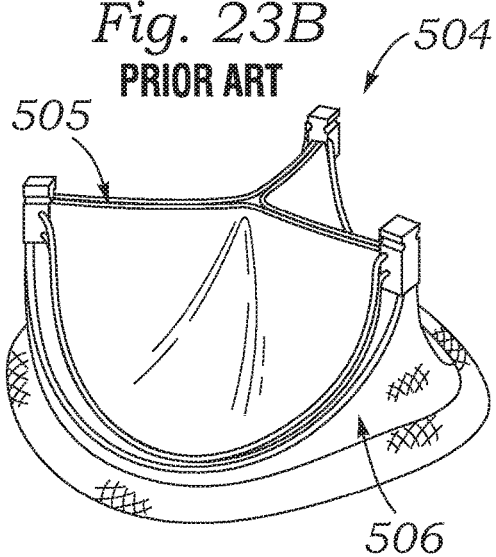
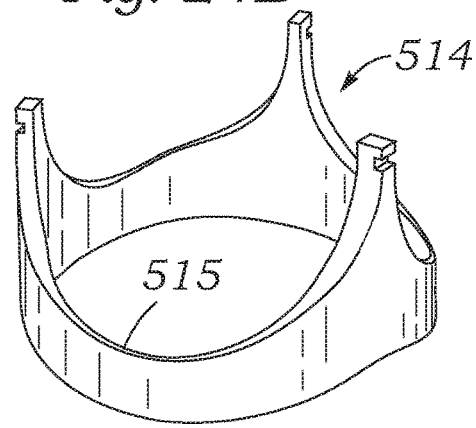
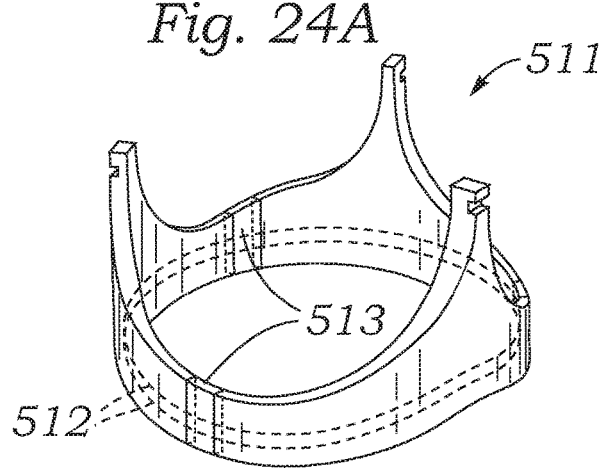
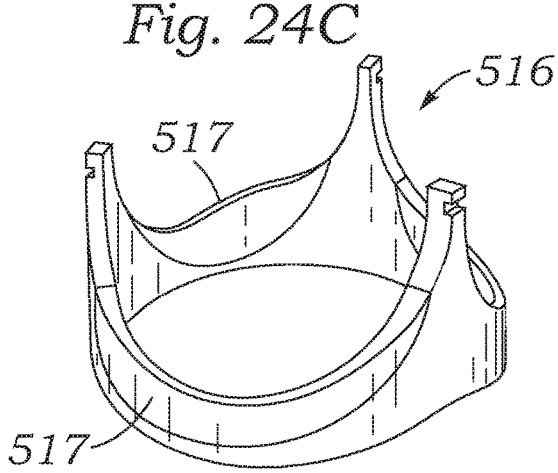

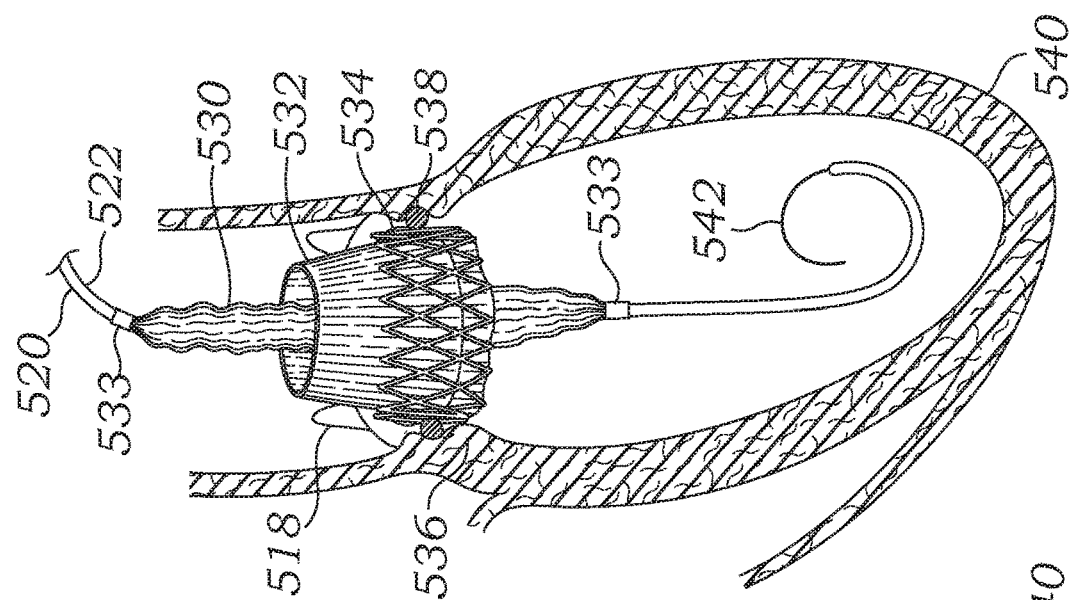
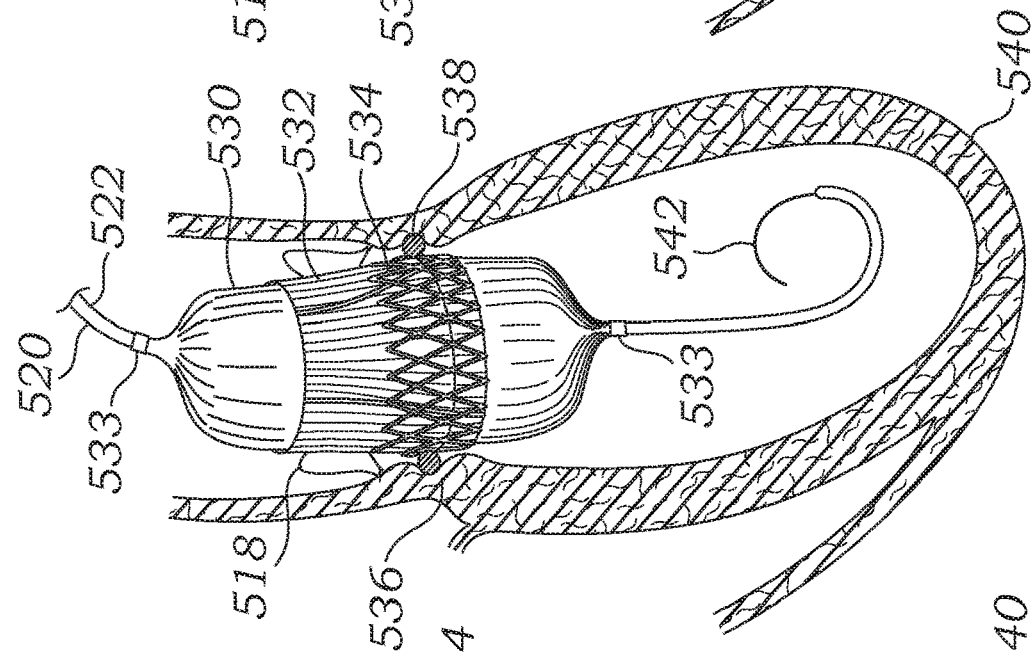
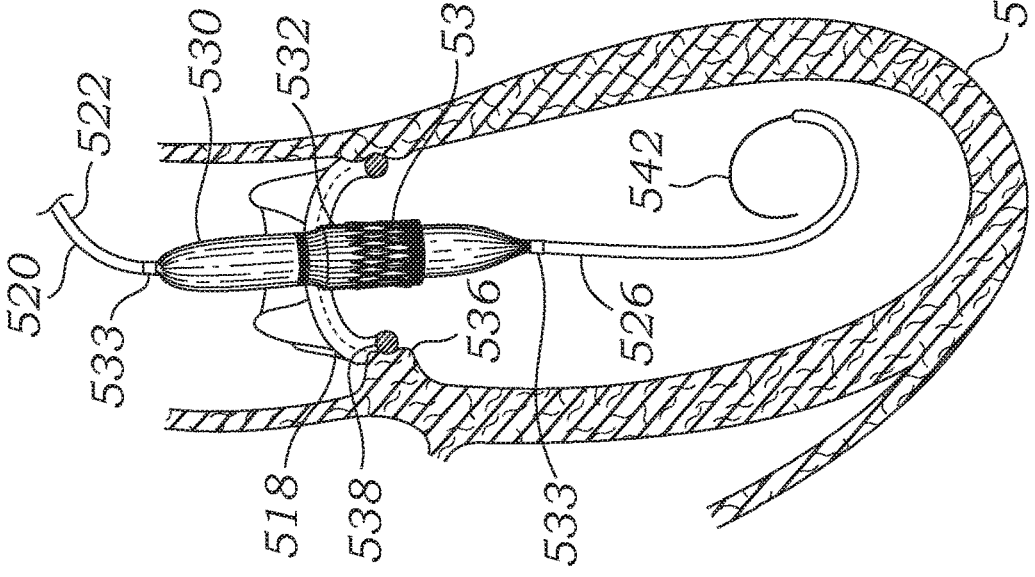

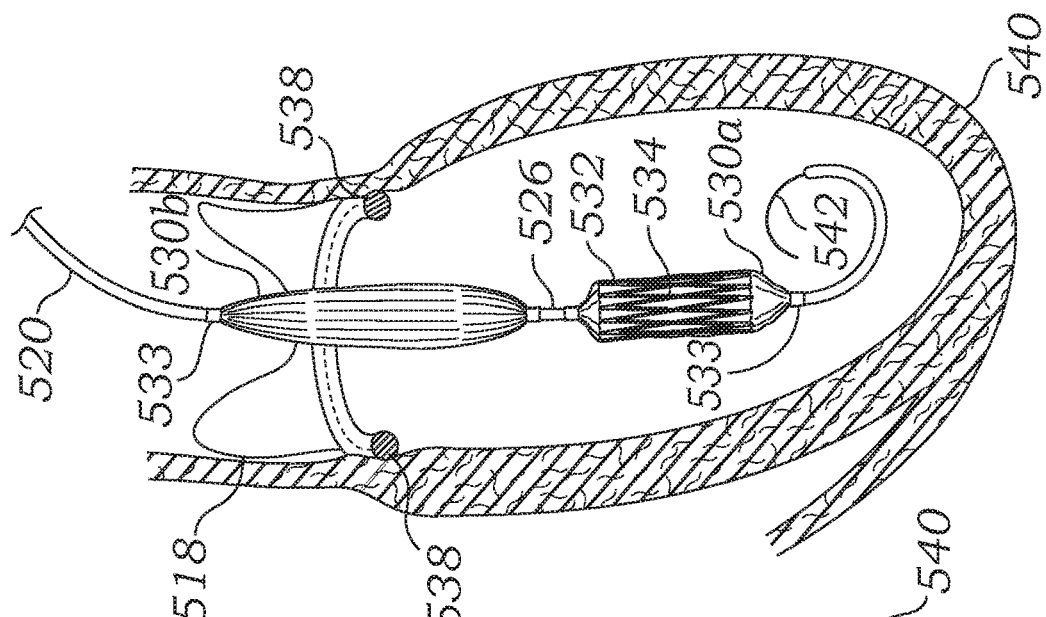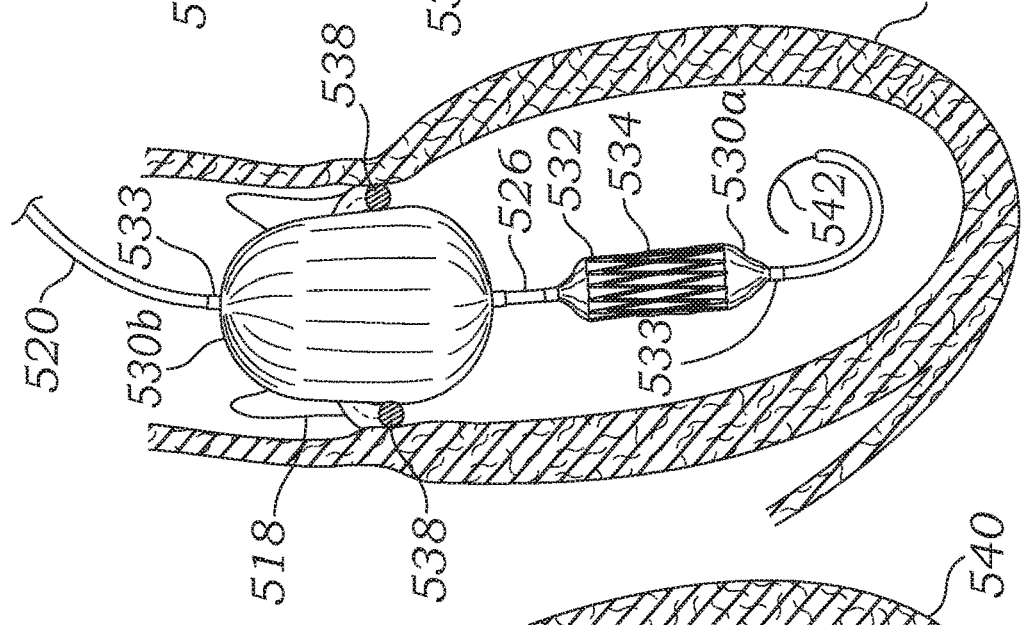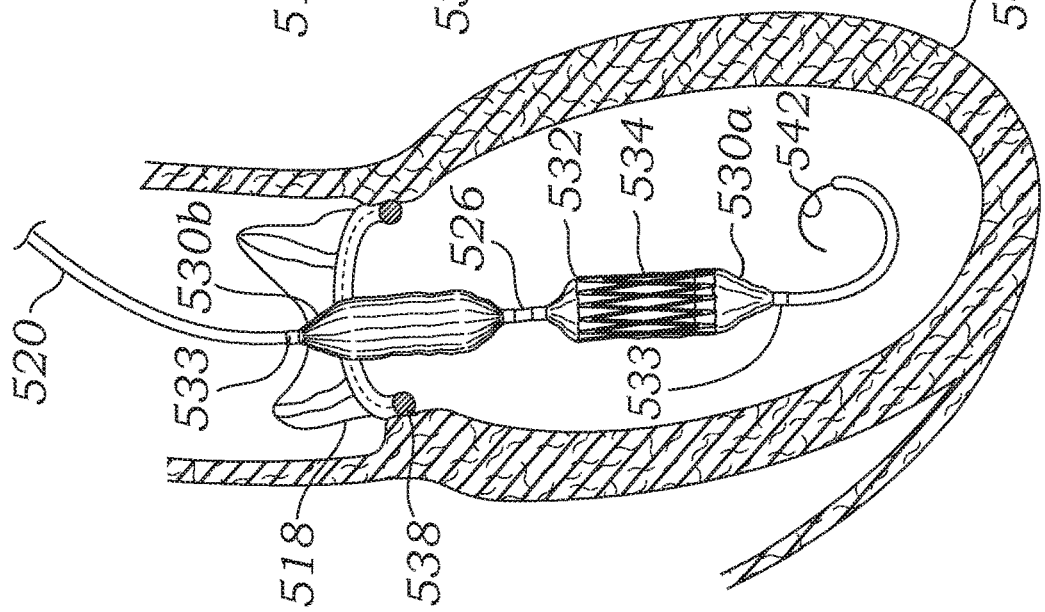

ONE-PIECE HEART VALVE STENTS ADAPTED FOR POST-IMPLANT EXPANSION

CROSS-REFERENCE TO RELATED APPLICATIONS

This application is a continuation of U.S. patent application Ser. No. 16/007,879, filed Jun. 13, 2018, now U.S. Pat. No. 10,543,085, which is a continuation-in-part of U.S. patent application Ser. No. 15/624,427, filed Jun. 15, 2017, now U.S. Pat. No. 10,485,661, which is a continuation of U.S. patent application Ser. No. 15/190,094, filed Jun. 22, 2016, now U.S. Pat. No. 10,052,200, which is a continuation of U.S. patent application Ser. No. 14/136,318, filed Dec. 20, 2013, now U.S. Pat. No. 9,375,310, which claims the benefit of U.S. Patent Application No. 61/748,022, filed Dec. 31, 2012, the entire disclosures all of which are incorporated herein by reference for all purposes. The present application is also related to U.S. patent application Ser. No. 12/234,559, filed Sep. 19, 2008, entitled "Prosthetic Heart Valve Configured to Receive a Percutaneous Prosthetic Heart Valve Implantation," and related to U.S. patent application Ser. No. 12/234,580, filed Sep. 19, 2008, entitled "Annuloplasty Ring Configured to Receive a Percutaneous Prosthetic Heart Valve Implantation," the entire disclosures all of which are expressly incorporated herein by reference for all purposes.

FIELD OF THE INVENTION

The present invention relates to a surgical heart valve for heart valve replacement, and more particularly to modifications to the construction of existing surgical heart valves to enable them to receive an expandable prosthetic heart valve therein.

BACKGROUND OF THE INVENTION

The heart is a hollow muscular organ having four pumping chambers separated by four heart valves: aortic, mitral (or bicuspid), tricuspid, and pulmonary. Heart valves are comprised of a dense fibrous ring known as the annulus, and leaflets or cusps attached to the annulus.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated. Various surgical techniques may be used to replace or repair a diseased or damaged valve. In a traditional valve replacement operation, the damaged leaflets are typically excised and the annulus sculpted to receive a replacement prosthetic valve.

A prosthetic heart valve typically comprises a support structure (such as a frame, ring and/or stent) with a valve assembly deployed therein. The support structure is often rigid, and can be formed of various biocompatible materials, including metals, plastics, ceramics, etc. Two primary types of "conventional" heart valve replacements or prostheses are known. One is a mechanical-type heart valve that uses a ball and cage arrangement or a pivoting mechanical closure supported by a base structure to provide unidirectional blood flow, such as shown in U.S. Pat. No. 6,143,025 to Stobie, et al. and U.S. Pat. No. 6,719,790 to Brendzel, et al., the entire disclosures of which are hereby expressly incorporated by reference. The other is a tissue-type or "bioprosthetic" valve having flexible leaflets supported by a base structure and projecting into the flow stream that function much like those of a natural human heart valve and imitate their natural flexing action to coapt against each other and ensure one-way blood flow.

In tissue-type valves, a whole xenograft valve (e.g., porcine) or a plurality of xenograft leaflets (e.g., bovine pericardium) can provide fluid occluding surfaces. Synthetic leaflets have been proposed, and thus the term "flexible leaflet valve" refers to both natural and artificial "tissue-type" valves. In a typical tissue-type valve, two or more flexible leaflets are mounted within a peripheral support structure that usually includes posts or commissures extending in the outflow direction to mimic natural fibrous commissures in the native annulus. The metallic or polymeric "support frame," sometimes called a "wireform" or "stent," has a plurality (typically three) of large radius cusps supporting the cusp region of the flexible leaflets (i.e., either a whole xenograft valve or three separate leaflets). The ends of each pair of adjacent cusps converge somewhat asymptotically to form upstanding commissures that terminate in tips, each extending in the opposite direction as the arcuate cusps and having a relatively smaller radius. Components of the valve are usually assembled with one or more biocompatible fabric (e.g., Dacron) coverings, and a fabric-covered sewing ring is provided on the inflow end of the peripheral support structure.

One example of the construction of a flexible leaflet valve is seen in U.S. Pat. No. 6,585,766 to Huynh, et al. (issued Jul. 1, 2003), in which the exploded view of FIG. 1 illustrates a fabric-covered wireform 54 and a fabric-covered support stent 56 on either side of a leaflet subassembly 52. The contents of U.S. Pat. No. 6,585,766 are hereby incorporated by reference in their entirety. Other examples of valve and related assemblies/systems are found in U.S. Pat. No. 4,084,268, which issued Apr. 18, 1978; U.S. Pat. No. 7,137,184, which issued on Nov. 21, 2006; U.S. Pat. No. 8,308,798, filed Dec. 10, 2009; U.S. Pat. No. 8,348,998, filed Jun. 23, 2010; and U.S. Patent Publication No. 2012/0065729, filed Jun. 23, 2011; the entire contents of each of which are hereby incorporated by reference in their entirety.

Sometimes the need for complete valve replacement may arise after a patient has already had an earlier valve replacement for the same valve. For example, a prosthetic heart valve that was successfully implanted to replace a native valve may itself suffer damage and/or wear and tear many years after initially being implanted. Implanting the prosthetic heart valve directly within a previously-implanted prosthetic heart valve may be impractical, in part because the new prosthetic heart valve (including the support structure and valve assembly) will have to reside within the annulus of the previously-implanted heart valve, and traditional prosthetic heart valves may not be configured to easily receive such a valve-within-a-valve implantation in a manner which provides secure seating for the new valve while also having a large enough annulus within the new valve to support proper blood flow therethrough.

Some attention has been paid to the problem of implanting a new valve within an old valve. In particular, the following disclose various solutions for valve-in-valve systems: U.S. Patent Publication No. 2010/0076548, filed Sep. 19, 2008; and U.S. Patent Publication No. 2011/0264207, filed Jul. 7, 2011.

Despite certain advances in the valve-in-valve area, there remains a need for a prosthetic heart valve which can properly replace a damaged heart valve, such as a prosthetic valve configured to replace a native valve via surgical implantation, but which also enable a replacement expandable prosthetic heart valve to be deployed therein at a later time without loss of flow capacity. The current invention meets this need.

SUMMARY OF THE INVENTION

The invention is a prosthetic heart valve configured to receive a prosthetic heart valve, such as a catheter-deployed (transcatheter) prosthetic heart valve, therein. In one embodiment, the prosthetic heart valve has a support structure which is substantially resistant to radial compression (and which may be substantially resistant to radial expansion) when deployed in the patient's native heart valve annulus to replace the native heart valve (or to replace another prosthetic heart valve), but is configured to be radially expandable, and/or to transform to a generally expanded and/or expandable configuration, in order to receive a prosthetic heart valve therein, such as a percutaneously-delivered prosthetic heart valve. The transformation from expansion-resistant to expanded/expandable can be achieved by subjecting the expansion-resistant support structure to an outward force, such as a dilation force, which may be provided by a dilation balloon used to deploy a replacement prosthetic valve.

In one important aspect, the present application discloses specific modifications to existing surgical valves that enable manufacturers to rapidly produce a valve which accommodates valve-in-valve (ViV) procedures. Specifically, the present application contemplates retrofitting or modifying components within existing commercial surgical valves to enable post-implant expansion.

A preferred embodiment is a prosthetic heart valve adapted for post-implant expansion and having an inflow end and an outflow end. The valve includes an inner structural support stent including a generally circular composite band having upstanding commissure posts and comprising an outer band surrounding and attached to an inner band that defines the commissure posts. The stent defines an implant circumference that is substantially non-compressible in normal physiological use and has a first diameter. The outer band has at least one expandable segment around its periphery that permits expansion of the support stent from the first diameter to a second diameter larger than the first diameter upon application of an outward dilatory force from within the support stent substantially larger than forces associated with normal physiological use. The stent supports a plurality of flexible leaflets configured to ensure one-way blood flow therethrough.

In one aspect, the outer band includes a single expandable segment located at either one of the cusps or one of the commissures formed by overlapping free ends. The overlapping free ends of the outer band may each include at least one hole that register with one another and a suture passed through the registered holes maintain the free ends aligned but are configured to break when the support stent is subjected to the outward dilatory force. Alternatively, the overlapping free ends of the outer band includes interlaced tabs that engage one another to maintain alignment of the free ends and permit a limited expansion of the support ring. The tabs may have bulbous heads connected to the free ends by slimmer stems. Still further, the overlapping free ends of the outer band may overlap with one outside the other and a sleeve surrounds them to maintain alignment of the free ends. Circumferential slots may be provided along each free end that extend wider than the sleeve when the support stent is in the first unexpanded configuration and permit fluid flow within a cavity defined by the sleeve. In one version, the overlapping free ends of the outer band are located below one of the commissure posts of the inner band and the inner band further includes a notch at an inflow edge of the one commissure post to facilitate radial expansion thereof. Still further, the overlapping free ends of the outer band may each includes at least one hole that register and a polymer element passed through the registered holes maintains the free ends aligned but is configured to break when the support stent is subjected to the outward dilatory force.

In a different embodiment, the expandable segment comprises at least one tab on one free end bent around the other free end. Alternatively, the expandable segment comprises at least one tab on one free end that projects through a slot in the other free end. Desirably, the inner band is a single polymer band, and the outer band is a single metallic band. The expandable segment may comprise a series of interconnected struts connected end-to-end by hinge-like connections which forms a zig-zag accordion-like structure having substantially diamond-shaped cells. Alternatively, the expandable segment comprises a substantially serpentine structure formed by plastically-expandable struts.

In one form, the prosthetic heart valve is a two-part valve with the plurality of flexible leaflets being mounted on a detachable frame that couples to the support stent at the commissure posts thereof. The valve may further include a cloth covering surrounding the support stent and facilitating attachment of the leaflet peripheral edges along the support stent outflow edge. A unique identifier may be provided on the support stent visible from outside the body after implant that identifies the support stent as being expandable. A biodegradable band may be disposed concentrically and in close contact with the structural stent, the biodegradable band configured to provide resistance to expansion of the support stent after implantation which resistance lessens over time as the band degrades in the body. The prosthetic heart valve further may have a radially-expandable inflow stent secured to and projecting from an inflow end of the support stent, wherein the radially-expandable inflow stent has a strength requiring a predetermined expansion force to convert from a compressed state to an expanded state, and wherein the biodegradable band is configured to provide resistance to expansion of the support stent when the predetermined expansion force is applied to the radially-expandable inflow stent.

The prosthetic heart valve structure may be generally rigid prior to dilation, and may be configured to become generally non-rigid, and even generally elastic, when subjected to an outward force. The elasticity may assist in holding a percutaneously-introduced prosthetic valve within the current prosthetic valve structure. The prosthetic heart valve structure may be configured to be resistant to radial compression, but to permit radial expansion when subjected to radially expansive forces, and potentially to even relatively small radially expansive forces.

The prosthetic valve can be initially deployed in the patient's valve annulus using various surgical techniques (e.g., traditional open-chest, minimally-invasive, percutaneous, etc.) to correct heart valve function. If the heart valve function declines further after deployment of the prosthetic valve, a new replacement prosthetic valve can be deployed within the previously-deployed prosthetic valve without the need to excise the previously-deployed prosthetic valve.

Deployment of the replacement prosthetic valve within the previously-deployed prosthetic valve can occur at a much later time from initial deployment of the previously-deployed prosthetic valve. The prosthetic valve of the current invention is thus configured to be deployed in a patient and, at a later time, to accept and even improve deployment of a replacement prosthetic valve within the same valve annulus.

In an embodiment of the invention, the prosthetic valve is a stented bioprosthetic valve configured to expand and contract dynamically within the patient's annulus. The dynamic motion of the annulus can enable the valve opening to expand during periods of peak demand, and reduce the annular restriction to the increased flow. The expansion can also decrease leaflet stresses associated with potential higher gradients. The expansion can also permit later placement of an expandable prosthetic valve within the stented bioprosthetic valve. In such an embodiment, the prosthetic valve may have a set minimum radius beneath which it will not compress radially. The prosthetic valve may have a set maximum radius beyond which it will not radially expand, even if subjected to radially expansive forces up to the 6 atm range typically seen in balloon catheters used to deliver and deploy balloon-expandable percutaneously-deliverable stented prosthetic heart valves.

In an embodiment of the invention, a prosthetic valve has a composite support structure having a generally rigid and/or expansion-resistant portion with a substantially flexible and/or stretchable portion. The prosthetic valve may include plastically deformable materials configured to maintain the prosthetic valve support structure in the generally rigid and/or expansion-resistant shape for deployment. The plastically deformable materials may be configured to break or otherwise plastically deform and no longer maintain the support structure in the generally rigid and/or expansion-resistant configuration when subjected to a dilation force. The support structure may form a continuous loop, and may include elastically deformable material configured to provide tension about the continuous loop after the support structure has been dilated by a dilation balloon or other mechanical expander.

A method for repairing a patient's heart function according to an embodiment of the invention can include: providing a prosthetic heart valve configured to have a generally rigid and/or expansion-resistant support structure upon implantation and also configured to assume a generally expanded configuration upon dilation; and implanting the prosthetic heart valve in a heart valve annulus. The method may also include deploying an expandable prosthetic heart valve within the previously-deployed heart valve and heart valve annulus. Deploying the expandable prosthetic heart valve within the previously-deployed prosthetic valve and heart valve annulus may include dilating the previously-deployed prosthetic valve to cause the previously-deployed prosthetic valve to assume a generally expanded shape.

Dilating a previously-deployed prosthetic heart valve may include using a dilation balloon, such as the type currently used for dilation of native heart valves, which can be advanced within the previously-deployed prosthetic heart valve and expanded to a desired pressure and/or diameter. As a general rule, dilation balloons used for dilation of native valves are formed from generally inelastic material to provide a generally fixed (i.e., pre-set) outer diameter when inflated. Once such balloons are inflated to their full fixed diameter, they will not appreciably expand further (prior to rupturing) even if additional volume/pressure is added therein. Typical pressures for inflating such balloons are between 1 and 12, and more preferably between 1 and 8 atmospheres, with pre-set inflated outer diameters of such balloons being on the order of 18 to 33 millimeters. The dilation balloon may be expanded to a desired pressure (e.g., 1-12 atmospheres) sufficient to fully inflate the dilation balloon to its desired diameter and to dilate and expand the previously-deployed prosthetic heart valve.

A typical surgically-implanted prosthetic heart valve will withstand dilation pressures of several atmospheres such as provided by most dilation balloons without expanding and/or becoming elastic. By contrast, the prosthetic heart valve described herein is configured to become expanded and/or generally elastic when subjected to sufficient pressure provided by a dilation balloon or other mechanical expander. If the dilation balloon is expanded, using sufficient pressure, to an expanded outer diameter larger than the inner diameter of the prosthetic heart valve of the invention, the prosthetic heart valve will expand in diameter and/or become elastic.

In one embodiment, the dilation balloon is configured with a pre-set inflated outer diameter which is larger, such as by 2 to 3 mm, or 10-20% or more, than the inner diameter of the previously-deployed prosthetic heart valve. As an example, if the previously-deployed prosthetic heart valve of the invention has an inner diameter of 23 mm, a dilation balloon having an inflated diameter of 24-27 mm may be inflated within the prosthetic heart valve to cause it to expand and/or become elastic.

Prosthetic heart valves according to various embodiments of the invention can be configured to be generally rigid prior to dilation, but become expanded and/or elastic when subjected to a sufficient dilation pressure. For example, a prosthetic heart valve could be configured to withstand naturally occurring dilation pressures that may occur during beating of the heart, but to become expanded and/or elastic when subjected to a desired pressure (e.g., from a dilation balloon), such as a pressure of 1 atmosphere, 2 atmospheres, 3 atmospheres, 4 atmospheres, 5 atmospheres, or 6 atmospheres, or up to 12 atmospheres, depending on the particular application.

In one particular embodiment of the invention, a prosthetic heart valve has an inflow end and an outflow end, with an unexpanded configuration and an expanded configuration. A support structure defines the circumference, and has a smaller inner diameter when the prosthetic heart valve is in the unexpanded configuration and a larger inner diameter when the prosthetic heart valve is in the second expanded configuration. The support structure rigidly resists inward compression when the prosthetic heart valve is in the unexpanded configuration. The valve portion is supported by the support structure, and comprises multiple leaflets. When the prosthetic heart valve is in the unexpanded configuration each leaflet is configured to coapt with adjacent leaflets to permit blood to flow through the prosthetic heart valve, but to prevent blood from flowing through the prosthetic heart valve in the opposite direction. The support structure may have a first support portion passing substantially around the circumference of the support structure and comprising a polymeric material. The first support portion may be formed as single unitary assembly of polymeric material, and may have a weakened section configured to structurally fail when the support structure is subjected to a sufficient dilation force. The support structure may have a second support portion passing substantially around the circumference of the support structure and formed from a metal, such as cobalt-chromium or stainless steel. The second support portion may have a weakened section configured to structurally fail when the support structure is subjected to the same dilation force that causes the weakened section of the first support portion to fail. The dilation force may be 2 atmospheres or more. The first support portion and the second support portion may be secured together at multiple points around the circumference of the support structure. The first support portion weakened section and the second support portion weakened section may be positioned adjacent each other about the circumference of the support structure, or may be spaced apart from each other about the circumference of the support structure. The weakened section of the first support portion may comprise a thinned area of the first support portion, and the second support portion weakened section may comprise a spot weld on the second support portion. The second support portion weakened section may comprise two openings in the second support portion with a suture passing through the two openings. The first support portion may comprise polyester, and the second support portion may comprise a metal such as cobalt-chromium (Co—Cr) alloy.

A prosthetic heart valve according to the invention may further have an additional support portion in the form of a support portion positioned at the inflow end of the prosthetic heart valve, with the third support portion configured to radially expand into a substantially flared shape when subjected to a dilation force that is by itself insufficient to cause expansion of the main support structure. The third support portion may be positioned upstream of the entire valve portion.

The first support portion may comprise a one-piece polymeric structure defining 3 polymeric commissural supports extending lengthwise along the prosthetic heart valve and also defining 3 polymeric curved connections extending circumferentially about the prosthetic heart valve, wherein each curved connection connects two adjacent commissural supports, and wherein the second support portion comprises a one-piece metal structure comprising 3 metal curved connections extending circumferentially about the prosthetic heart valve, wherein the 3 metal curved connections are positioned against and radially outside of the 3 polymeric commissural supports.

In a further embodiment of the invention, a prosthetic heart valve has an inflow end and an outflow end, and has a first unexpanded configuration and a second expanded configuration. The valve may have a support structure comprising multiple commissural supports with valve expansion portions extending circumferentially between adjacent commissural supports. The expansion portions may prevent compression of the support structure when the prosthetic heart valve is in the unexpanded configuration, but permit radial expansion of the support structure from a first diameter to a second diameter when the prosthetic heart valve is subjected to a dilation force of more than 2 atmospheres.

In the expanded configuration, the leaflets of the prosthetic heart valve (which had coapted to control blood flow prior to expansion) may not coapt as well, or not at all. Accordingly, the leaflets (post-expansion) may permit substantial blood to flow in both directions. The leaflets are thus largely ineffective in controlling blood flow post-expansion. Control of the blood flow will thus be assumed by a newly implanted prosthetic valve deployed within the orifice of the prior (and now-dilated) prosthetic valve.

Expansion portions of support structures according to the invention may have a substantially serpentine structure formed from metal struts, wherein the metal struts have ends as well as sides, wherein adjacent metal struts are connected in end-to-end configuration, wherein in the unexpanded configuration the metal struts are positioned side-to-side with sides of adjacent metal struts touching sides of adjacent metal struts. Due to the relative thinness of current and projected percutaneously delivered/radially expandable prosthetic heart valves, the amount of radial expansion required of the prosthetic heart valves described herein does not have to be greater than 1 to 5 millimeters, with 2 to 3 millimeters being more typical for the embodiments herein. For example, a radial expansion of about 2 to 3 millimeters may be sufficient to provide space for full deployment of a new percutaneous prosthetic valve within an existing and expanded prosthetic valve, with the orifice of the newly deployed percutaneous prosthetic valve being the same size as was the orifice (pre-dilation) of the originally-deployed (and now dilated) prosthetic valve.

Non-limiting examples of inner diameters/orifices (pre- and post-expansion) of embodiments of the current invention include: 15 mm which expands to 17 or 18 mm; 17 mm which expands to 19 or 20 mm; 19 mm which expands to 21 or 22 mm; 22 mm which expands to 24 or 25 mm; 25 mm that expands to 28 mm; 27 mm that expands to 30 mm; 30 mm which expands to 33 mm.

Valves and supports according to the embodiments of the invention may be specifically configured to resist radial expansion until subjected to a designated pressure, above which radial expansion may occur. For example, a designated pressure of 1 atm or more (e.g., 1 to 6 atm); of 2 atm or more (e.g., 2 to 6 atm); of 3 atm or more (e.g., 3 to 6 atm); of 4 atm or more (e.g., 4 to 6 atm); of 5 atm or more (e.g., 5 to 6 atm); or of 6 atm or more may be sufficient to trigger radial expansion. Balloon inflated pressures that will trigger expansion of valve structures according to embodiments of the invention can range from 1 atmosphere up to 10 atmospheres or even higher. However, as a practical matter the lower end of this range is probably more desirable. Many balloons have a maximum rated pressure of 6 to 8 atmospheres (above which there may be risk of bursting), and it thus may be desirable for devices according to the invention to expand when subjected to pressure lower than the balloon maximum rated pressures. Accordingly, devices according to the invention may be configured to radially expand when subjected to a balloon filled to a pressure of between 4 to 5 atm, such as 4.5 atm. Devices according to the invention may be configured to expand when subjected to such designated expansion pressures, but only to expand by a selected amount (e.g., 2 to 3 millimeters)—so that further radial expansion is prevented even if the pressure is increased well above the designated expansion pressure.

Note that the dilation balloon inflated diameters and inflated pressures, as well as the pressures at which the prosthetic heart valve would become expanded and/or elastic, set forth above are by way of example, and that the use of balloons with other pressures and diameters, or other mechanical expanders, and of prosthetic heart valves configured to change shape and/or expand and/or become elastic when subjected to other pressures and expanded balloon diameters, are also within the scope of the invention.

Other features and advantages of the present invention will become apparent from the following detailed description, taken in conjunction with the accompanying drawings which illustrate, by way of example, the principles of the invention.

BRIEF DESCRIPTION OF THE DRAWINGS

FIGS. 5A-5D are perspective and exploded views of an exemplary prosthetic heart valve of the prior art having inner structural bands;

FIGS. 6A-6B, 7A-7B, and 8A-8B are perspective assembled and exploded views of different embodiments of replacement structural bands for the prior art prosthetic heart valve shown in FIG. 5A that enables the heart valve to expand post-implantation;

FIGS. 9A-9B are perspective assembled and exploded views of an alternative combination of structural bands that can be substituted into the prior art prosthetic heart valve of FIG. 5A to enable post-implantation expansion thereof;

FIG. 10 is a perspective view of a still further alternative molded structural band for substitution into the prior art prosthetic heart valve of FIG. 5A;

FIG. 15A is an elevational view of the assembled prosthetic heart valve of FIG. 15 during a step of balloon-expanding an anchoring skirt, and FIG. 15B is a sectional view through the prosthetic heart valve during a post-implantation procedure of expanding the first valve while implanting a secondary heart valve therewithin;

FIG. 17A is a perspective view of another commercially-available surgical prosthetic heart valve of the prior art, and FIG. 17B is a perspective view of an inner support stent thereof;

FIGS. 18A-18D are perspective views of modifications to the inner support stent of FIG. 17B that will enable the heart valve of FIG. 17A to expand post-implantation;

FIG. 21 is a perspective view of an inner support stent of another surgical prosthetic heart valve;

FIGS. 22A-22D are perspective views of modifications to the inner support stent of FIG. 21 that will enable the heart valve to expand post-implantation;

FIG. 23A is a perspective view of another commercially-available surgical prosthetic heart valve of the prior art having two detachable components, and FIG. 23B is a perspective view of the two components coupled together to form a functioning prosthetic heart valve;

FIGS. 24A-24C are perspective views of modifications to the inner support stent of FIG. 23B that will enable a base member of the two-part heart valve of FIG. 23A to expand post-implantation;

FIG. 25B depicts the expandable prosthetic heart valve deployment catheter of FIG. 25A positioned within a previously-deployed prosthetic heart valve in a heart valve annulus of a patient according to an embodiment of the invention;

FIG. 25C depicts the expandable prosthetic heart valve deployment catheter of FIG. 25A dilating the previously-deployed prosthetic heart valve and deploying an expandable prosthetic heart valve therewithin according to an embodiment of the invention;

FIG. 25D depicts the expandable prosthetic heart valve deployment catheter of FIG. 25A being withdrawn from the patient according to an embodiment of the invention;

FIG. 26B depicts the expandable prosthetic heart valve deployment catheter of FIG. 26A with the dilation balloon positioned within the previously-deployed prosthetic heart valve in the heart valve annulus according to an embodiment of the invention;

FIG. 26C depicts the expandable prosthetic heart valve deployment catheter of FIG. 26A dilating the previously-deployed prosthetic heart valve according to an embodiment of the invention;

FIG. 26D depicts the expandable prosthetic heart valve deployment catheter of FIG. 26A with the dilation balloon deflated after dilation of the previously-deployed prosthetic heart valve according to an embodiment of the invention;

DETAILED DESCRIPTION OF PREFERRED EMBODIMENTS

The prosthetic heart valves described herein each include an internal (meaning incorporated into the valve itself as opposed to being a supplemental element) stent or frame that is generally tubular in shape and defines a flow orifice area through which blood flows from an inflow end to an outflow end. Alternatively, the shape of the internal stent can be oval, elliptical, irregular, or any other desired shape. The valves include flexible leaflets that selectively allow for fluid flow therethrough. Thus, the flow orifice area is alternatively open and closed via movement of leaflets.

As referred to herein, the prosthetic heart valves used in accordance with the devices and methods of the invention may include a wide variety of different configurations, such as a prosthetic heart valve having one or more tissue leaflets, a synthetic heart valve having polymeric leaflets, and in general any that are configured for replacing a native or previously implanted prosthetic heart valve. That is, the prosthetic heart valves described herein can generally be used for replacement of aortic, mitral, tricuspid, or pulmonic valves, but may also be used as a venous valve. These replacement prosthetic heart valves can also be employed to functionally replace stentless bioprosthetic heart valves.

Various internal stents disclosed herein have "expandable segments" that enable the stent to expand. This can occur from the expandable segment rupturing, plastically stretching, or elastically elongating. Thus, an "expandable segment" means a location on the stent that enables it to enlarge in diameter, such as when a balloon is inflated within the stent. Examples include weak points which can rupture, thinned areas that rupture or stretch, accordion-like structures which elongate elastically or plastically, breaks in the stent that are held together with a breakable member such as a suture or spot weld, and various other means. The term, "expandable segment" thus encompasses each and every one of these alternatives.

Figure 1:
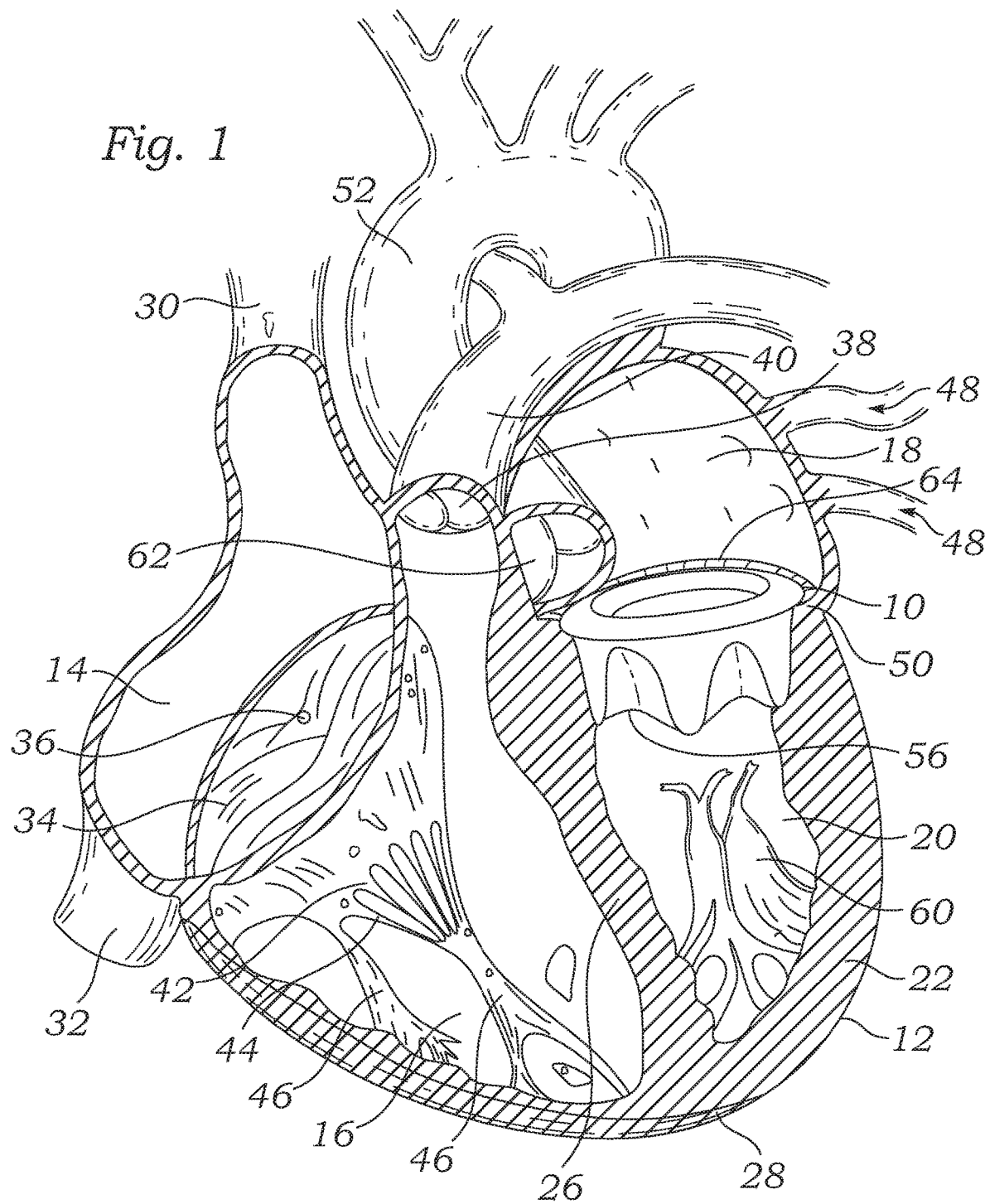
FIG. 1 depicts a prosthetic heart valve deployed in a heart according to an embodiment of the invention.

With reference to FIG. 1, a prosthetic heart valve 10 according to the invention is depicted in a heart 12. The heart 12 has four chambers, known as the right atrium 14, right ventricle 16, left atrium 18, and left ventricle 20. The general anatomy of the heart 12, which is depicted as viewed from the front of a patient, will be described for background purposes. The heart 12 has a muscular outer wall 22, with an interatrial septum 24 dividing the right atrium 14 and left atrium 18, and a muscular interventricular septum 26 dividing the right ventricle 16 and left ventricle 20. At the bottom end of the heart 12 is the apex 28.

Blood flows through the superior vena cava 30 and the inferior vena cava 32 into the right atrium 14 of the heart 12. The tricuspid valve 34, which has three leaflets 36, controls blood flow between the right atrium 14 and the right ventricle 16. The tricuspid valve 34 is closed when blood is pumped out from the right ventricle 16 through the pulmonary valve 38 to the pulmonary artery 40 which branches into arteries leading to the lungs (not shown). Thereafter, the tricuspid valve 34 is opened to refill the right ventricle 16 with blood from the right atrium 14. Lower portions and free edges 42 of leaflets 36 of the tricuspid valve 34 are connected via tricuspid chordae tendineae 44 to papillary muscles 46 in the right ventricle 16 for controlling the movements of the tricuspid valve 34.

After exiting the lungs, the newly-oxygenated blood flows through the pulmonary veins 48 and enters the left atrium 18 of the heart 12. The mitral valve in a normal heart controls blood flow between the left atrium 18 and the left ventricle 20. Note that in the current figure, the native mitral valve has been replaced with the prosthetic heart valve 10, which is accordingly a prosthetic mitral valve 50. The prosthetic mitral valve 50 is closed during ventricular systole when blood is ejected from the left ventricle 20 into the aorta 52. Thereafter, the prosthetic mitral valve 50 is opened to refill the left ventricle 20 with blood from the left atrium 18. Blood from the left ventricle 20 is pumped by power created from the musculature of the heart wall 22 and the muscular interventricular septum 26 through the aortic valve 62 into the aorta 52 which branches into arteries leading to all parts of the body.

In the particular embodiment depicted, the prosthetic heart valve 10 is deployed to replace a native mitral valve, and more particularly is secured (via, e.g., sutures) adjacent and around the mitral valve annulus 64. Depending on the particular application, including the method by which the prosthetic heart valve 10 was implanted, the particular native valve (aortic, mitral, tricuspid, etc.) and/or some or all of its associated structures may be entirely or partially removed prior to or during implantation of the prosthetic heart valve 10, or the native valve and/or some or all associated structures may simply be left in place with the prosthetic heart valve 10 installed over the native valve. For example, a native mitral valve typically has two leaflets (anterior leaflet and posterior leaflet), lower portions and free edges of which are connected via mitral chordae tendineae to papillary muscles 60 in the left ventricle 20 for controlling the movements of the mitral valve. Not all of these structures (i.e., mitral valve leaflets, chordae tendineae) are depicted in FIG. 1 because, in the particular embodiment, the native mitral valve and many associated structures (chordae, etc.) have been removed prior to or during implantation of the prosthetic heart valve 10. However, in many prosthetic valve implantations, surgeons choose to preserve many of the chordae tendineae, etc., even when excising the native valve.

Although FIG. 1 depicts a prosthetic mitral valve, note that the invention described herein can be applied to prosthetic valves (and systems and methods therefore) configured to replace any of the heart valves, including aortic, mitral, tricuspid, and pulmonary valves.

Figure 2A:
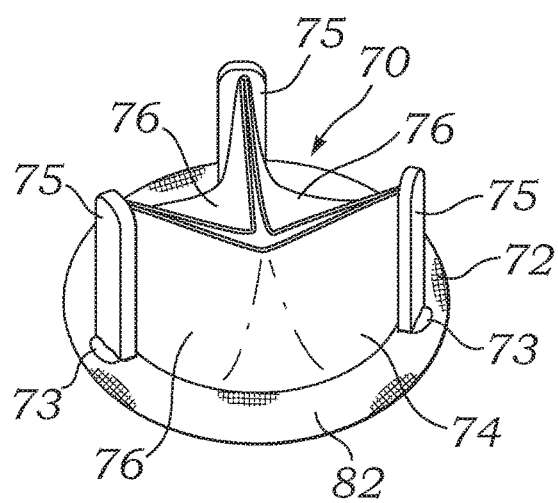
FIGS. 2A-2C depict perspective, top, and side views, respectively, of a prosthetic heart valve according to an embodiment of the invention.
Figure 2B:
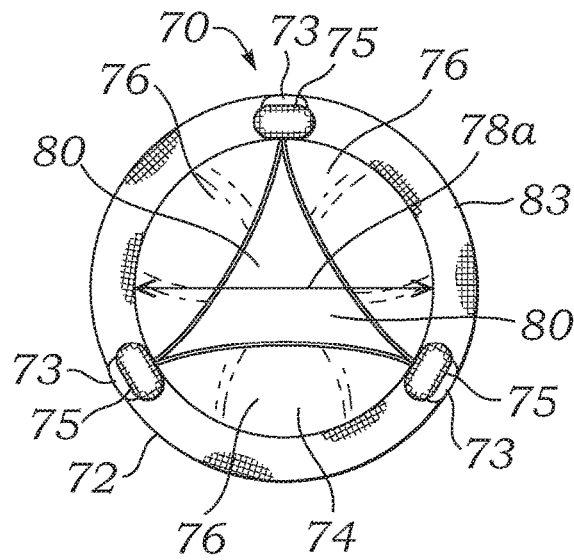
Figure 2C:
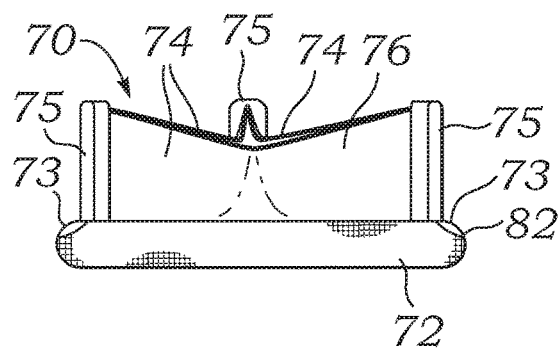

FIGS. 2A-2C depict a prosthetic heart valve 70 according to an embodiment of the invention, where the prosthetic heart valve 70 comprises a support frame 72 and valve structure 74. In the particular embodiment depicted, the valve structure 74 comprises three heart valve leaflets 76. The prosthetic heart valve 70 has an inner diameter 78a of a valve orifice 80 through which blood may flow in one direction, but the valve leaflets 76 will prevent blood flow in the opposite direction. The support frame 72 is generally rigid and/or expansion-resistant in order to maintain the particular shape (which in this embodiment is generally round) and diameter 78a of the valve orifice 80 and also to maintain the respective valve leaflets 76 in proper alignment in order for the valve structure 74 to properly close and open. The particular support frame 72 also includes commissure supports or posts 75 which help support the free edges of the valve leaflets 76. In a preferred construction, each of the valve leaflets 76 attaches along a cusp edge to the surrounding support frame 72 and up along adjacent commissure posts 75. In the particular embodiment depicted in FIGS. 2A-2C, the support frame 72 defines a generally rigid and/or expansion-resistant ring 82 which encircles the valve 70 and defines a generally round valve orifice 80, but other shapes are also within the scope of the invention, depending on the particular application (including issues such as the particular native valve to be replaced, etc.) The particular prosthetic heart valve 70 includes visualization markers 73 (such as radiopaque markers, etc.), which in the current embodiment are on the support frame 72 and correspond to the ring 82 and also to the commissure posts 75 (and hence to the commissures), which can aid in proper placement of a subsequently-deployed expandable prosthetic heart valve within the valve orifice 80 of the prosthetic heart valve 70.

Figure 2D:
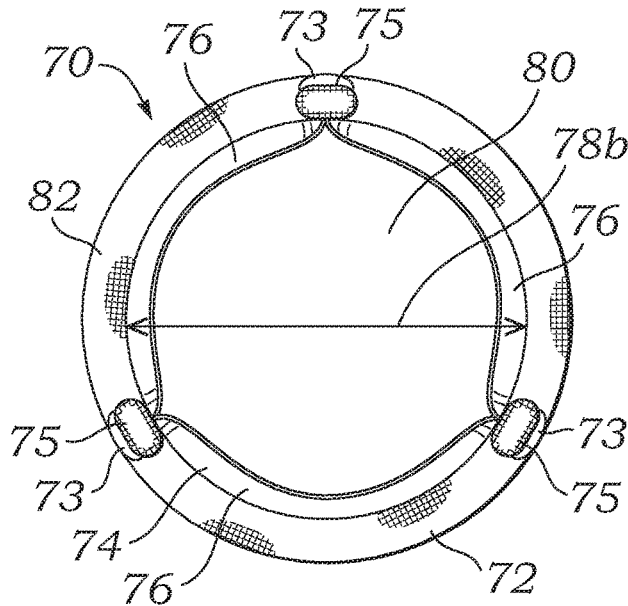
FIG. 2D depicts a top view of the prosthetic heart valve of FIGS. 2A-2C after the prosthetic heart valve has been dilated.
Figure 3A:
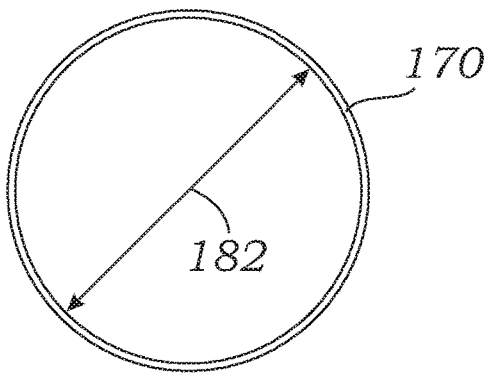
FIGS. 3A-3B depict top and side views, respectively, of a prosthetic heart valve, pre-dilation, according to an embodiment of the invention.
Figure 3C:
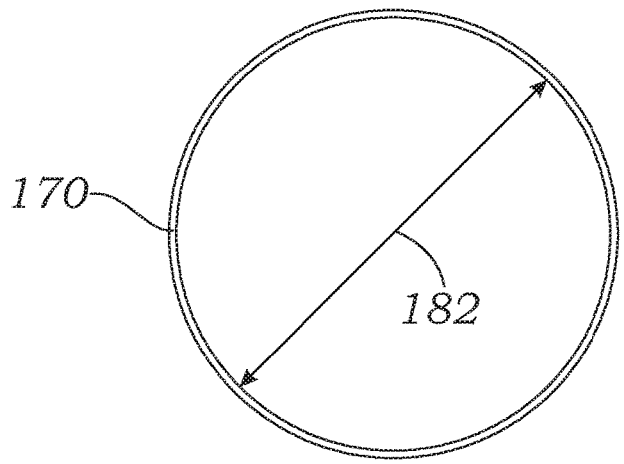
FIGS. 3C-3D depict top and side views, respectively, of the support structure of FIGS. 3A-3B after the prosthetic heart valve support structure has been dilated.
Figure 3B:
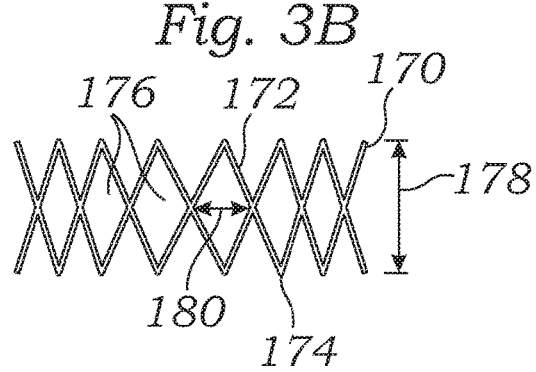
Figure 3D:
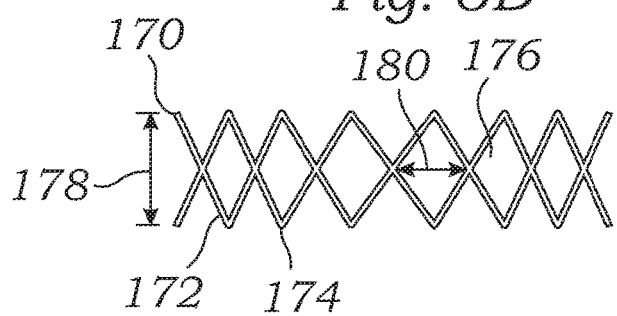

When the prosthetic heart valve 70 of FIGS. 2A-2C is subjected to a dilation force (such as that from a dilation balloon, which may provide pressures of 1 to 12, or more usually 1 and 8, atmospheres), the prosthetic heart valve will be expanded somewhat. The support frame 72 will transition from the generally rigid and/or expansion-resistant configuration of FIGS. 2A-2C to a generally non-rigid and expanded configuration depicted in FIG. 2D. Note that the ring 82, which was generally rigid and/or expansion-resistant, is now generally expanded, and the valve orifice 80 has accordingly been enlarged to a larger inner diameter 78b. The larger inner diameter 78b is configured to receive an expandable prosthetic heart valve therein. The overall result is that the "post-dilation" prosthetic heart valve 70 of FIG. 2D has a generally larger inner diameter circular opening 78b. The actual inner diameters will depend on the particular application, including aspects of the particular patient's heart (e.g., native valve and/or annulus diameter, etc.). As an example, the pre-dilation inner diameter 78a for a mitral valve may be between 22-30 mm, or for an aortic valve 18-28 mm. The post-dilation inner diameter 78b will be larger, and more specifically large enough to accommodate the outer diameter of an expandable prosthetic valve therein.

In some procedures where an expandable prosthetic heart valve is used to replace/repair a previously-deployed prosthetic heart valve, it may be desirable for the expandable prosthetic heart valve to have a deployed (expanded) inner diameter (and corresponding expandable prosthetic heart valve orifice area) approximately equal to or even greater than the pre-dilation inner diameter 78a (and corresponding pre-dilation prosthetic valve orifice area) of the previously-deployed prosthetic heart valve 70. Such consistency between inner diameters/orifice areas, or improvement thereto, can be useful in maintaining proper blood flow, so that the expandable prosthetic heart valve will provide the same or improved blood flow as was provided by the previously-deployed prosthetic heart valve. Note that the term "valve orifice area" refers to the area of the valve orifice when the valve portion is in the fully open configuration (e.g., with the valve leaflets in their fully open configuration so that the effective orifice area is at its maximum size).

For example, Edwards Lifesciences has Sapien™ expandable prosthetic heart valves having outer diameters of 23 and 26 mm, respectively, which have corresponding inner diameters of about 22 and 25 mm, respectively. Accordingly, the post-dilation inner diameter 78b of the (previously-deployed) prosthetic heart valve may be on the order of 23 and 26 mm (respectively) to accommodate such expandable prosthetic heart valves. This corresponds to a post-dilation inner diameter 78b being about 10 to 20% larger than the pre-dilation inner diameter 78a. Accordingly, embodiments of the invention include a prosthetic heart valve having a post-dilation inner diameter 78b that is about 10, 15, or 20%, or between 5-25%, 10-20%, or 13-17% of the pre-dilation inner diameter 78a.

Note that the invention is not limited to the above differences between pre- and post-dilation inner diameters. For example, there may be applications where much smaller and/or much larger post-dilation inner diameters may be required. In some cases an expandable prosthetic heart valve will have an outer diameter only slightly larger than its inner diameter, so that less expansion of the previously-deployed prosthetic heart valve inner diameter is required in order to accommodate the expandable prosthetic heart valve. In other cases an expandable prosthetic heart valve may have an outer diameter that is much larger than its inner diameter, so that a greater expansion of the previously-deployed prosthetic heart valve inner diameter is necessary to accommodate the expandable prosthetic heart valve. There may also be applications where it may be desirable to deploy an expandable prosthetic heart valve having a smaller or larger inner diameter than was provided by the (previously-deployed and pre-dilation) prosthetic heart valve.

Note that, depending on the particular embodiment, a prosthetic heart valve 70 may return to its pre-dilation inner diameter 78a after being subject to dilation such as from a balloon dilation catheter or other mechanical expander. However, the dilation will have rendered the "post-dilation" prosthetic heart valve 70 into a generally non-rigid and/or expansion-friendly configuration, so that the "post-dilation" prosthetic heart valve 70 will be forced with relative ease into a larger diameter (such as 78b) when an expandable (e.g., balloon-expandable, self-expanding, etc.) prosthetic heart valve is deployed within the valve orifice 80 of the prosthetic heart valve 70.

FIGS. 3A-3D depict a further embodiment of a support structure 90 according to the invention, where expansion sections are formed by a series of interconnected struts 92 connected end-to-end by hinge-like connections 94 to form a zig-zag accordion-like structure having substantially diamond-shaped cells 96. In the non-expanded (pre-dilation) configuration (depicted in FIGS. 3A and 3B), the substantially diamond-shaped cells 96 are at a maximum height 98 and a minimum width 100, and the structure 90 defines a minimum sized inner diameter 102. In the expanded (post-dilation) configuration (depicted in FIGS. 3C and 3D), the interconnected struts 92 have rotated at the hinge-like connections 94, and the substantially diamond-shaped cells 96 have thus been stretched sideways and are at a minimum height 98 and a maximum width 100. The expanded structure 90 defines a maximum sized inner diameter 102. The support structure 90 is desirably plastically-expandable so as to initially resist expansion after implant and when subjected to normal anatomical expansion pressures. When the time comes to implant a replacement valve within the prosthetic valve having the support structure 90, outward balloon or other mechanical-expander forces cause plastic deformation of the interconnected struts 92, typically at the hinge-like connections 94. The balloon or mechanical expansion forces can be done separately from implantation of a subsequent valve, or expansion of the subsequently-implanted valve can simultaneously expand the support structure 90.

Figure 4A:
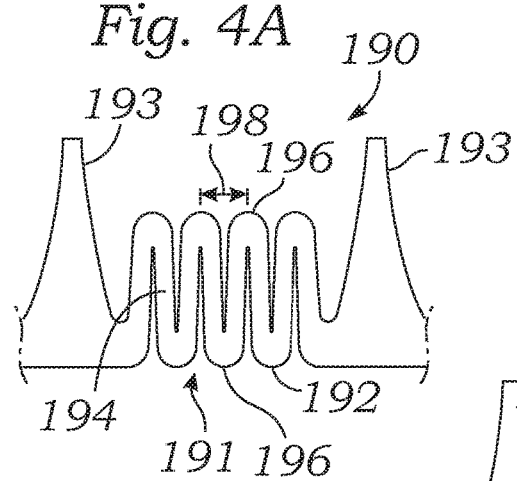
FIGS. 4A-4B depict side views, pre-dilation and post-dilation, respectively, of a prosthetic heart valve support structure according to an embodiment of the invention.
Figure 4B:
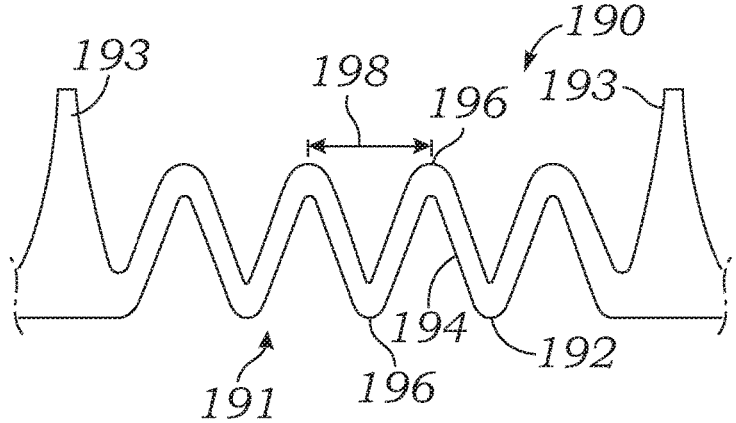

FIGS. 4A-4B depict a further embodiment of a support structure 110 according to the invention, where expansion sections 111 extend between commissural supports 113. The expansion sections 111 are formed by a generally zig-zag or sinusoidal structure 112 formed by a series segments 114 secured at peaks 116 in a serpentine pattern. In the non-expanded (pre-dilation) configuration of FIG. 4A, the zig-zag segments 114 are compressed closely together, with minimal distances 118 between adjacent peaks 116 (and may even have adjacent segments 114 contacting each other edge-to-edge and thus preventing inward compression of the structure to a smaller diameter). In such a configuration, the support structure 110 will have a minimal (unexpanded) diameter. In the expanded (post-dilation) configuration of FIG. 4B, the sinusoidal/zig-zags are pulled into a less compressed configuration, with the adjacent peaks 116 and segments 114 are spaced apart from each other, with maximum distances 118 between adjacent peaks 116 and according a maximum diameter for the support structure 110.

In embodiments of the invention, such as that depicted in FIGS. 3A-4B, the geometry and materials of the structure may be configured so that certain loads (e.g., compressive and/or expansive pressures up to 1 or 2 or even 3 atmospheres) will keep the material in its elastic region, so that it may expand and/or compress slightly when subjected to relatively small compressive and/or expansive loads experienced under normal cardiac cycling, but will return to its original shape once such loads are removed. The geometry and materials of the structure may be configured so that after a certain load is reached (such as 2, 3, 4, 5, or 6 atmospheres), plastic deformation will occur with permanent radial expansion. With such plastic deformation, individual elements may "lock out" and thus prevent further radial dilation of the structure. In general, the various valve support structures herein are configured to expand post-implant from an outward dilatory force from within the support structure larger than forces associated with normal use, i.e., forces associated with the movement of the native annulus during cardiac cycling.

The present application discloses specific modifications to existing surgical valves that enable manufacturers to rapidly produce a valve which accommodates valve-in-valve (ViV) procedures. Specifically, the present application contemplates retrofitting or modifying components within existing surgical valves to enable post-implant expansion. Not only does this convert any proven surgical valve for use in a ViV procedure, but it also reduces design and manufacturing work.

FIGS. 5A-5D are perspective and exploded views of an exemplary prosthetic heart valve 130 of the prior art oriented around a flow axis 132. The heart valve 130 comprises a plurality (typically three) of flexible leaflets 134 supported partly by an undulating wireform 136 as well as by a structural stent 138. The wireform 136 may be formed from a suitably elastic metal, such as a Co—Cr—Ni alloy like Elgiloy™, while the structural stent 138 may be metallic, plastic, or a combination of the two. As seen in FIG. 5B, outer tabs 140 of adjacent leaflets 134 wrap around a portion of the structural stent 138 at so-called commissures of the valve that project in an outflow direction along the flow axis 132. A soft sealing or sewing ring 142 circumscribes an inflow end of the prosthetic heart valve 130 and is typically used to secure the valve to a native annulus such as with sutures. The wireform 136 and structural stent 138 are visible in the figures, but are normally covered with a polyester fabric to facilitate assembly and reduce direct blood exposure after implant.

FIGS. 5C and 5D show the inner structural stent 138 in both assembled and exploded views. Although the general characteristics of the prosthetic heart valve 130 as seen in FIGS. 5A and 5B may be utilized in a number of different prosthetic heart valves, the illustrated structural stent 138 is that used in a particular heart valve; namely, pericardial heart valves manufactured by Edwards Lifesciences of Irvine, Calif. For example, the Perimount™ line of heart valves that utilize pericardial leaflets 134 features an inner stent 138 much like that shown in FIGS. 5C and 5D. In particular, the stent 138 comprises an assembly of two concentric bands—an outer band 144 surrounding an inner band 145. The bands 144, 145 are relatively thin in a radial dimension as compared to an axial dimension, and both have coincident lower edges that undulate axially up and down around the circumference. The outer band 144 exhibits three truncated peaks between three downwardly curved valleys, while the inner band 145 has generally the same shape but also extends upward at commissure posts 146. The downwardly curved valleys are typically termed cusps 148, as seen in FIG. 5C.

In the exemplary Perimount™ valves, the outer band 144 is metallic and is formed from an elongated strip of metal bent to the generally circular shape and welded as at 150. In contrast, the outer band 145 is formed of a biocompatible polymer such as polyester (PET) or Delrin™ which may be molded, and also may be formed as a strip and bent circular and welded (not shown). Both the outer and inner bands 144, 145 feature a series of through holes that register with each other so that the assembly can be sewn together, as schematically illustrated in FIG. 5C. The wireform 136 and the commissure posts 146 of the inner band 145 provide flexibility to the commissures of the valve which helps reduce stress on the bioprosthetic material of the leaflets 134. However, the inflow end or base of the valve 130 surrounded by the sewing ring 142 comprises the relatively rigid circular portions of the structural stent 138. The combination of the metallic outer and plastic inner bands and 144, 145 presents a relatively dimensionally stable circumferential base to the valve, which is beneficial for conventional use. However, the same characteristics of the structural stent 138 that provide good stability for the surgical valve resist post-implant expansion of the valve. Consequently, the present application contemplates a variety of modifications to the structural stent 138 to facilitate expansion thereof.

FIGS. 6A-6B, 7A-7B, and 8A-8B are perspective, assembled and exploded views of three different embodiments of replacement structural bands for the prior art prosthetic surgical heart valve 130 shown in FIG. 5A that enables the heart valve to expand post-implementation. One advantage of modifying the structural bands from the valve 130 in FIG. 5A to expand is that the band is somewhat circumferentially decoupled from the leaflets 134. That is, when the valve expands, the perimeter edges of the leaflets 134 remain essentially unstretched since they are attached to the wireform 136, which expands concurrently by hinging action at the commissure tips. As a consequence, the leaflets 134 do not need to be significantly stretched to expand our valves, potentially making the valve easier to expand, especially if the leaflets are calcified and not amenable to distension. Desirably, therefore, the present application embodies a valve that can be expanded without needing to significantly stretch the leaflets.

In a first embodiment, FIGS. 6A-6B illustrate a structural stent 154 comprising an inner band 156 concentrically positioned within an outer band 158. The shapes of the inner band 156 and outer band 158 are the same as that shown for the corresponding bands 144, 145 in FIGS. 5C-5D. In contrast to the relatively rigid bands of the prior art, both bands 156, 158 are modified to enable expansion post-implantation. In this embodiment, the inner band 156 features a plurality of break points such as notches 160 formed around the circumference that reduce the cross sectional area of the band at that point to a relatively small magnitude which can be broken or stretched with the application of sufficient outward expansion force from within. For example, a balloon used to expand a secondary prosthetic valve within the surgical valve may provide sufficient outward force to cause the inner band 156 to rupture or stretch at the notches 160. The material of the inner band 156 may be relatively brittle so that excessive tensile forces cause the notches 160 to break, or the material can be more ductile which permits the notches 160 to plastically stretch in the manner of taffy.

In the illustrated embodiment, there are three notches 160 spaced evenly around the band 156 at the center of each cusp thereof. Additionally, the outer band 158 includes a plurality of accordion-like sections 162 generally extending around the cusp portions thereof and separated by small plates 164 at the truncated peaks of the band. The plates 164 enabled fixation of the outer band 158 at fixed nodes around the inner band 156, such as by using through holes that register for passage of sutures. Expansion of the combined structural stent 154 eventually ruptures or stretches the inner band 154 at one or more of the notches 160, enabling further expansion of the assembly because of the accordion-like sections 162. These sections 162 are desirably formed of a plastically-expandable material such as stainless steel that assumes the larger shape upon expansion, but depending on other aspects of the valve in which the band 158 is used, they may be simply flexible. The sections 162 are shown as repeating diamond-shaped struts connected at their middle corners.

FIGS. 7A-7B and 8A-8B are similarly constructed with alternative expandable segments within the outer stents. For example, FIGS. 7A-7B illustrate a structural stent 166 comprising an inner band 168 concentrically positioned within an outer band 170. The inner band 166 has notches to permit it to break open or stretch from outward expansion. The outer band 168 features expandable segments including a plurality of connected struts in the shape of hexagons. Mid-cusp hexagons 174 are somewhat longer than the remaining hexagons so that greater expansion occurs between the middle of the cusps and the commissures. Again, plates 176 having through holes are positioned at the commissures between each two expandable segments and provide points at which to anchor the inner band 166 to the outer band 168. The structural stent 178 in FIGS. 8A-8B has a similar inner band 180 and a modified outer band 182 with zig-zag shaped struts forming expandable segments 184. Once again, small plates 186 at the commissures of the outer band 182 provide fixed nodes, if you will, for connection to the inner band 180.

FIGS. 9A-9B illustrate an alternative structural stent 190 that can be substituted into the prior art prosthetic heart valve 130 of FIG. 5A to enable post-implantation expansion thereof. The stent 190 comprises an inner band 192 and a concentric outer band 194, as before. The inner band 192 features the upstanding commissures 195 and a plurality of cusps each with multiple expandable segments 196. The outer band 194 has cusps with centered expandable segments 198 and truncated commissures 200 shaped to match a portion of the commissures 195 of the inner band 192. The expandable segments 196 are located along the cusps of the inner band 192 so as to register with solid wall portions of the outer band 194. In this way, the combined bands 192, 194 as seen in FIG. 9A has no holes therethrough, except at aligned suture holes 201 at the commissures.

In the illustrated embodiment, the expandable segments 196, 198 on the two bands each comprise a pair of bent struts that connect upper and lower corners of the adjacent solid wall portions across gaps therebetween. The two struts are bent axially toward each other and will straighten out to extend straight across the gaps when an outward force is applied to the respective band, thus increasing the band diameter. Again, the material may be plastically-deformable so as to assume a new shape when expanded, or may be simply elastic and permit expansion. Also, one of the bands may be plastically-deformable such as stainless steel and the other plastic which merely expands along with the metal band and possesses some small amount of recoil.

FIG. 10 is a still further alternative molded structural stent 202 for substitution into the prior art prosthetic heart valve 130 of FIG. 5A. In this embodiment, an outer "band" 204 concentrically surrounds an inner "band" 206, the two bands actually being molded together and not being separable. The continuous inflow (lower) end of the stent 202 includes the aforementioned alternating cusps and commissures, and the two "bands" 204, 206 have upper and lower notches 208 at the cusp midpoints to enable the stent to break or stretch and expand from an outward force. More particular, the cross-section of the stent 202 at the notches 208 is sufficiently large to maintain the shape of the valve during normal use in a surgical valve, but is small enough to easily break when a balloon, for example, is expanded within the valve of which the stent 202 is a part. Through holes 210 are desirably provided along the stent commissures to permit connection to surrounding structures, such as leaflets, a wireform, or a sewing ring.

It should be noted again that the various expandable segments disclosed herein can be substituted into any of the stents or stent bands shown. For instance, the notches 208 in FIG. 10 could be replaced with any of the expandable segments disclosed, such as the bent struts of the expandable segments 196, 198 shown in FIG. 9B. Also, although notches 208 are shown at the middle of each cusp of the stent 202, only one break point could be provided, as shown below, or the notches 208 could be placed at locations other than mid-cusp. The reader will understand that numerous configurations and combinations are possible.

Figure 11A:
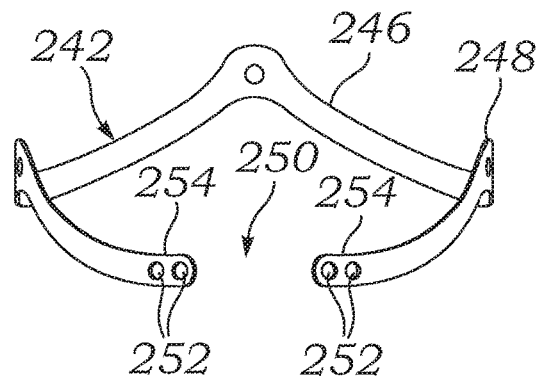
FIG. 11A depicts a side view of a prosthetic heart valve support band according to an embodiment of the invention.
Figure 11B:
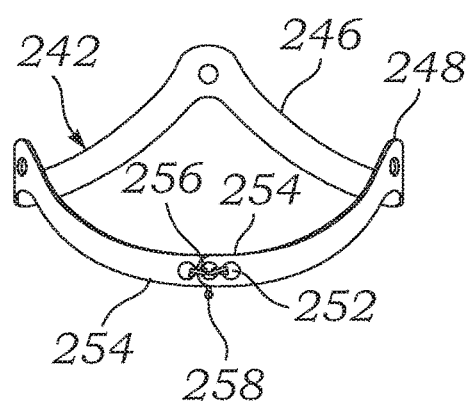
FIGS. 11B and 11C depict side and perspective (close-up) views, respectively, of the prosthetic heart valve support band of FIG. 11A with suture(s) securing the free ends together.
Figure 11C:
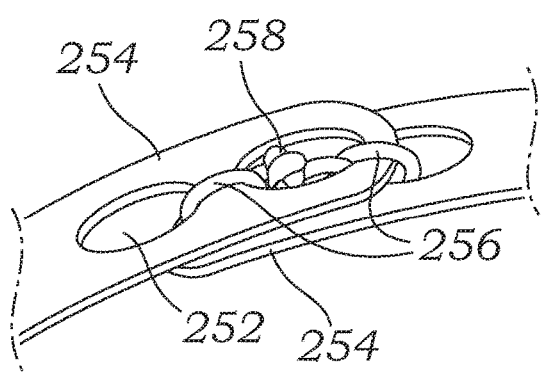
Figure 11D:
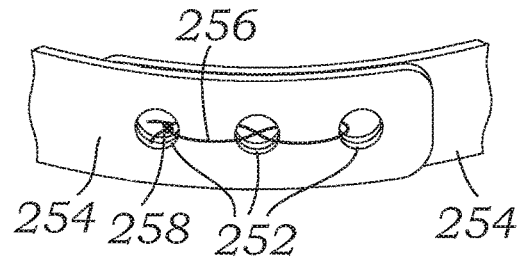
FIG. 11D shows an enlarged side view of the support band of FIG. 11A with an alternative configuration of free ends secured together.

FIGS. 11A-11F depict another composite support stent 240 for a prosthetic heart valve formed form an inner or first band 242 and an outer or second band 244. With reference to FIGS. 11A-11B, the first band 242 comprises a single, unitary piece of material forming a substantially circular support structure having 3 curved segments 246 connected at commissural points 248. One of the curved segments 246 has a break 250 in the middle thereof with holes 252 drilled in the free ends 254 on either side of the break 250. As shown in FIGS. 11B and 11C, when assembled the free ends 254 are joined together via a suture 256, such as silk 4-0 suture, passed through the holes 252 and secured in a knot 258. Note that the knot 258 may be formed on the radial exterior of the first support structure to help maintain a smooth interior surface thereof. FIG. 11D shows an enlarged side view of the outer support band 242 of FIG. 11A with an alternative configuration of free ends 254 secured together. In particular, each free end 254 has a series of holes 252, three as illustrated, that align with the same number of holes in the other free end. A length of suture 256 or other such filament may be interlaced through the holes 252 such as in a "FIG. 8" configuration, and then tied off at knot 258. In testing, the arrangement in FIG. 11D produced an average breaking pressure of about 2.58 atm, with a range of between 2.25 to 3 atm.

The suture/hole combination forms a weakened spot on the first band 242, where the suture 256 will break before the remaining parts of the support portion will fail when the support portion is subjected to a dilation force. Note that other techniques and assemblies may be used to form the weakened portions, such as spot welds, thinned sections, and other methods such as those disclosed herein for other embodiments. In this particular embodiment depicted in FIGS. 11A-11B, the first band 242 is desirably formed from a metal such as stainless steel or cobalt-chromium (Co—Cr).

Figure 11E:
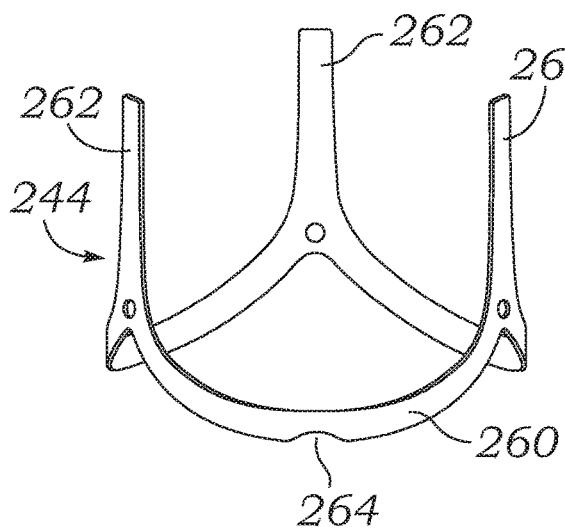
FIG. 11E depicts a side view of another prosthetic heart valve support band for use with the support band of FIG. 11A.

FIG. 11E depicts a second support band 244 according to an embodiment of the invention. The support band 244 comprises a single, unitary piece of a material, such as a polymer like polyester, forming a substantially circular support structure having 3 curved segments 260 connected at commissural supports 262. One of the curved segments 260 has a thinned section 264 to form a weakened section that will fail prior to the rest of the structure when subjected to a sufficient dilatation force. Note that other methods of forming the weakened section are also within the scope of the invention, such as using spot welds, sonic welds, sutures, and/or thinned/weakened areas.

Figure 11F:
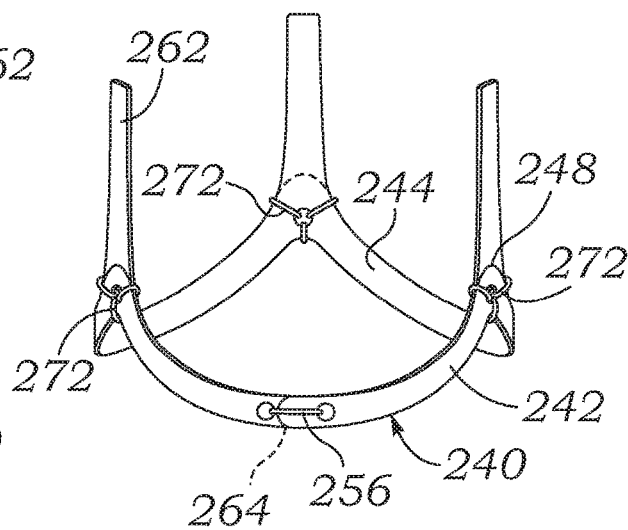
FIG. 11F depicts a side view of a prosthetic heart valve structure formed from securing the first prosthetic heart valve support band in FIG. 11A and the second prosthetic heart valve support band in FIG. 11E into a composite structure.
Figure 11H:
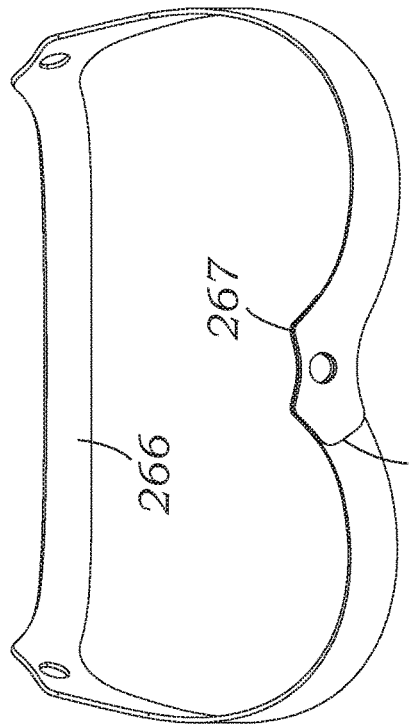
FIGS. 11G-11J show a variation on the first and second prosthetic heart valve support bands shown in FIGS. 11A-11F.

FIG. 11F depicts a composite prosthetic heart valve support stent 240 formed from securing the first prosthetic heart valve support band 242 and the second prosthetic heart valve support band 244 into a composite structure. The support portions 242, 244 may be secured together via various techniques, such as welds, adhesives, etc. In the particular embodiment depicted, the support portions 242, 244 are secured together via sutures 272 adjacent the commissural points 248 and commissural supports 262 of the support portions 242, 244. Note that in this particular embodiment, the first support band 242 is positioned concentrically within the second support band 244, and the weakened area 264 of the second band 244 is positioned adjacent the suture 256 over the overlapping ends 254 in the first band 242, so that when the second support band 244 and the first support band 242 break due to dilation the respective breaks will be at the same position around the circumference of the support stent 240.

In an alternate embodiment, the weakened area 264 might be circumferentially displaced from the suture 256 and overlapping ends 254, such as being position anywhere from a few degrees to being completely opposite (i.e., 180 degrees) away around the circumference. The weakened area 264 of the second support band 244 may be circumferentially displaced from the suture 256/overlapping ends 254, but still positioned between the same pair of commissure posts 262 between which the suture 256 overlapping ends 254 are positioned. Note that one or both of the first and second support bands 242, 244 may have multiple weakened areas designed to fail when subjected to sufficient radial pressure. For example, the first support band 242 may have a single weakened area in the form of the suture 256 and overlapping ends 254, with the second support band 244 having multiple weakened areas 264 (such as 3 different weakened areas, with one weakened area being positioned between each pair of commissural posts 262). The offsetting of the weakened areas of the first and second support portions may improve the structural integrity of the structure post-dilation.

Figure 11J:
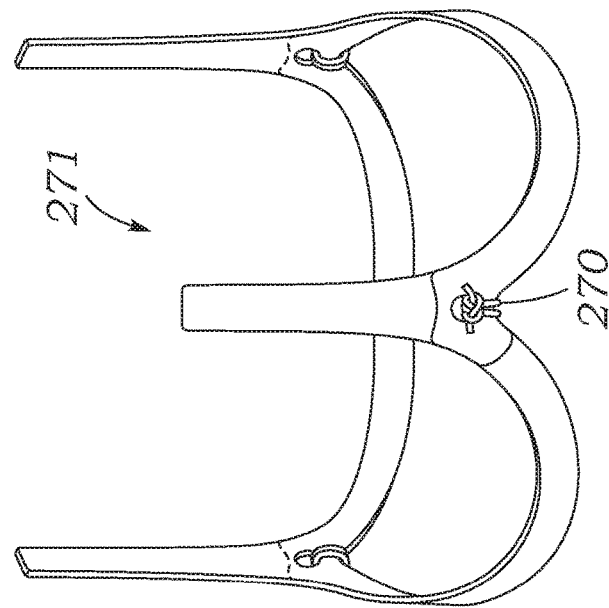
Figure 11G:
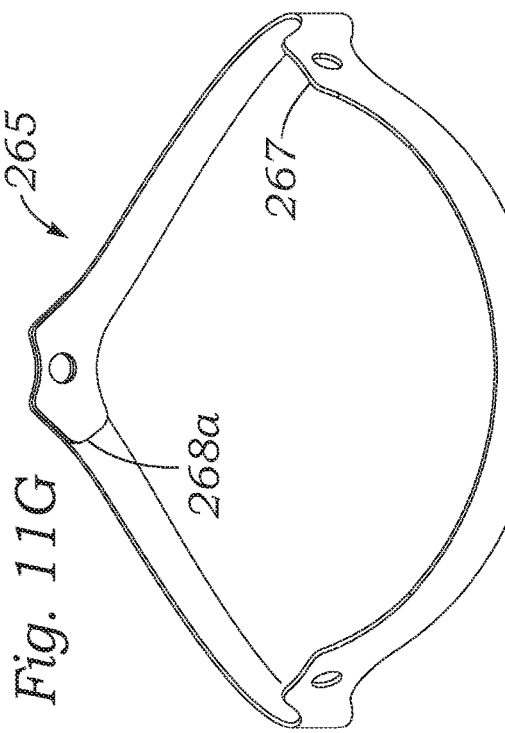
Figure 11I:
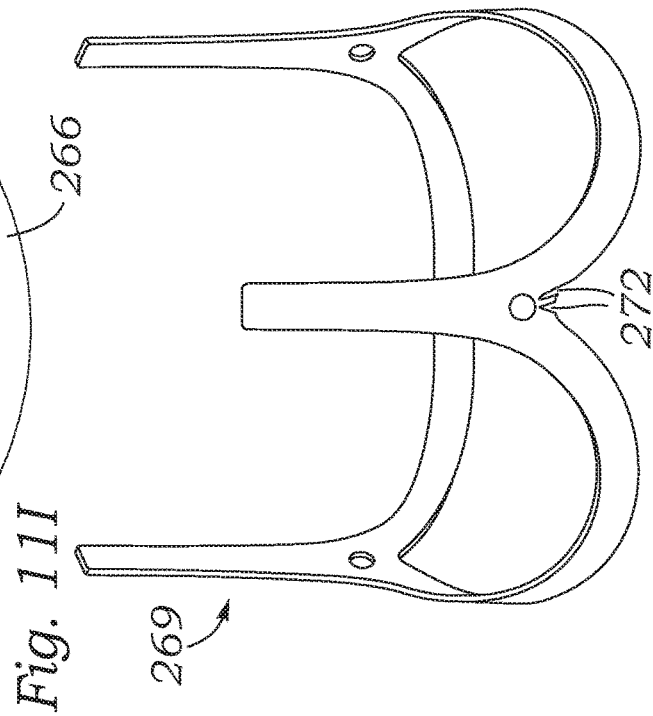

FIGS. 11G-11J show a variation on the first and second prosthetic heart valve support bands shown in FIGS. 11A-11F in which an outer or first band 265 includes the aforementioned undulating cusps 266 and truncated commissures 267, and is formed from a single element having two free ends 268a, 268b adjacent one of the commissures rather than at a cusp. When registered with an inner or second band 269, sutures 270 may be used to secure the registered commissure regions together such as by using aligned holes to form a composite stent 271, as seen in FIG. 11J. After assembly into a prosthetic heart valve, such as the valve 130 of FIG. 5A, the stent 271 initially provides good circumferential support for the valve and resists both compression or expansion from natural cardiac cycling forces. At some future date, if the valve requires replacement, a balloon or other mechanical expander may be advanced to the annulus and inserted into the orifice defined within the valve. The sutures 270 at the valve commissure having the free ends 268a, 268b will ultimately break from the outward expansion force of the balloon, permitting the valve to expand. Preferably the inner band 269 is made of a polymer that possesses relatively little resistance to the balloon forces, and eventually will stretch and even rupture. To facilitate this process, one or more small notches 272 such as seen in FIG. 11I may be provided at the bottom edge of the commissure of the inner band 269. Locating the break point at one of the commissures has an added benefit of allowing the valve to expand without changing much the circumferential spacing of the commissure posts. That is, in valves having three posts (and three leaflets) spaced apart 120°, for example, the lower cusps 266 of the outer band 265 will slide apart slightly, as will the cusp portions of the inner band 269, but the upstanding posts will remain essentially in the same position. The expansion magnitude is not so great as to distort the structure, and so the upstanding posts of the primary valve will remain 120° apart so as not to interfere with the functioning of a secondary valve or affect the ability of the valve sinuses (in aortic valves) to move and facilitate flow.

FIG. 11J shows a different stitch used with the sutures 270 holding the two bands 265, 269 together (relative to the more robust "Y-stitch" seen in FIG. 11F, for example). The sutures 270 are instead only looped through the aligned holes and around the lower edge of the two bands 265, 269 to form an "I-stitch." This facilitates expansion of the combined stent 271, as the sutures 270 permit relative movement/pivoting of the two bands 265, 269. In testing, the I-stitch arrangement in FIG. 11J produced an average breaking pressure of about 3.08 atm, with a range of between 2.75 to 3.5 atm.

FIGS. 11G-11J also illustrate an outer band 265 that is modified so as to be readily identifiable in the body, post-implant. As mentioned elsewhere, one advantageous configuration disclosed herein is a slight modification of an existing commercial surgical prosthetic heart valve to be expandable, which reduces development costs as well as generally limiting the need for new assembly procedures. However, it is desirable to provide a simple and definitive indication to a surgeon years later after implant that the particular valve has the capacity for expansion. Therefore, the typically metal band 265 may be slightly modified to have a unique characteristic feature visible under external imaging techniques (e.g., X-ray, CT scan, fluoroscopy, transthoracic echocardiography (TTE), or transesophageal echocardiography (TEE) that signifies its type. In FIGS. 11G-11J, the outer band 265 has small depressions or concavities formed at the peaks of the truncated commissures 267, which is distinct from the regular convex peaks such as those seen at the commissures of the band 144 in the prior art valve of FIGS. 5A-5D. This alteration takes advantage of the relatively large surface area of the outer band 265 in the commissure areas without affecting valve function.

The particular metal used for the outer band 265 in the prior art is a Cr—CO alloy, which is readily visible under imaging, and thus an identifiable shape or pattern on the band can indicate the capacity for expansion. Other embodiments for identifying the band 265 as being expandable, as opposed to a non-expandable "regular" band, is to utilize sutures 270 that are highly visible with external imaging techniques. For instance, the sutures 270 could be radiopaque. Another possibility is to use the element tantalum as a marker, either as a spot marker on the band 265, a wire connected thereto or to another part of the valve, or the like. Tantalum is highly inert and also radiopaque, and could be spot welded to the metal band 265 to indicate a valve series or type. A still further embodiment is to seed a permeable element of the valve with a radiopaque compound, such as adding barium sulfate to the sewing ring surrounding the band 265. Various other marking strategies are contemplated.

Figure 11K:
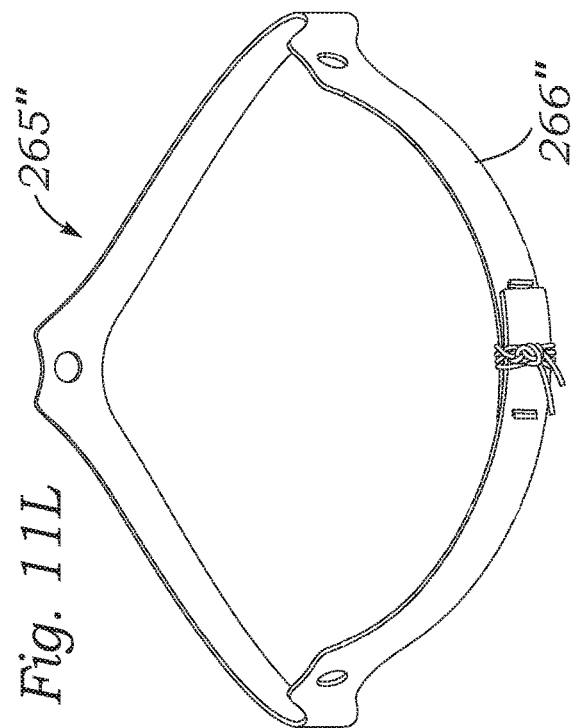
FIGS. 11K-11N show further variations on the first prosthetic heart valve support band.
Figure 11N:
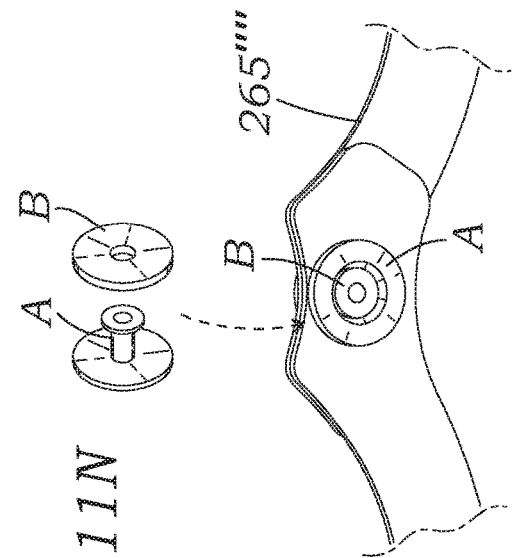
Figure 11L:
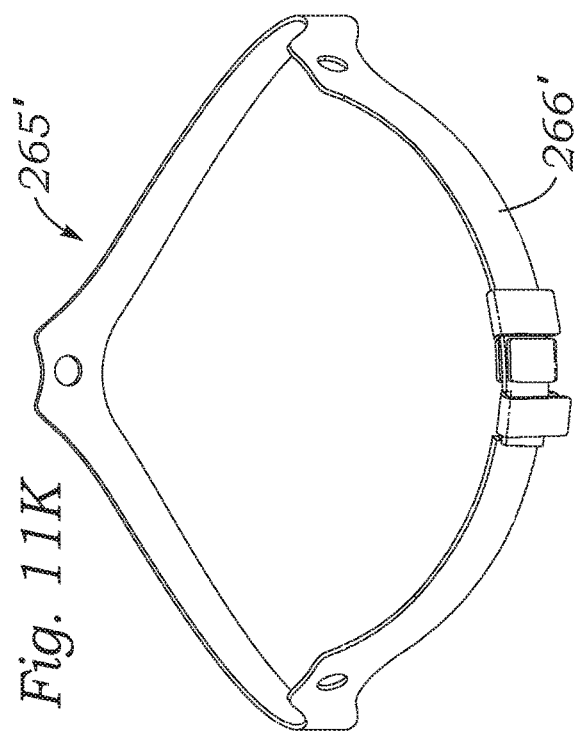
Figure 11M:
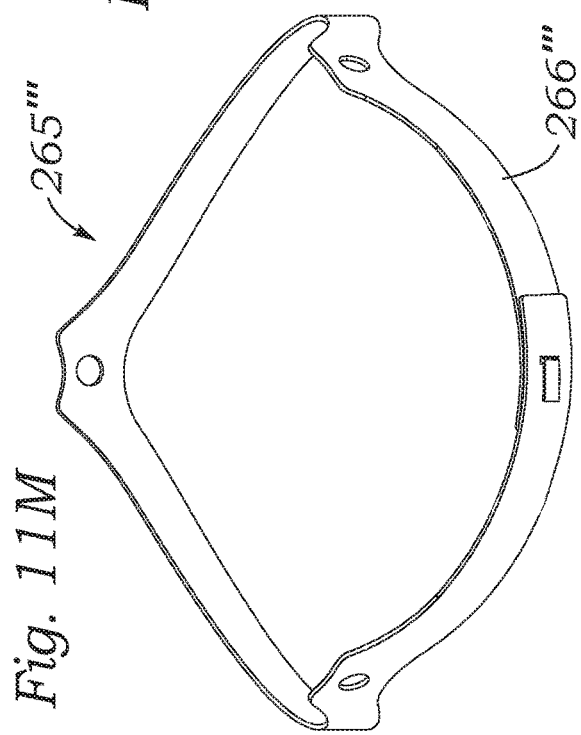

FIGS. 11K-11M show further variations on the first prosthetic heart valve support band 265. A modified outer band 265' in FIG. 11K includes two free ends at one of the cusps 266' that remain aligned with several wrap-around tabs (not numbered). The tabs of one free end that initially extend axially relative to the band axis may be bent around the other free end during assembly. Notches or shoulders on one or the other prevents the band 265' from being compressed, but the arrangement permits expansion, such as with a dilation force within the valve. In testing, the overlapping tab configuration in FIG. 11K produced an average breaking pressure of about 3.17 atm, with a range of between 1 to 5 atm. FIG. 11L shows another modified outer band 265" with the free ends at a cusp 266" that overlap; one radially sliding inside the other. Instead of a flexible sleeve, as in FIGS. 13A-13B below, a suture is wrapped around multiple times, e.g., four, to maintain alignment of the two free ends. Furthermore, small tabs (not numbered) extend radially outward from each free end to present an impediment to compression of the band, but the tabs are positioned and angled such that they do not unduly interfere with expansion of the band 265". When tested for break strength, the configuration in FIG. 11L produced an average breaking pressure of about 3.0 atm, with a range of between 2 to 4.25 atm. FIG. 11M illustrates a still further alternative band 265''' having overlapping free ends at a cusp 266'''. A small tab on the inner free end passes outward through a similar-sized slot in the outer free end, something like a belt buckle. The tab may be shaped like an arrowhead to provide a lock of sorts and prevent its removal from the slot. Again, this limits relative movement of the two free ends to one direction that enables expansion of the band but prevents compression. The break strength for the belt buckle structure in FIG. 11M is between about 6.5 to 8 atm.

Finally, FIG. 11N shows a commissure portion of a still further outer band 265'''' that has a polymer rivet with male part A and female flange B secured through the aligned holes. The rivet A/B may be snap fit together or fused through heating or ultrasonic welding. A variation is a polymer pin or screw that passes through the aligned holes and engages both free ends of the band by swaging the ends, adhesive or with threads. The force needed to separate the ends and expand the band 265" depends on the type of polymer used. One other alternative is to form the rivet A/B of a biodegradable material that will maintain the band together for a period after implant and then dissolve, enabling easy expansion of the band 265". Still further, material from one of the holes may be mechanically deformed into the other hole, such as by swaging, to provide some interference which can be overcome when needed by a dilatory force. Of course, combinations of these structures are also possible, such as combining the belt-buckle tab/slot with the wrap-around tabs.

Figure 12A:
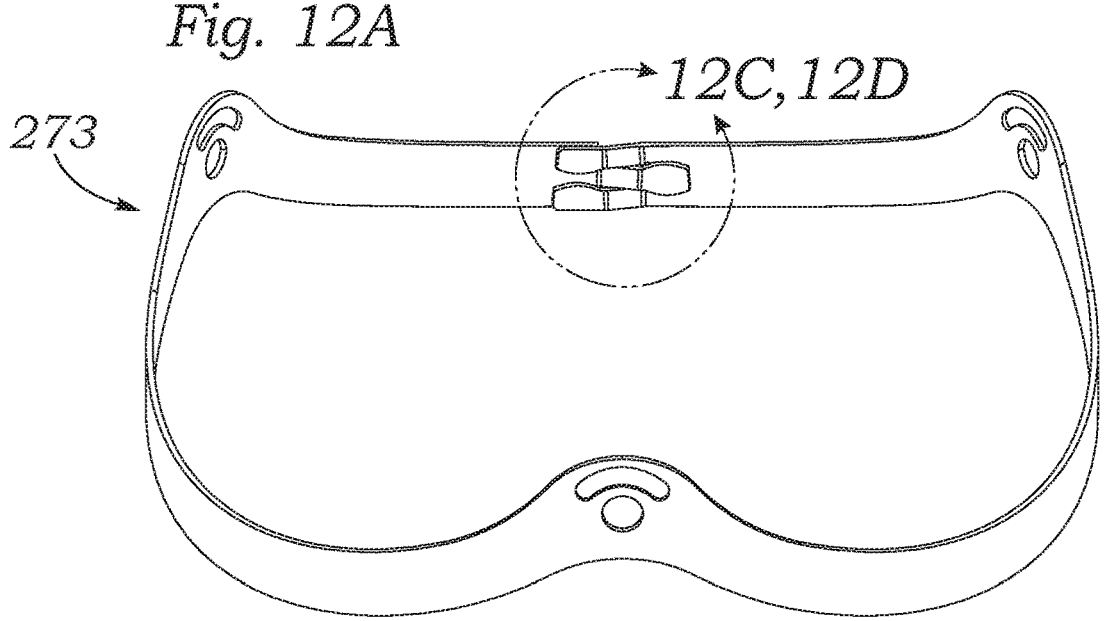
FIGS. 12A and 12B are perspective views of another exemplary prosthetic heart valve support band adapted for post-implant expansion having overlapping free ends with tabs that engage each other.
Figure 12B:
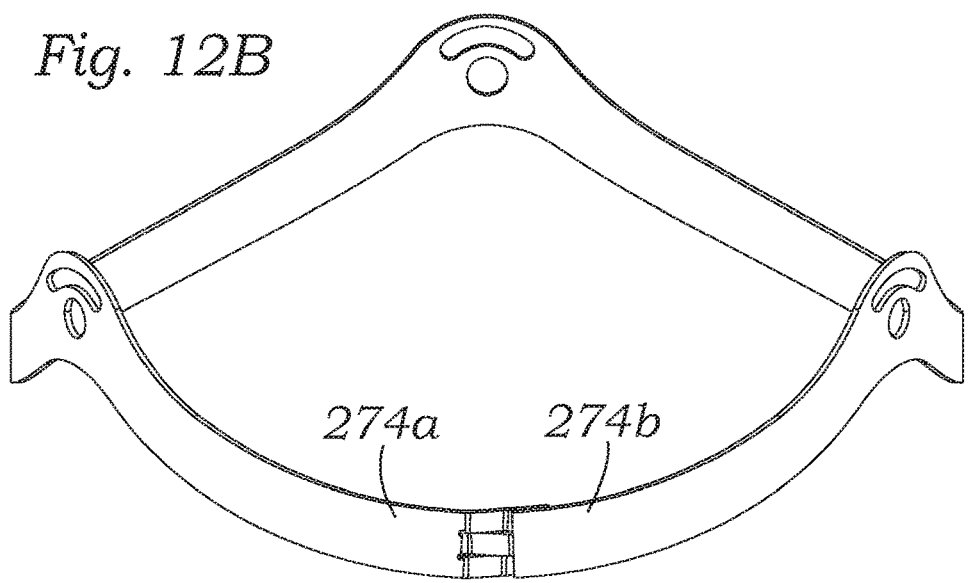
Figure 12C:
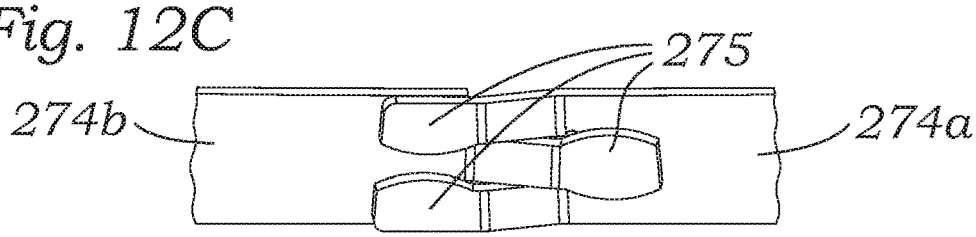
FIGS. 12C and 12D are enlarged views of the overlapping free ends in both constricted and expanded configurations, respectively.
Figure 12D:
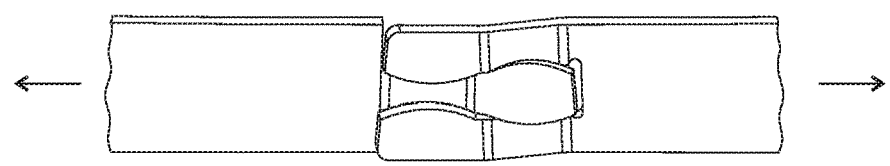

Now with reference to FIGS. 12A-12D, a still further alternative first or outer band 273 is shown that may be used with any of the various expandable heart valves disclosed herein. The band 273 has two free ends 274a, 274b that overlap in the area of one of the cusps of the band. The free ends 274a, 274b include interlaced tabs 275 that permit the two ends to slide away from one another. In the illustrated embodiment, one free end 274a has a pair of tabs 275 that surround a single tab on the other free end 274b. The tabs desirably each include an enlarged head portion and slimmer stem, with the head portions overlapping radially and engaging at a particular outward expansion. The free ends 274a, 274b thus prevent contraction of the band 273 and permit a limited expansion thereof. The expansion requires a relatively low force to cause the free ends 274a, 274b to slide with respect to one another, and the band 273 is desirably coupled with an inner band with a weakened cusps, such as shown at 244 in FIG. 11E. FIGS. 12C and 12D are enlarged views of the overlapping free ends 274a, 274b in both constricted and expanded configurations, though it should be understood that in the expanded configuration the two ends can completely separate. The same interlaced structure may be provided at all three cusps, or at the commissures, though the cusp regions are well suited for the structure. When tested for break strength, the interlaced tabs in FIG. 12A-12B produced an average breaking pressure of about 0.8 atm, with a range of between 0.5 to 1.0 atm.

Furthermore, the illustrated embodiment of interlaced tabs 275 should not be considered limiting, and others are possible. For instance, one free end 274a could have 3 tine-like tabs with two outer ones extending on one side of the other free end 274b while a third middle one is directed to the other side. This permits expansion but prevents contraction. Alternatively, features on the axial edges of the free ends 274a, 274b rather than the circumferential ends could be shaped to engage each other to permit expansion but prevent contraction.

The band 273 in FIGS. 12A-12B is also modified so as to be readily identifiable in the body, post-implant, by external imaging. In particular, an arcuate upwardly convex slot (not numbered) is seen at each commissure, just above the hole used for assembling the band 273 with an inner band (not shown). Again, this readily identifiable hole pattern permits a surgeon contemplating a replacement operation to easily see that a valve-in-valve procedure is a possibility.

Figure 13A:
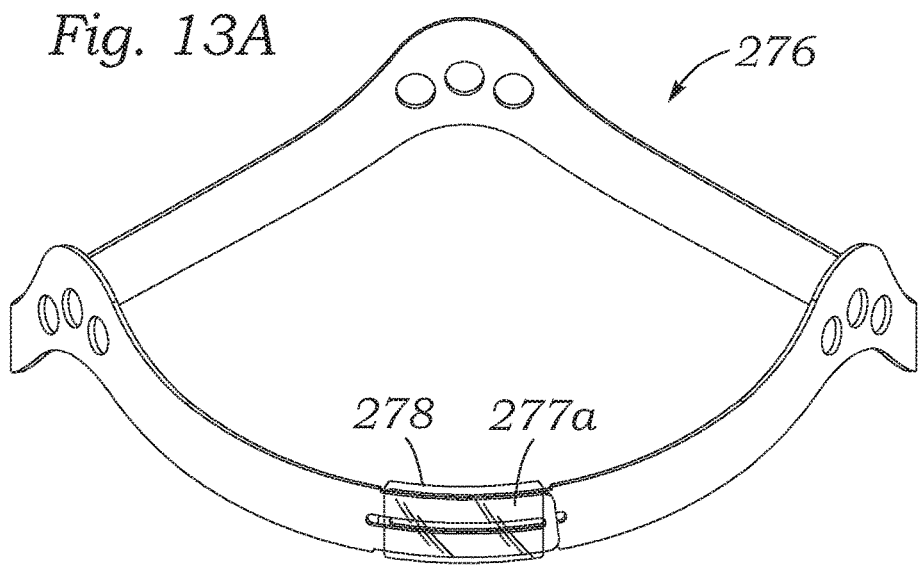
FIGS. 13A and 13B are perspective views of a further prosthetic heart valve support band adapted for post-implant expansion also having overlapping free ends held together by a frictional sleeve.
Figure 13B:
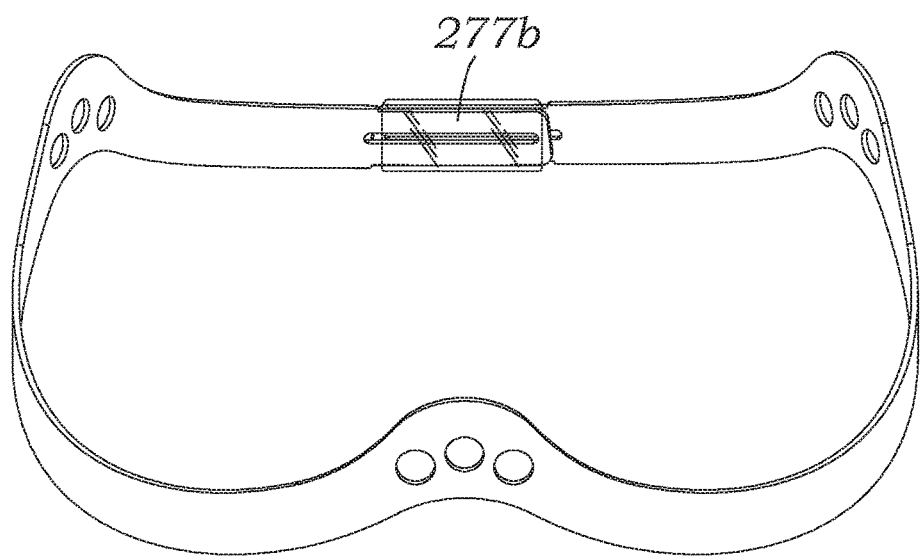
Figure 13C:
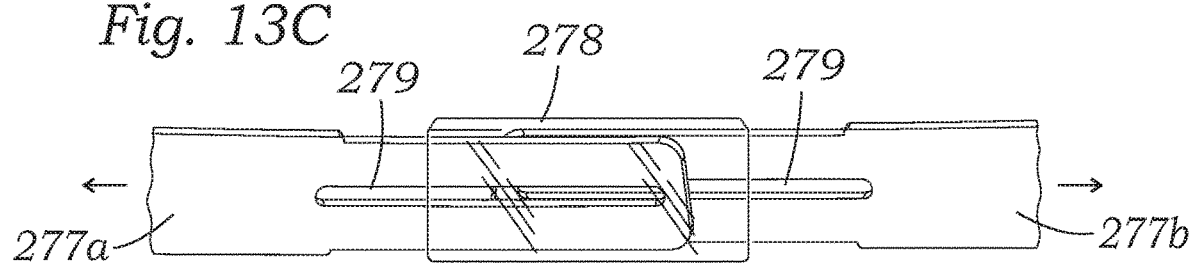
FIG. 13C shows the expansion of the overlapping free ends.

Finally, FIGS. 13A-13C show another "sliding" engagement wherein a first or outer band 276 includes two overlapping free ends 277a, 277b that slide with respect to one another. The free ends 277a, 277b are substantially rectangular in shape and one resides radially within and against the other. A sleeve 278 surrounds the free ends 277a, 277b and holds them radially together. The sleeve 278 desirably comprises polyester (e.g., PET) shrink wrap tubing, or may be an elastic material, such as silicone rubber, and is shown transparent to illustrate the mating free ends 277a, 277b. With reference to the enlargement in FIG. 13C, the two free ends 277a, 277b may slide apart a predetermined distance while still being overlapping. The flexible sleeve 278 provides a minimum amount of friction but generally just serves to maintain alignment of the free ends 277a, 277b. Each of the free ends 277a, 277b further includes a circumferentially-oriented slot 279 that stops short of the terminal ends and provides a pathway for fluid flow. As seen in FIGS. 13A and 13B, the slots 279 extend farther outward from the sleeve 278 so that fluid can always enter the spaced within the sleeve. During storage, the slots 279 permit flow of a fluid between the overlapping free ends 277a, 277b to allow for sterilization. When tested for break strength, the sleeve configuration in FIG. 13A-13B produced an average breaking pressure of about 1.2 atm, with a range of between 0.5 to 2.0 atm. As with the rivet A/B described above, the sleeve 278 may be biodegradable to maintain alignment of the two free ends 277a, 277b for a period after implant and then degrades to permit easy expansion of the band 276.

The band 276 in FIGS. 13A-13B shows a still further identifying trait visible using external imaging and signifying it is expandable. In particular, a pattern of three holes are provided at each commissure. Again, this permits a surgeon contemplating a replacement operation to quickly confirm that a valve-in-valve procedure is a possibility.

Figure 14A:
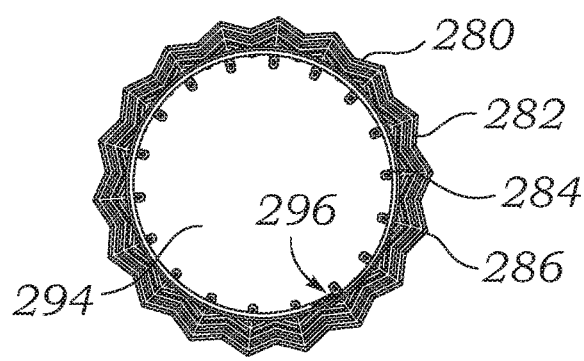
FIGS. 14A and 14B depict top and side views, respectively, of a prosthetic heart valve support structure according to an embodiment of the invention.
Figure 14B:
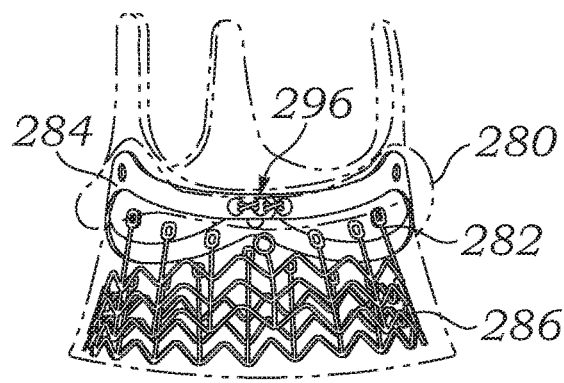
Figure 14C:
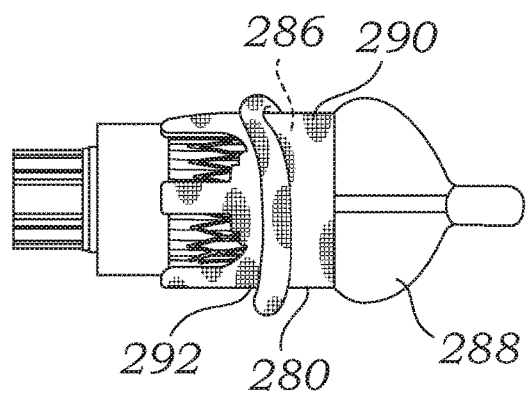
FIGS. 14C and 14D depict side views of a prosthetic heart valve having a support structure as in FIGS. 14A and 14B, with a balloon catheter expanding the expandable skirt but not expanding the main support structure portion.
Figure 14D:
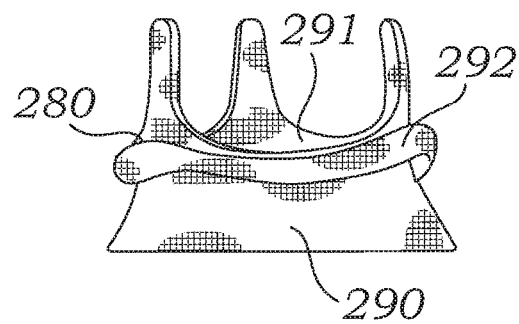
Figure 14E:
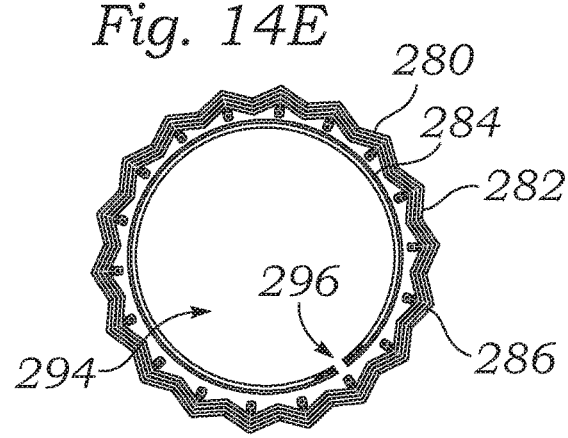
FIGS. 14E and 14F depict top and side views, respectively, of the prosthetic heart valve support structure of FIGS. 14A and 14B after a balloon catheter has radially expanded the main support structure portion into an expanded configuration.
Figure 14F:
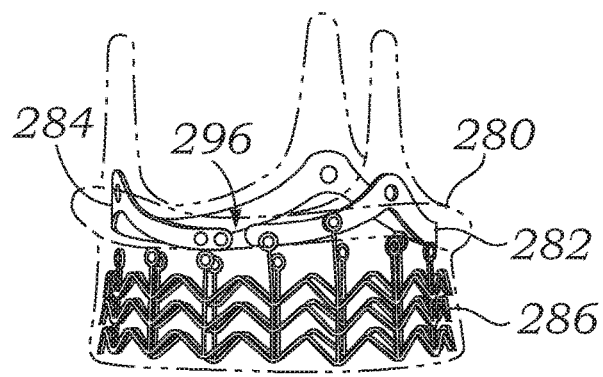

FIGS. 14A and 14B depict a further embodiment of a "hybrid" prosthetic heart valve 280, where an upper support stent 284 (such as the composite stent 240 in FIG. 11E) is joined by a lower frame structure 286. The lower frame structure 286 is radially weaker than the upper support structure 284, and is configured to flare, as seen in FIG. 14B, when subjected to a radially dilating pressure such as that provided by a catheter balloon 288 such as depicted in FIG. 14C. In the embodiment depicted (and seen most clearly in FIGS. 14C-14D), the lower frame structure 286 is covered by a skirt of material 290. The prosthetic heart valve 280 includes valve leaflets (not shown) to control blood flow. The prosthetic heart valve also has a sewing ring 292 as well as the flared lower frame structure 286/skirt 290 to assist in seating the prosthetic heart valve 280 in the desired location (e.g., a native valve annulus in a patient). Details on the initial deployment in a patient of the prosthetic heart valve 280 (with the upper support structure 284 in the unexpanded configuration) are set forth in U.S. Pat. No. 8,308,798, filed Dec. 10, 2009; U.S. Pat. No. 8,348,998, filed Jun. 23, 2010; and U.S. Patent Publication No. 2012/0065729, filed Jun. 23, 2011; the contents of which are expressly incorporated herein by reference.

The prosthetic heart valve 280 is a "hybrid" in that the upper portion is constructed similar to conventional surgical valves, with a relatively stable diameter that is not intended to be compressed or expanded, while the lower frame structure 286 is expandable to help in anchoring the valve in place. One specific commercial prosthetic heart valve that is constructed in this manner is one which is sold in conjunction with the Edwards Intuity™ valve system from Edwards Lifesciences of Irvine, Calif. The Edwards Intuity™ valve system comprises a "hybrid" valve incorporating essentially a surgical Perimount™ valve having a stainless steel lower frame structure. As mentioned, the valve components described above with respect to FIGS. 5A-5D are essentially the same as in the Perimount™ surgical pericardial valve sold by Edwards Lifesciences, and the modifications illustrated in FIGS. 6-14 thus enable conversion of an existing surgical valve into one that is capable of post-implant expansion. Indeed, one especially beneficial aspect of the present application is disclosure of specific modifications to existing commercial surgical valves that enable post-implant expansion. Consequently, the present application contemplates retrofitting or modifying components within existing surgical valves to enable post-implant expansion.

A key feature of the "hybrid" valve embodiment of FIGS. 14A-14F is that the lower frame structure 286 will flare when subjected to a dilation pressure that is insufficient to cause radial expansion of the upper support structure 284, so that a user can deploy the prosthetic heart valve 280 in the patient. For instance, a catheter balloon 288 may be used to achieve the required flaring of the lower frame structure 286, while still preserving the non-expanded nature of the upper support structure 284 in order to maintain the patency of the valve leaflets, as depicted in FIGS. 14A-14B. If the prosthetic heart valve 280 should fail or otherwise need replacing in the future, a balloon catheter can be introduced into the patient, and a pressure sufficient to radially expand the upper support structure 284 (e.g., by causing a failure at a designed weakened area 296), which is also higher than that required to flare the lower frame structure 286 (such as 3 atmospheres or more), may be applied to the prosthetic heart valve 280. With the resulting expansion, depicted in FIGS. 14E and 14F, the entire prosthetic heart valve 280, including the upper support portion 284 and the lower frame structure 286, are radially expanded in order to enlarge the valve orifice 294 to accommodate a new catheter-delivered prosthetic heart valve therein. Note that, post-dilation, the lower frame structure 286 may have little if any flaring, and instead has a generally constant diameter along its length.

Note also that in another embodiment, the balloon 288 may be specially shaped (such as depicted in FIG. 38-40 of related U.S. Patent Publication No. 2012/0065729) so it can be positioned in such a way as to apply radially expansive pressure to the lower frame structure 286 while applying little to no radially expansive pressure to the upper support structure. In such an embodiment, the special shaped balloon for radially expanding just the lower frame structure (e.g., during initial implantation of the prosthetic heart valve 280) could be positioned to apply pressure only to the lower support portion. The special shape balloon could then be expanded to a desired pressure, such as 4-5 atmospheres, with the pressure being applied to expand the lower support portion but not being applied to the upper support portion. At a later time when it is desired to radially expand the upper support structure (e.g., when it is desired to deploy a new valve within the existing valve), a much longer and cylindrical balloon can be used to expand both the upper and lower structures. For example, a cylindrical balloon could be positioned within both the upper and lower structures and inflated to between 4 and 5 atmospheres, thus radially expanding both the upper and the lower structures.

The "hybrid" type of prosthetic heart valve such as shown at 280 in FIGS. 14A-14E is implanted by advancing it into position at the annulus, and then inflating a balloon or other mechanical expander to cause outward flaring of the lower frame structure 286. Although the upper support stent 284 is intended to remain with a constant diameter and only expand later if needed when implanting a second valve directly within, use of a traditional cylindrical balloon can inadvertently expand or distort the upper stent and possibly cause malfunction of the valve. Therefore, the present application contemplates a temporary reinforcing band to prevent any adverse effects to the upper stent from initial balloon expansion, as will be explained.

Figure 15:
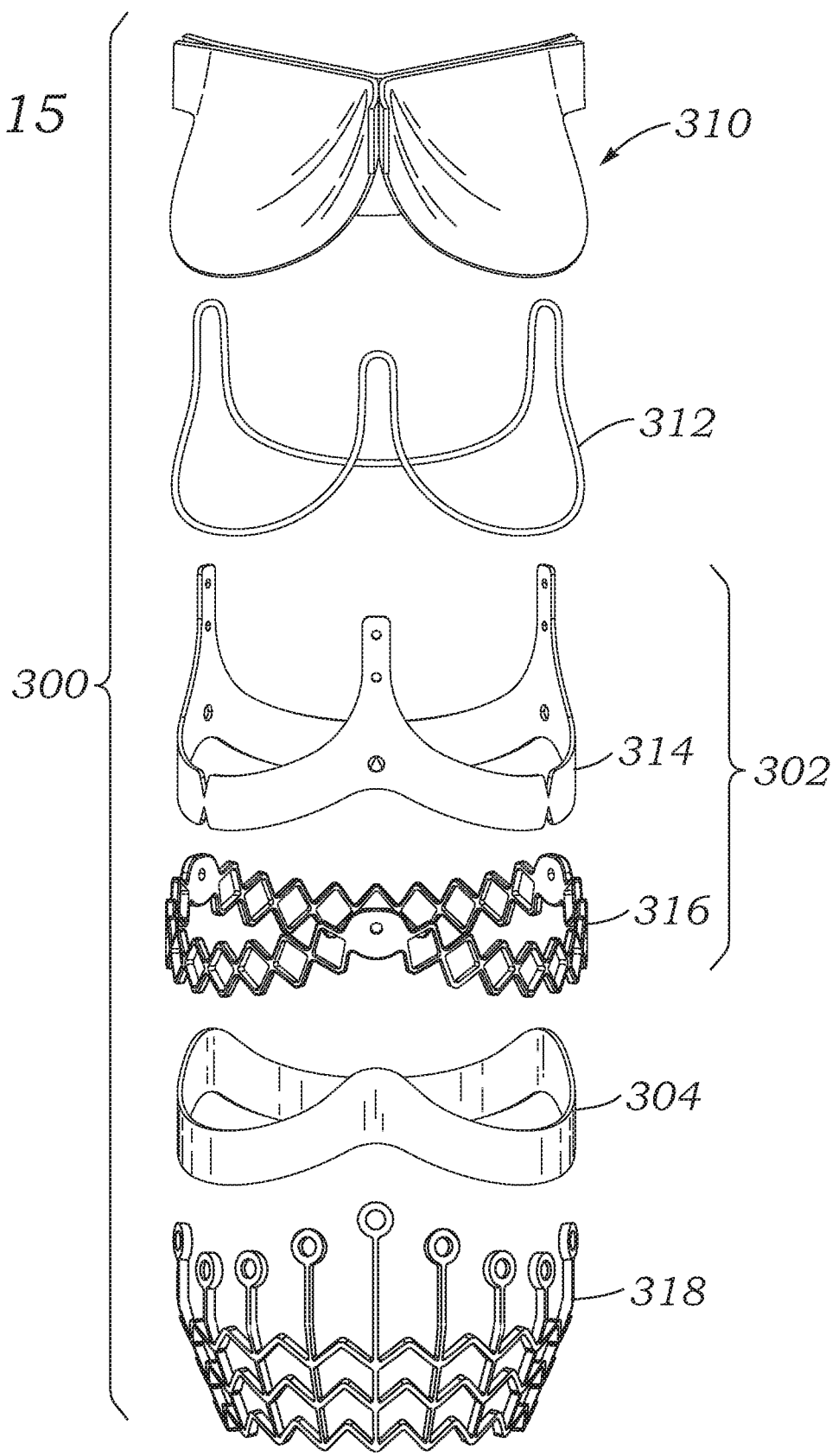
FIG. 15 is an exploded perspective view of an exemplary prosthetic heart valve having an inner structural band combination that permits post-implant expansion, and also includes a reinforcing band that biodegrades after implant.

FIG. 15 is an exploded perspective view of an exemplary "hybrid" prosthetic heart valve 300 having an inner structural band combination 302 that permits post-implant expansion, and also includes a reinforcing band 304 that biodegrades after implant. The main structural components of the heart valve 300 include a plurality of flexible leaflets 310 that are connected to and supported by a continuous undulating wireframe 312, the structural band combination 302 including an inner band 314 and an outer band 316, the reinforcing band 304, and a lower frame structure 318 or anchoring skirt adapted to be expanded once implanted. Various cloth covers and interfaces are not shown for clarity, but are typically used along with sutures to hold the parts together. Again, the flexible leaflets 310 can be a combination of separate leaflets such as bovine pericardial leaflets, or a single bioprosthetic structure such as a porcine valve. The lower frame structure 318 preferably elastically-expandable, such as being made of stainless steel, also maybe self-expanding in certain configurations.

The structural band combination 302 is desirably adapted to enable post-implant expansion, much like the embodiments described above, such as in FIGS. 6-8. Indeed, the inner band 314 and outer band 316 are illustrated the same as those shown in FIGS. 6A-6B, though any of the expandable band combinations can be utilized.

When the components are assembled into the valve 300, it will resemble the valve 280 shown in FIGS. 14A-14F, and also as seen in FIG. 15A which shows the valve during a step of balloon-expanding an anchoring skirt. Once again, this is essentially the same as the heart valve in the Edwards Intuity™ valve system. In addition to the modification that permits post-implant expansion, the new valve 300 features the biodegradable reinforcing band 304. The band 304 may be made sufficiently thin and shaped the same as the outer band 316 so as to be almost unnoticeable in the finished product. Furthermore, various biodegradable materials are known which are routinely included in surgical implants, and thus do not introduce any problematic materials. For example, biodegradable polymers accepted for use include Polyglycolide (PGA), PGA/Polylactide (PLA), PDS— Polydioxanone (PDS), Poly-caprolactone (PCL), Poly(dioxanone), and PGA/Tri-Methylene Carbonate (TMC). Consequently, the modified valve 300 includes relatively small form factor changes from the valve in the Edwards Intuity™ valve system.

As mentioned, FIG. 15A illustrates the hybrid valve 300 isolated from the anatomy but shown at the moment of implantation in the annulus, such as the aortic annulus. The valve 300 is delivered on the distal end of a tubular shaft 330, such as a cannula or catheter. Although not shown, a valve holder may be utilized to couple the valve 300 to the shaft 330. An expansion member 332 such as a balloon is used to expand the anchoring skirt or lower frame structure 318 against the surrounding anatomy. For example, the frame structure 318 may be expanded to a flared shape that generally conforms to the subvalvular terrain in the left ventricle, just below the aortic annulus. Again, the frame structure 318 is desirably plastically expandable, such as being made of stainless steel, and holds its flared shape. Alternatively, the frame structure 318 may be self-expandable, such as being made of Nitinol, which spreads outward upon release and may apply an outward bias against the surrounding tissue. Also, the frame structure 318 may provide the sole means of holding the valve in place, or it may be supplemented with a small number of sutures, clips, or the like evenly distributed around a sealing ring 333 of the valve 300. In any event, the time of the implant process is greatly reduced from prior surgical implants by the elimination of up to 20 knot tying steps when just sutures are used.

The functional portion of the valve 300 defines an orifice diameter d that is relatively stable by virtue of the structural band combination 302, and the valve is intended to function for many years without problem. However, as mentioned, occasionally the valve 300 develops issues such as calcification which reduces its effectiveness. This process may take decades, but eventually a re-operation to fix the valve may become necessary. The modified valve 300 is designed to enable direct expansion of a replacement valve within its orifice, the expansion widening the valve 300 without the need to explant it.

FIG. 15B thus shows a sectional view through the prosthetic heart valve 300 during a post-implantation procedure of implanting a secondary heart valve 334 therewithin. The secondary heart valve 334 is typically delivered on the distal end of a balloon catheter 336 having a balloon around which a plastically-expandable stent 340 of the secondary valve is crimped. One specific valve of this type is the Sapien™ valve sold by Edwards Lifesciences. If the primary valve 300 is implanted in the aortic annulus, the delivery shown is retrograde typically using a transfemoral access procedure, though an antegrade transapical procedure is also contemplated in which case the delivery catheter 336 would be shown entering the valve 300 from the opposite end. Such valves are also known as "transcatheter" valves as they typically are introduced on the end of a catheter.

The strength of the balloon 338 expansion force is sufficient to not only expand the secondary valve 334 outward into contact with the inside of the primary valve 300, but also to outwardly expand the primary valve. As mentioned with reference to FIG. 15, the reinforcing band 304 degrades over time, perhaps after 6 months to a year after implant. Consequently, the inner structural band combination 302 remains to hold the circular shape of the valve 300. Due to the expandable character of the structural band combination 302, the balloon 338 can cause it to outwardly expand to a larger diameter D as shown in FIG. 15B. Additionally, as stated elsewhere herein, any of the structural band configurations disclosed in the application may be utilized or modified for use as the particular structural band combination 302. Preferably the secondary valve 334 expands to have an orifice diameter that matches the original orifice diameter d of the primary valve 300, which may mean a total outward expansion of the primary valve of 2-4 mm, equivalent to one or two valve sizes at 2 mm increments. Preferably, the flow orifice defined by the secondary valve 334 is at least equal to the flow orifice of the primary to 300 so as to avoid any reduction of flow capacity. The plastically-expandable stent 340 is desirably robust enough to hold the primary valve 300 open despite any recoil forces generated by the valve or the surrounding annulus.

Figure 16A:
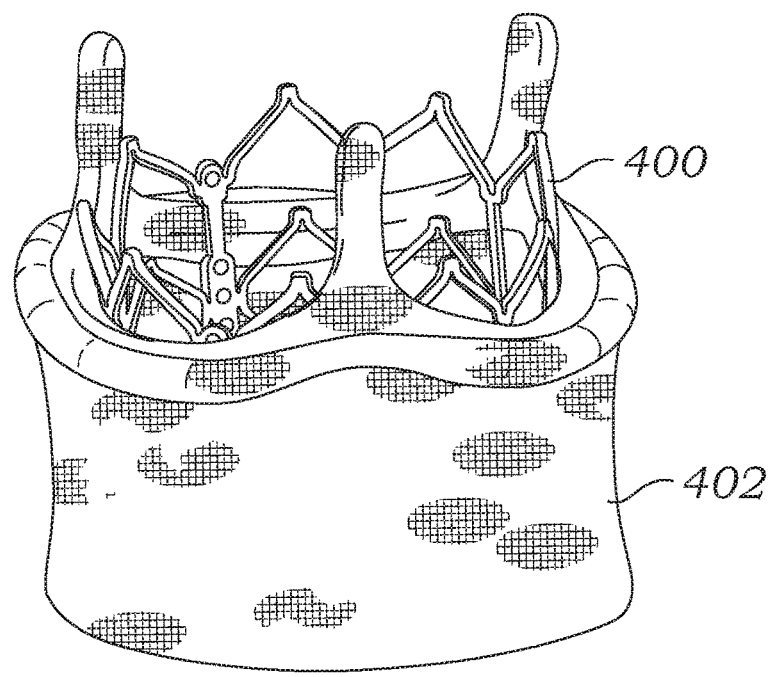
FIGS. 16A and 16B depict perspective and top views of an expandable prosthetic heart valve with a percutaneously-deliverable expandable prosthetic heart valve stent radially expanded therein according to an embodiment of the current invention.
Figure 16B:
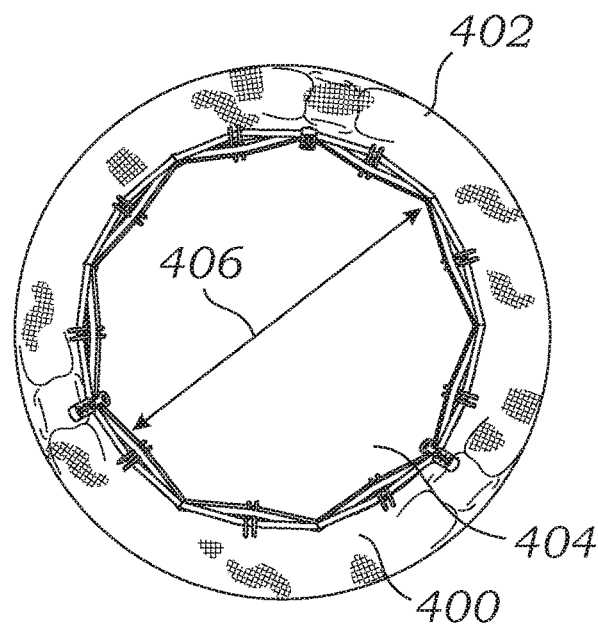
Figure 16C:
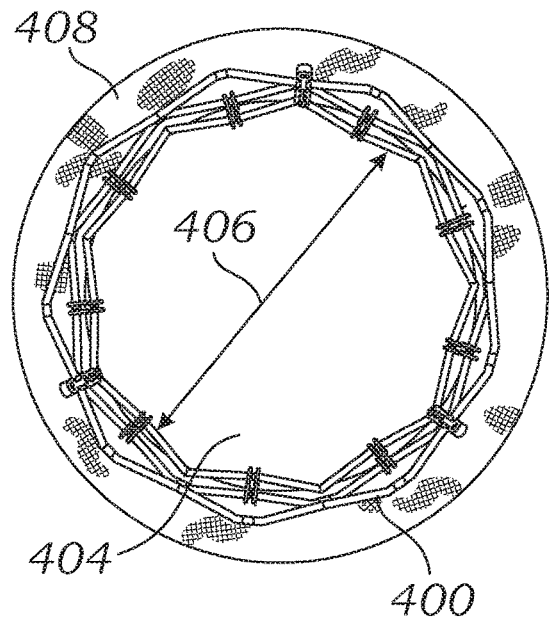
FIG. 16C depicts a top view of a prior art non-expandable prosthetic heart valve with a percutaneously-deliverable expandable prosthetic heart valve stent radially expanded therein.

FIGS. 16A-16C depict expandable transcatheter heart valve frames/stents 400 deployed via radial expansion within prosthetic heart valves 402, 408. (While in actual practice the full transcatheter heart valve would be deployed instead of just the stent, for visualization purposes only the stent 400 of the transcatheter valve is depicted in FIGS. 16A-16C.) In FIGS. 16A-16B, the transcatheter heart valve stent 400 is secured within the annulus 404 of the prosthetic heart valve 402 of the current invention. As seen most clearly in FIG. 16B, the stent 400 has a good shape and the central orifice 404 has a relatively large diameter 406 to assure good blood flow therein. This larger diameter orifice which is achieved due to the expansion of the prosthetic heart valve 402 of the current invention. By contrast, as depicted in FIG. 16C, if the originally-implanted prosthetic heart valve 408 is not radially expandable, it will have less internal space to accommodate the stent 400 than would be the the case for the expandable embodiment of FIG. 16B. Accordingly, in the prior art embodiment of FIG. 16C the stent 400 of a subsequently installed transcatheter valve will not be able to expand to as large a diameter, and the central orifice 404 will have a significantly smaller diameter 406 with corresponding reduction in blood flow.

FIG. 17A is a perspective view of another commercially-available surgical prosthetic heart valve 410 of the prior art. The main components of the heart valve 410 include an inner polymer stent 412, shown isolated in FIG. 17B, a plurality of flexible leaflets 414, typically a whole porcine valve, and a lower sewing ring 416 for securing the valve to an annulus. The components are typically covered with fabric and sewed together during manufacturing. This particular valve 410 is sold by Medtronic, Inc. of Minneapolis, Minn. under the trade names Hancock I™ or Hancock II™ and Mosaic™ and Mosaic Ultra™.

The inner polymer stent 412 supplies the main structural skeleton of the valve 410, and comprises a thin-walled tubular member with a lower circular band 418 that extends around the periphery of the stent, and a plurality of upstanding commissure posts 420. As with other conventional valves, there are three commissure posts 420 each of which supports edges of two adjacent leaflets. The polymer material of the stent 412 is sufficiently flexible to enable the commissure posts 420 to flex in and out somewhat during the cardiac cycle which this relieves some stress from the leaflets 414. However, conventional stents such as the polymer stent 412 are designed to maintain dimensional stability to the valve 410, and thus are sufficiently strong that they cannot be balloon expanded. Indeed, the Hancock II heart valve includes an embedded titanium ring (not shown) which further increases its resistance to expansion. Therefore, the prior art valve 410 must be explanted when it fails to enable introduction of a replacement valve. To avoid this situation, the present application contemplates various modifications to the polymer stent 412 that enable it to be balloon expanded so that the valve 410 need not be explanted.

Accordingly, FIGS. 18A-18D are perspective views of modifications to the inner support stent 412 of FIG. 17B that will enable the heart valve 410 of FIG. 17A to expand post-implantation. Each of these embodiments eliminates the titanium ring embedded in the Hancock II™ valve, however segmented rings that are not continuous around the periphery of the stent could still be used. For the sake of clarity, similar elements in the four different embodiments of FIGS. 18A-18D will be given the same numbers.

In FIG. 18A, an inner support stent 422 is substantially the same as the prior art support stent 412, but includes notches 424 positioned at the mid-cusp regions of the lower circular band portion 426. The "mid-cusp" location is intermediate to the upstanding commissure posts 428. The reduction in the cross-sectional area of the band portion 426 at these notches 424 thus creates points of weakness which will fail when a secondary prosthetic heart valve is expanded within the primary valve. As explained above, the material of the support stent 412 may be relatively brittle so that excessive tensile forces cause the notches 424 to break, or the material can be more ductile which permits the notches 424 to plastically stretch in the manner of taffy. Various formulations of biocompatible polymers are known with these differing physical properties.

FIG. 18B shows an inner support stent 430 provided with expandable segments 432 at the mid-cusp locations of the lower circular band portion 426. In the illustrated embodiment, the expandable segments 432 are similar to the expandable segments 196, 198 described above with respect to FIGS. 9A-9B. More specifically, the expandable segments 432 desirably include a pair of bent struts that connect upper and lower corners of the adjacent solid wall portions across gaps therebetween. The two struts are bent axially toward each other and will straighten out to extend straight across the gaps when an outward force is applied to the respective band, thus increasing the band diameter. The material may be plastically-deformable so as to assume a new shape when expanded, or may be simply elastic so as to permit expansion.

FIG. 18C illustrates a further support stent 434 which has two expandable segments 436 along each cusp part of the lower circular band portion 426. The provision of two expandable segments 436 between each commissure post 428 enables greater outward expansion for the stent 434, or simply distributes the expansion around the greater circumferential span.

Finally, FIG. 18D depict a support stent 438 having expandable segments 440 in the lower circular band portion 426 that comprise a series of diamond-shaped struts, similar to the accordion-like sections 162 shown in the embodiment of FIGS. 6A-6B. Indeed, any of the expandable segments shown in FIGS. 6-8 may be substituted for the expandable segments 440. Once again, the material of the stent 438 may be plastically-expandable, or may be the same polymer material as the prior art stent 412 wherein the expandable segments 440 simply permit post-implant expansion thereof.

Furthermore, in conjunction with any of the stent embodiments disclosed in FIGS. 18A-18D, and indeed in conjunction with the other stent embodiments disclosed herein, a biodegradable reinforcing band such as that shown with reference to FIG. 15 may be included for initial support after implantation. Such a reinforcing band will maintain dimensional stability for the valve during the initial period of tissue overgrowth, after which the modified stents will provide sufficient structural support for the valve, even though they can now be expanded by a balloon or other such expander.

Figure 19A:
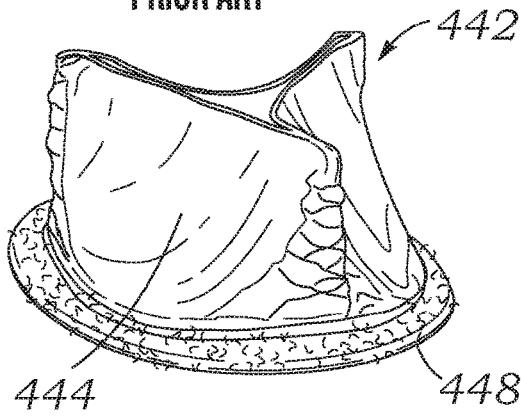
FIG. 19A is a perspective view of another commercially-available surgical prosthetic heart valve of the prior art having bioprosthetic tissue leaflets on the exterior thereof.

FIG. 19A is a perspective view of another commercially-available surgical prosthetic heart valve 442 of the prior art having bioprosthetic tissue leaflets 444 on the exterior thereof. An inner support stent 446 that supports the leaflets 444 is shown in the partially disassembled view of FIG. 19B.

The heart valve 442 also includes a sewing ring 448 and various fabric covers to assist in sewing the components together. This valve is sold as the Trifecta™ stented tissue valve by St. Jude Medical, Inc. of St. Paul, Minn. The inner support stent 446 in the Trifecta™ valve is formed of fatigue-resistance, high-strength titanium alloy. During assembly, the stent 446 is formed by laser cutting (e.g., from a tube), electro-polishing, and then covering the stent with a fabric prior to attaching to the sewing ring 448 and then the leaflets 444. Being titanium, the stent 446 may be somewhat flexible in the commissure posts 449, but strongly resists radial expansion. This is an advantage for a surgical valve such as the Trifecta™ valve, as it provides good dimensional stability. However, if the valve functioning deteriorates, and the valve must be replaced, it must be excised from the body first before a secondary valve can be implanted. Consequently, the present application discloses solutions for modifying the stent 446 of the Trifecta valve to permit post-implant expansion thereof.

At this stage it should be noted that the term "stent" to refer to the inner structural support of a heart valve is a term of art, and represents any structural element that generally provides circumferential or ring support to the valve leaflets. Sometimes such elements are termed frames, or simply support members, and it should be understood that the term stent encompasses a variety of configurations regardless of nomenclature.

Figure 19B:
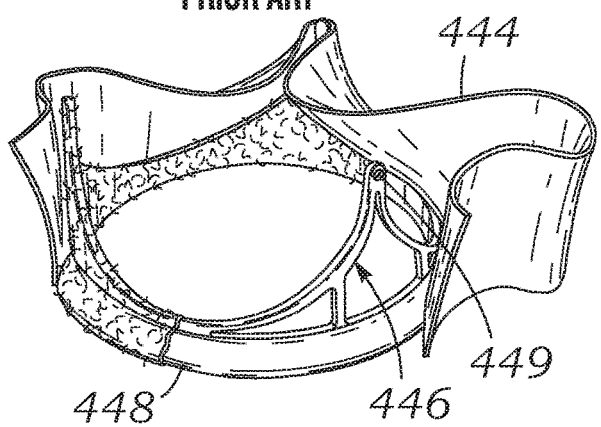
FIG. 19B is a perspective view of an inner support stent thereof.

FIGS. 20A-20G are perspective views of modifications to the inner support stent 446 of FIG. 19B that will enable the Trifecta™ valve of FIG. 19A to expand post-implantation.

Figure 20A:
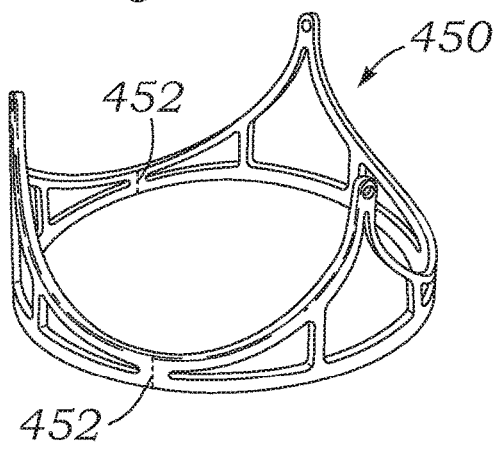
FIGS. 20A-20G are perspective views of modifications to the inner support stent of FIG. 19B that will enable the heart valve of FIG. 19A to expand post-implantation.

In FIG. 20A, a modified stent 450 features three perforated lines 452 located at the middle of each cusp region to form points of discontinuity. Outward expansion of a valve having the modified stent 450 will cause the stent to rupture at one or more of the perforated lines 452, thus permitting expansion of the secondary valve within the primary valve.

Figure 20B:
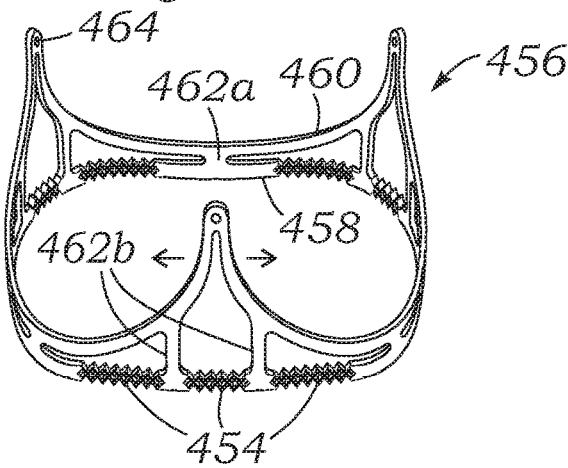

In FIG. 20B, a series of expandable segments 454 are provided around the periphery of a modified stent 456 to enable post-implant expansion. The Trifecta™ valve stent 446, and the modified stents shown in FIGS. 20A-20G, are formed by a framework of a lower circular band 458 structurally connected to an upper undulating band 460 via a plurality of axial struts 462. For example, there are three axial struts 462a at the midpoint of each cusp region, and two axial struts 462b flanking the upstanding commissure posts 464. The upper undulating band 460 defines three upstanding commissure posts 464 intermediate three downwardly arcing cusps. Desirably, there are three separate expandable segments 454 located in the lower circular band 458 in between and on the outside of each pair of axial struts 462b, as shown in FIG. 20B. In other words, the expandable segments 454 are centered underneath the commissure posts 464, and extend a short distance around the periphery of the stent 456. Outward expansion force applied to a valve having the modified stent 456 will cause the expandable segments 454 to stretch out, and will also bend outward the undulating band 460 at the commissure posts 464, as indicated by the movement arrows. Although not shown, the undulating band 460 above each of the expandable segments 454 may also be expandable. This configuration helps retain the structural integrity of the valve during its useful life, but still provides the ability to expand at some later date.

Figure 20C:
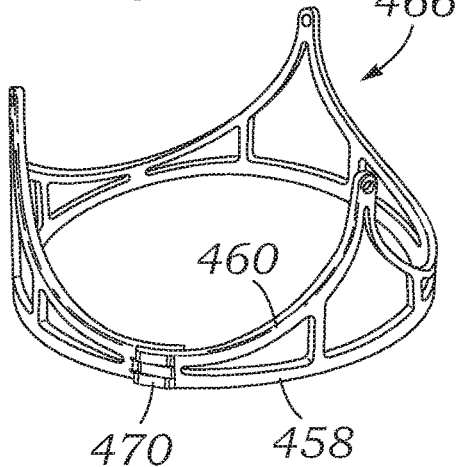
Figure 20D:
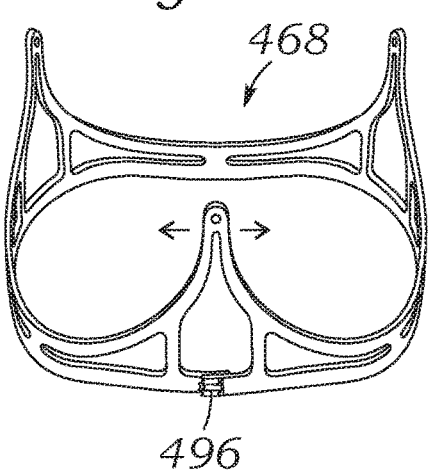

Now with reference to FIGS. 20C and 20D, modified stents 466, 468 include notches or interlaced tabs around their periphery that provide weakened or rupture points (points of discontinuity) so as to enable post-implant expansion of the stents. In FIG. 20C, interlaced tabs 470 at the mating ends of a circumferential band at one of the cusp midpoints are shown, generally where the lower band 458 and upper band 460 converge. Although not shown, the mating ends with the notches or interlaced tabs 470 may be provided at the three cusp locations. Alternatively, the stent 468 in FIG. 20D includes three notches or interlaced tabs 472 that are located in the lower band 458 and underneath one or more of the commissure posts 464. Expansion of a valve containing the stent 468 will thus cause one or more of the notches or interlaced tabs 472 to break or separate and the commissure posts of the stent to expand, as indicated by the movement arrows.

Figure 20E:
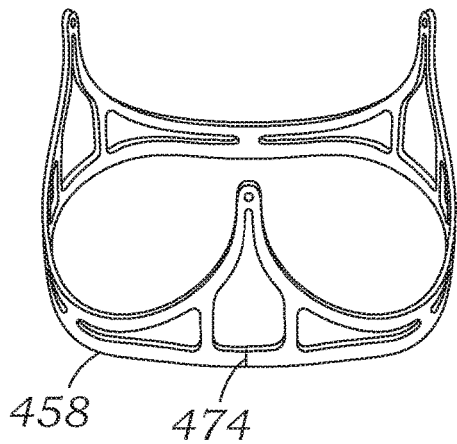
Figure 20F:
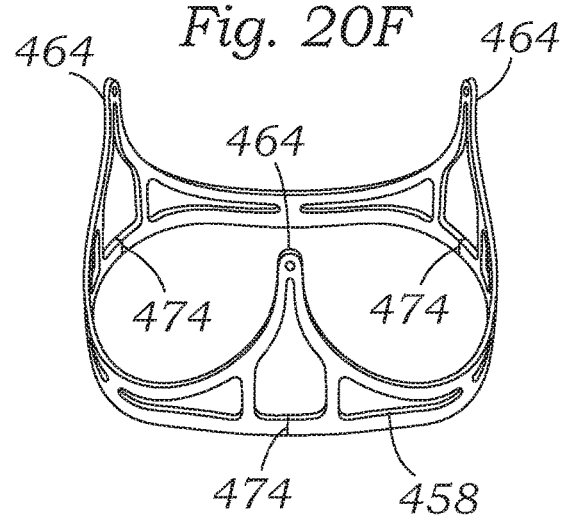

FIG. 20E shows a single break point 474 or point of discontinuity in the lower band 458 and underneath one or more of the commissure posts 464, while FIG. 20F shows three break points 474 in the lower band 458, again under each commissure post. The break points 474 could be simple cuts in the lower band 458 or perforations, as mentioned above. Since the cut ends of the stent at the break points 474 remain in abutment, and surrounded by cloth or other structure that holds them in alignment, they resist radial compression of the stent at the level of the band 458. On the other hand, the one-piece stent is adapted to expand at its base while remaining attached at the flexible commissure posts. This enables a valve to resist external forces applied by the implanting surgeon or by the heart while allowing expansion of the valve when a transcatheter valve is expanded within the surgical valve.

Figure 20G:
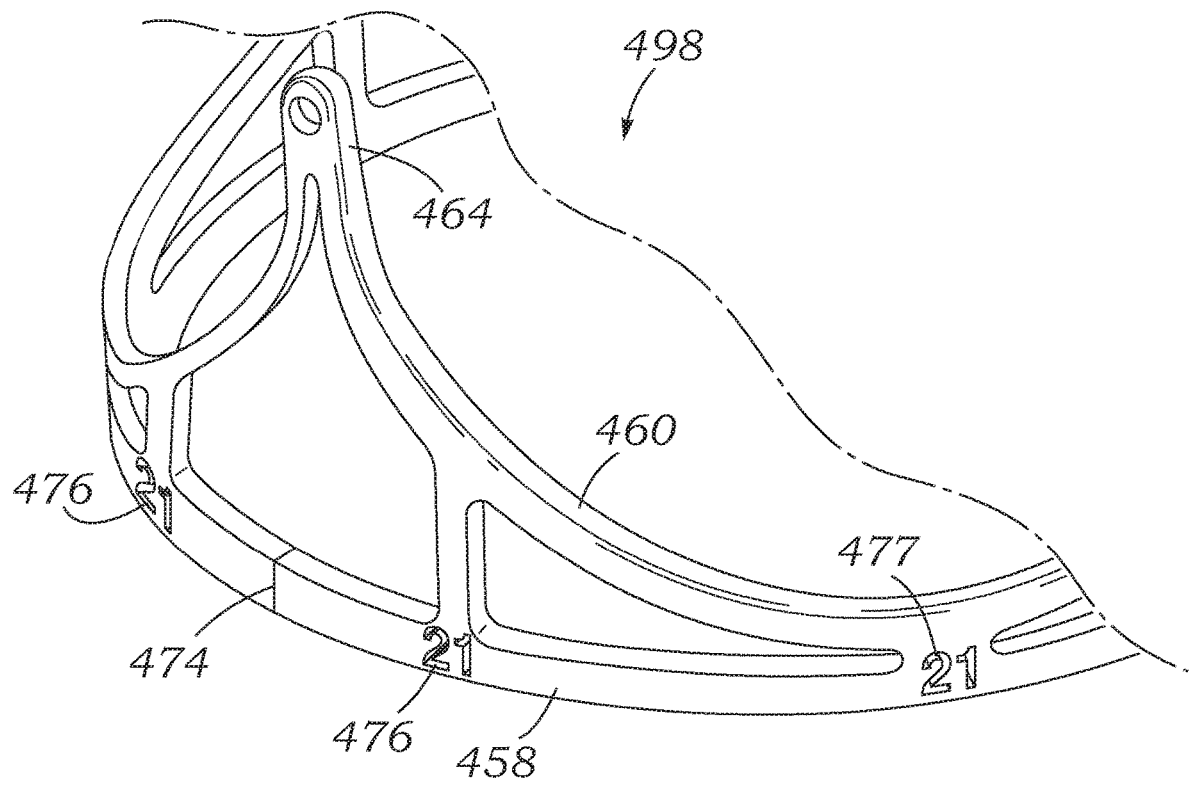

FIG. 20G is an enlarged view of one commissure post 464 with a break point 474 located directly underneath in the lower band 458. In addition, size markers 476 may be provided around the modified stent in various locations, such as in the lower band 458 adjacent to the commissure posts 464, or as seen at 477 in a cusp position. Alternatively, the size markers 476 may be located along the upper band 460. Preferably, the size markers comprise symbols or alphanumeric characters laser cut radially through the stent, which in the Trifecta™ valve, as mentioned, is formed of fatigue-resistance, high-strength titanium alloy, although other suitable materials can also be used for the stent, for example, stainless steel, cobalt-chromium (e.g., Elgiloy alloy), or nitinol. The through holes are thus visible in the negative under fluoroscopy or other viewing technologies. For instance, the number "21" is shown as the markers 476, 477 can indicate a valve size of 21 mm.

FIG. 21 is a perspective view of an inner support stent 480 of another surgical prosthetic heart valve of the prior art. The support stent 480 may also be made of metal, such as titanium, cobalt-chromium, nitinol, or stainless steel, or a polymer such as an acetal copolymer. The stent 480 includes three upstanding commissure posts 482 distributed evenly around a lower band 484. The lower band 484 is discontinuous below each commissure post 482 at a gap 485 which provides the entire structure with some circumferential flexibility. That is, the generally circular lower band 484 maintains a generally circular base structure for the assembled valve, but permits a minor amount of circumferential expansion and contraction. This may help in the valve functioning in terms of flexing with the surrounding systolic/diastolic movement of the native annulus.

The one-piece stent 480 also has three sinus or cusp supports 486 that extend away from the lower band 484 and diverge toward but do not touch the adjacent commissure post 482. The supports 486 have two diverging side arms 488 each with a lower end attached to the lower band 484 and a free end extending toward, but not connected to, an adjacent commissure post 482. Each support 486 is also attached to the lower band 484 at its midpoint so as to leave two small side windows 489.

The side arms 488 are not rigidly connected to the adjacent support posts 482 to which they are closest. By this lack of connection the cusp supports 486 do not unduly affect the natural flexibility/stiffness of the adjacent support post 482, nor affect the stress response of the free-standing stent. However, it will be appreciated that the presence of a tissue valve such as shown in FIG. 19A sutured to the stent 480 provides an indirect tissue connection between a given commissure post 482 and an adjacent side arm 488. This indirect tissue connection is believed useful for several reasons. First, the indirect tissue connection between two adjacent commissure posts 482 via the intermediate cusp support structure 486 places a constraint condition on movement of the two commissure posts. Indeed, all three commissure posts 482 are similarly constrained by the indirect connection with the other two posts. This constraint causes the three support posts to act in unison when the valve is properly attached to the stent.

FIGS. 22A-22D are perspective views of modifications to the inner support stent 480 of FIG. 21 that will enable the heart valve to expand post-implantation. In FIG. 22A, the support stent 490 has short wall segments 491 that extend toward and into abutment with each other from the base of each side of the commissure posts 482. The wall segments 491 touch but are otherwise not connected at a point of discontinuity, so as to complete the otherwise solid lower band 484 and prevent contraction of the stent 490. At the same time, the stent 490 may be expanded at the lower band 484 such as when a transcatheter valve is expanded within the surgical valve. There are preferably three point of discontinuity created by the abutting wall segments 491 below each commissure post 482, though just one would permit the surgical valve to be expanded post-implant in a valve-in-valve procedure.

FIG. 22B shows a similar stent 490 with the short wall segments 491 below each commissure post 482 that come together and are only separated by a perforated junction 492. This junction 492 provides a point of discontinuity in the solid lower band 484 that again prevents contraction of the band 482 but upon breaking permits expansion. Inflation of a balloon catheter to as little as 1 atmosphere may be enough to break the perforated junction 492, or a more robust junction may be desired to resist up to 12 atm, for instance. FIG. 22C shows a stent 490 with an expansion member 494 disposed in the gap 485 between the commissure post 482 sides, in line with the solid lower band 484. Again, the expansion member 494 is preferably tightly a coiled substantially serpentine structure to prevent contraction of the lower band 484 but provides a point of discontinuity that is easily expanded upon application of an inner balloon dilation force, for example. The material of the expansion member 494 may be elastically or plastically expandable. In one preferred embodiment, the entire stent 490 including the expansion members 494 are laser cut from a titanium tube. Finally, FIG. 22D shows a stent with wall segments 491 terminating in mutually interlaced free ends 496 forming a point of discontinuity in the lower band 484. The free ends 496 prevent contraction of the lower band 484 but slide away from one another if subjected to an expansion force. Moreover, as with the expansion members 494, the interlaced free ends 496 help maintain alignment of the lower band 484 and thus circularity of the entire lower portion of the stent 490.

As mentioned, each of the stents 490 shown could be laser cut from a tube or injection molded. Alternatively, a stent 490 that has a complete base could be cut with an abrasive saw, wire EDM, water jet, machining, or some other cutting technology, or some combination of methods. The stents 490 are preferably titanium, but may be stainless steel, Elgiloy, Nitinol, or even a polymer.

FIG. 23A shows a still further commercially-available surgical prosthetic heart valve 504 of the prior art having two detachable components—a valve leaflet subassembly 505 and a docking or base member 506. FIG. 23B shows the two components coupled together to form the functioning prosthetic heart valve 504. These drawings represent the Vitality™ or VXi™ two-piece heart valve system sold by ValveXchange, Inc. of Greenwood Village, Colo. The valve leaflet subassembly 505 comprises a plurality of flexible leaflets 507 mounted to a frame that includes connectors 508 located at commissure areas. The base member 506 primarily includes a tubular stent 509 having upstanding commissures 510. The tubular stent 509 in the Vitality™ valve is a biocompatible polymer.

The connectors 508 of the leaflet subassembly 505 include structure for mating with corresponding structure on the upstanding commissures 510 so as to form the final two-piece valve assembly 504 as seen in FIG. 23B. The system is designed to first implant the base member 506, such as by sewing it in place at the annulus, and then advancing the leaflet subassembly 505 into position and coupling the connectors 508 with the commissures 510. Down the road, if the valve 504 becomes incompetent or otherwise as a decrease of function, the base member 506 can remain in place while the leaflet subassembly 505 is removed and replaced with a new one. However, while this configuration obviates the need to excise the entire valve, the procedure for removing the original leaflet subassembly 505 and connecting a new one is relatively complicated. Instead, the present application contemplates modifying the base member 506 to enable it to be expanded post-implant by a secondary expandable heart valve advanced transfemorally or transapically.

FIGS. 24A-24C illustrate several modifications to the inner support stent 509 of FIG. 23B that will enable a base member 506 of the two-part heart valve 504 of FIG. 23A to expand post-implantation.

For example, FIG. 24A shows a modified stent 511 including one or more (two shown) circular reinforcing filaments 512 embedded within the material of the stent and surrounding the lower portion thereof. Three biodegradable wall segments 513 of the stent 511 are provided at approximately the mid-cusp locations. Initially, the stent 511 functions the same as the stent 509 for the prior art base member 506, and has sufficient circumferential strength to maintain dimensional stability during the initial tissue ingrowth period. After some time in the body, the wall segments 513 degrade, but the presence of the reinforcing filaments 512 maintains the circularity of the stent 511. If the leaflet subassembly starts to wear out, a secondary expandable prosthetic valve may be advanced into position within the two-piece valve and expanded outward, whereby the filaments 512 will break, permitting the stent 511 to expand. This obviates the need for removing the leaflet subassembly.

FIG. 24B illustrates another modified stent 514 which is shaped nearly the same as the original stent 509 and made of the same material. At the mid-point of the cusps, the stent 514 includes weakened regions 515 wear the radial thickness of the wall gradually decreases to a magnitude that permits it to be broken or stretch upon expansion of a balloon within the stent. The polymer material of the stent 514 may be relatively brittle so that the weakened regions 515 break, or the material can be ductile which permits the weakened regions 515 to plastically stretch. Again, this provides good dimensional stability throughout the life of the leaflet subassembly, but permits introduction of a secondary expandable valve within the two-piece valve rather than replacing the leaflet subassembly.

Finally, alternative stent 516 shown in FIG. 24C includes three biodegradable chordal segments 517 located in the cusp regions. More particularly, the chordal segments 517 taper larger from the commissures of the stent 516 until their maximum axial dimension at the mid-points of the cusps so as to be smile-shaped. The overall shape of the stent 516 with the chordal segments 517 is identical to the prior art stent 509. However, after some time in the body, the chordal segments 517 degrade leaving relatively small cross-section cusp bridges connecting the commissures of the stent 516 which are susceptible to rupture or stretching upon inflation of an expansion balloon therein. Again, depending on the properties of the polymer material of the stent 516 the cusp bridges will break or plastically stretch. Accordingly, when the leaflet subassembly deteriorates, a secondary expandable valve can be introduced within the two-piece valve and expanded, breaking apart the stent 516 in the process.

Note that there are many variations of the above-cited embodiments, including numerous combinations of the various embodiments, all of which are in the scope of the invention. Segments of one embodiment can be combined with the expandable portions of other embodiments. Also, a particular support structure could have any combination of the above-discussed expandable portions.

Figure 25A:
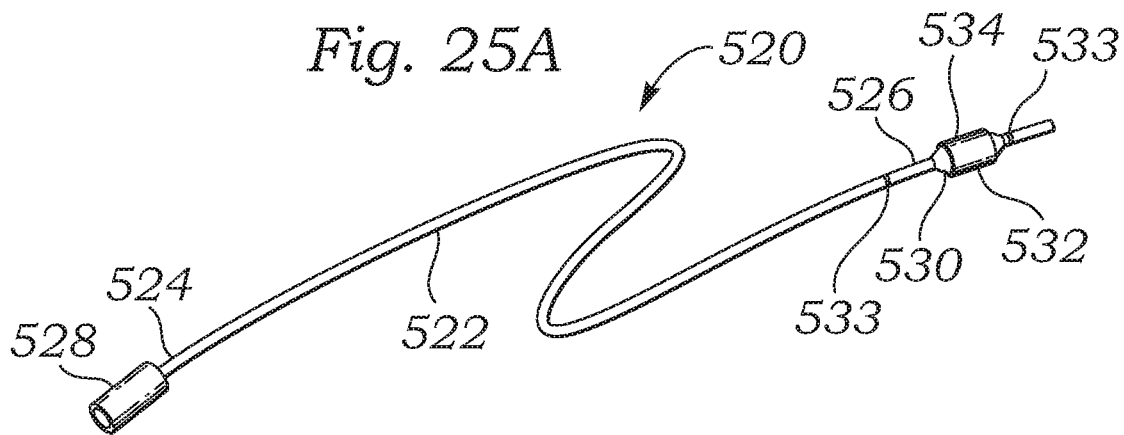
FIG. 25A depicts an expandable prosthetic heart valve deployment catheter configured for expandable prosthetic heart valve deployment according to an embodiment of the invention.

FIG. 25A depicts an expandable prosthetic heart valve deployment catheter 520 configured for (prior) prosthetic heart valve dilation and (replacement) expandable prosthetic heart valve deployment. The deployment catheter 520 has an elongated main body 522, a proximal end 524, and a distal end 526. The proximal end 524 includes a handle 528. The distal end 526 includes a dilation balloon 530 upon which an expandable prosthetic valve 532 is mounted. In the particular embodiment depicted, the expandable prosthetic valve 532 includes a stent 534. The distal end 526 may also include one or more radiopaque markers 533 or similar visibility markers to improve visibility of the device within the patient when using fluoroscopy or other viewing technologies.

FIGS. 25B-25D depict deployment of an expandable prosthetic heart valve 532 within a heart valve annulus 536 where a prosthetic heart valve 518 has previously been deployed. The previously-deployed prosthetic heart valve 518 may have been deployed using any methods, including methods currently known in the art such as traditional (open chest) surgery, minimally-invasive (e.g., keyhole) surgery, and percutaneous surgery. Depending on the particular application, the previously-deployed prosthetic heart valve 518 can be deployed in the patient years prior to, days prior to, hours prior to, or immediately prior to deployment of the expandable prosthetic heart valve 532 as depicted in FIGS. 25B-25D.

FIG. 25B depicts the expandable prosthetic heart valve deployment catheter 520 of FIG. 25A with the distal end 526 advanced so that the dilation balloon 530 and expandable prosthetic heart valve 532 are positioned within the previously-deployed prosthetic heart valve 518 in the patient's heart 540. The previously-deployed prosthetic heart valve 518 is seen in cross-section to show the generally rigid and/or expansion-resistant support frame 538.

In the particular embodiment depicted in FIG. 25B, the deployment catheter 520 has been advanced over a guide wire 542, which was advanced into the patient's heart 540 and previously-deployed prosthetic heart valve 518 prior to advancement of the deployment catheter 520 into the patient. Note that the use of a guide wire 542 is optional. Other guide devices could also be used, in addition to or in lieu of a guide wire. For example, a guide catheter could be used, wherein a guide catheter is advanced to a desired position within a patient, and the deployment catheter is then advanced into the patient inside of the guide catheter until the distal end of the deployment catheter extends from a distal opening in the guide catheter. A deployment catheter could also be used without any sort of guide wire or guide catheter, so that the deployment catheter is guided by itself into the desired treatment location.

As depicted in FIG. 25C, once the dilation balloon 530 and expandable prosthetic heart valve 532 are properly positioned within the heart valve annulus 534 and previously-deployed prosthetic heart valve 518, the dilation balloon 530 is expanded. The expanding dilation balloon 530 forces the stent 534 to expand outwardly, and forces the leaflets 544 of the previously-deployed prosthetic heart valve 518 against the heart valve annulus 536. The force from the expanding dilation balloon 530 also dilates the previously-deployed prosthetic heart valve 518 and heart valve annulus 536, forcing the support frame 538 of the previously-deployed prosthetic heart valve 518 to expand.

In FIG. 25D, the dilation balloon 530 is deflated or otherwise reduced in diameter, with the new expandable prosthetic valve 532 deployed in the heart valve annulus 536 and previously-deployed prosthetic heart valve 518, and also held in place by the stent 534. The outward pressure from the expanded stent 532, along with the inward pressure from the heart valve annulus 536 and from any elastic portions (such as core, cords, and/or or covers) of the previously-deployed prosthetic heart valve 518 or from the previously-deployed prosthetic heart valve leaflets 544, combine to firmly seat the new expandable prosthetic valve 532 in the desired position in the heart valve annulus 536 and previously-deployed prosthetic heart valve 518. The deployment catheter 520 with the dilation balloon 530 can then be withdrawn from the heart 540, leaving the new expandable prosthetic heart valve 532 in its deployed position within the patient and the previously-deployed prosthetic heart valve 518.

Figure 26A:
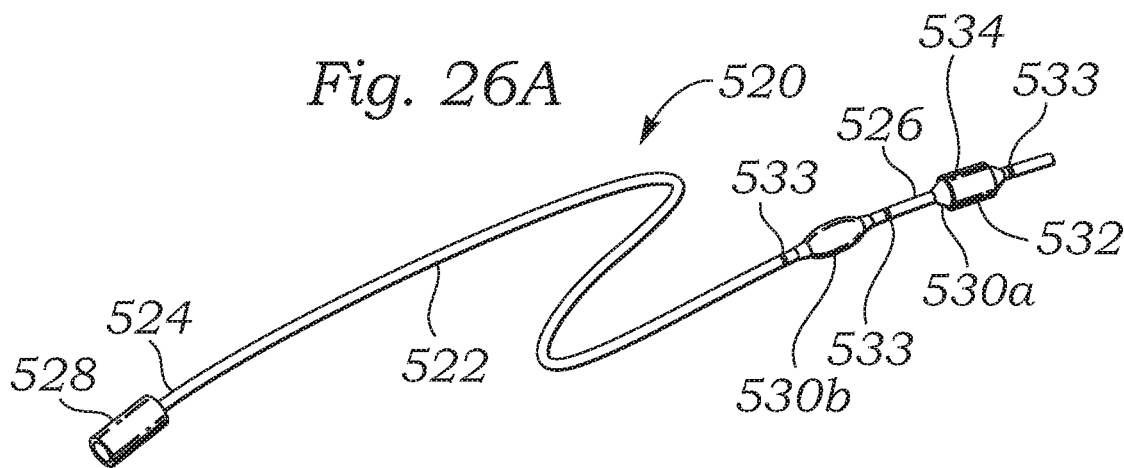
FIG. 26A depicts an expandable prosthetic heart valve deployment catheter configured for dilation of a previously-deployed prosthetic heart valve and for deployment of an expandable prosthetic heart valve according to an embodiment of the invention.

In a further embodiment of the invention, the previously-deployed prosthetic heart valve 518 is dilated in a separate step from deployment of the expandable prosthetic heart valve 532. FIG. 26A depicts an expandable prosthetic heart valve deployment catheter 520 configured for previously-deployed prosthetic heart valve dilation and expandable prosthetic heart valve deployment using two separate balloons, and more specifically a distal balloon 530a and a proximal balloon 530b. The distal balloon 530a is configured to deploy the new expandable prosthetic valve 532, which is positioned on the distal balloon 530a, whereas the proximal balloon 530b is configured for dilation of the previously-deployed prosthetic heart valve 518.

FIGS. 26B-26D depict dilation of the previously-deployed prosthetic heart valve 518 and valve annulus 536 using the proximal balloon 530b. In FIG. 26B, the deployment catheter 520 has been advanced into the heart 530 with the distal balloon 530a (with expandable prosthetic valve 532 thereon) advanced past the previously-deployed prosthetic heart valve 518, and the proximal balloon 530b positioned within the previously-deployed prosthetic heart valve 518 and valve annulus 536.

The proximal balloon 530b is inflated or otherwise expanded, as depicted in FIG. 26C, thereby dilating the previously-deployed prosthetic heart valve 518 and valve annulus 536. The support frame 538 of the previously-deployed prosthetic heart valve 518 is expanded and/or assumes a generally non-rigid configuration, similarly to the changes previously discussed with respect to the dilation discussed in FIG. 26C above.

After dilation of the previously-deployed prosthetic heart valve 518, the proximal balloon 530b is deflated or otherwise reduced in diameter, as depicted in FIG. 26D. The deployment catheter 520 may then be withdrawn from the patient until the proximal balloon 530b is proximal of the previously-deployed prosthetic heart valve 518 and the distal balloon 530a is positioned within the previously-deployed prosthetic heart valve 518. The distal balloon 530a will be positioned within the previously-deployed prosthetic heart valve 518 in a similar fashion to that depicted for balloon 530 in FIG. 25B. The distal balloon 530a will then be expanded to deploy the expandable prosthetic valve 532 in essentially the same manner as was discussed and depicted in FIGS. 25B-25D. The distal balloon 530a will serve to deploy the new expandable prosthetic valve 532, and may also serve to further dilate the previously-deployed prosthetic heart valve 518 and/or native valve annulus 536.

Note that in an alternate embodiment two separate catheters are used for dilating the previously-implanted prosthetic valve. The first balloon catheter is a traditional dilation catheter and is advanced into the patient to a position within the previously-deployed heart valve. The balloon of the first balloon catheter is expanded to a desired pressure (e.g., 4-5 atm) sufficient to dilate (radially expand) the previously-implanted prosthetic valve. The first balloon catheter is then withdrawn from the patient, and a second balloon catheter (such as that depicted in FIGS. 25A-25D) with balloon and new expandable prosthetic heart valve thereon is advanced into the patient, the balloon is expanded to deploy the new expandable prosthetic heart valve within the previously-implanted (and now dilated) prosthetic heart valve, and the second balloon catheter is withdrawn from the patient.

Note that the expandable prosthetic valve may be self-expanding, in which case the deployment catheter may not have a dilation balloon as depicted in FIGS. 25A-25D and 26A-26D. Moreover, such a self-expanding prosthetic heart valve could be deployed with or without prior dilation of the previously-deployed prosthetic heart valve. For example, a self-expanding prosthetic heart valve may provide sufficient outward radial force to dilate the previously-deployed prosthetic heart valve and/or to hold a now-dilated previously-deployed prosthetic heart valve in an expanded configuration in order to provide sufficient room for the self-expanding prosthetic heart valve in its expanded configuration.

In order for a valve-in-valve procedure to be successful, an interference fit or some other form of anchoring is required between the inside diameter of the primary surgical valve and the outside diameter of the secondary expandable valve. Without sufficient anchoring between the two valves, the secondary valve can migrate axially due to the closing fluid pressure acting on the valve. This is particularly important when a large sized expandable valve, e.g. 29 mm, deploys within a 29 mm or larger surgical valve. With such combinations, there may not be enough friction to secure the secondary valve within the primary valve. Consequently, the present application contemplates an improved adapter frame to be positioned between the two valves to ensure good anchoring.

Figure 27B:
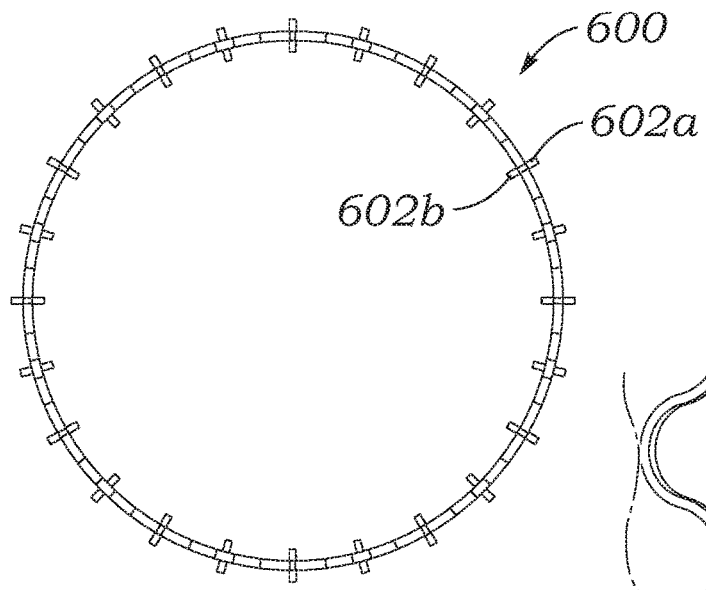
FIGS. 27A and 27B are perspective and top plan views, respectively, of an exemplary tubular adapter frame having barbs that may be used between a previously implanted valve and a newly implanted expandable valve to enhance anchoring therebetween.
Figure 27A:
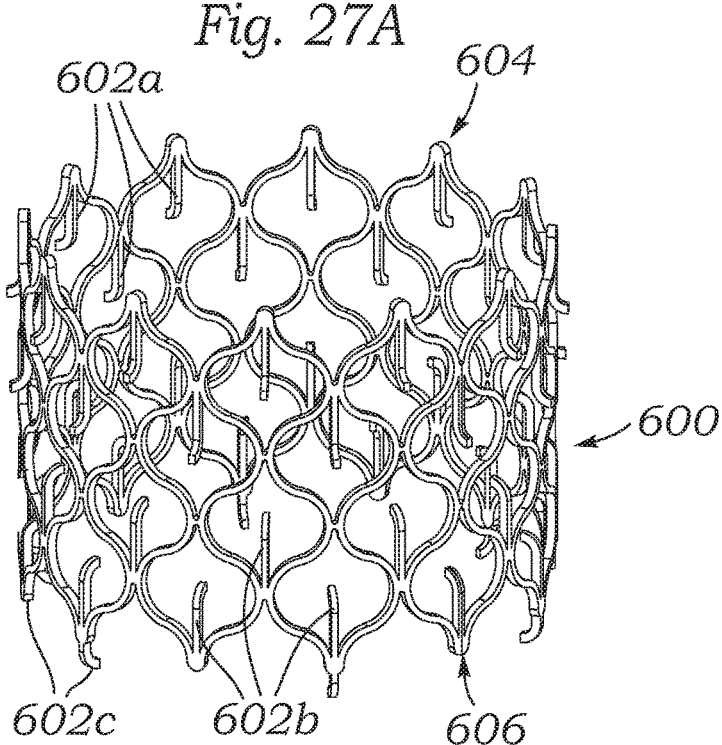

FIGS. 27A and 27B are perspective and top plan views, respectively, of an exemplary tubular adapter frame 600 having barbs 602 that enhance anchoring of a newly implanted expandable valve to a previously implanted valve. In the illustrated embodiment, the upper end 604 is an outflow end, while the lower end 606 is the inflow end. As mentioned, the adapter frame 600 is advanced into the body and expanded outward into contact with the primary surgical valve prior to expansion of a secondary expandable valve. The barbs 602 help provide stability and resistance to migration. In a preferred embodiment, there are both inwardly and outwardly facing barbs 602, as described below.

Figure 27C:
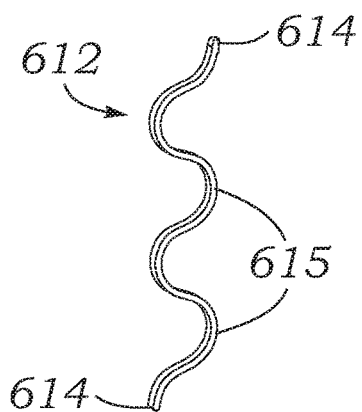
FIG. 27C is an isolation of one strut segment thereof.

In the embodiment shown in FIG. 27A, the adapter frame 600 comprises an expandable latticework of struts that may take a variety of configurations. For example, the struts may comprise a series of generally axially-oriented serpentine segments 612, one shown isolated in FIG. 27C, having free ends 614 and intermediate apices 615 connected to an adjacent segments 612. The assembly of the serpentine segments 612 defines circumferential rows of connection points at and between the two ends 604, 606. In the illustrated embodiment, there are four rows of connection points between the adjacent axially-oriented segments 612 in the body of the adapter frame 600 between the two ends six of four, 606. Of course, the spacing of the curves in the serpentine segments 612 and the total length can be adjusted so that the number of rows of connection points may vary. The exemplary embodiment shown has 24 individual serpentine segments 612 with two rows of 12 each upper barbs 602a and two rows of 12 each lower barbs 602b.

FIG. 27A shows outwardly-directed barbs 602a extending from the connection points at the outflow end 604 as well as from the connection points in the adjacent row. Each barb 602a comprises a linear segment extending from the corresponding connection point toward the inflow end 606 having a small outwardly curved free end. The outwardly-directed barbs 602a are intended to interface with the leaflets and commissure posts of the surrounding surgical valve. Conversely, a plurality of inwardly-directed barbs 602b extend from the connection points at the inflow end 606 as well as from the connection points in the adjacent row. The inwardly-directed barbs 602b are intended to interface with the frame struts of a secondary expandable valve. Once again, each barb 602b comprises a linear segment extending from the corresponding connection point in having a small inwardly curved free and, but this time the barbs are oriented toward the outflow end 604. In this way, no barbs extend beyond either the outflow or inflow ends 604, 606.

Optionally, however, a series of inwardly-direct barbs 602c are provided extending from one or both of the outflow or inflow ends 604, 606. For example, a plurality of barbs 602c are shown extending from every other connection point on the inflow end 606 (total of six). This additional row of barbs at 602c is desirably below the bottom of the secondary expandable valve, and in the case of an aortic implantation would act as a "safety stop" to prevent migration of the secondary valve into the left ventricle.

It should be understood that the tubular frame 600 itself may provide sufficient friction between the two valves such that barbs are not necessary. If barbs are used, they maybe oriented inwardly, outwardly, or both. Inwardly-direct barbs may be provided on one end, and outwardly-directed barbs on the other hand, as shown in FIG. 27A, or they may be interspersed throughout the frame 600. In preferred embodiments, the inwardly-directed barbs are provided on the inflow end of the frame 600, and the outwardly directed barbs are provided on the outflow end.

Figure 28:
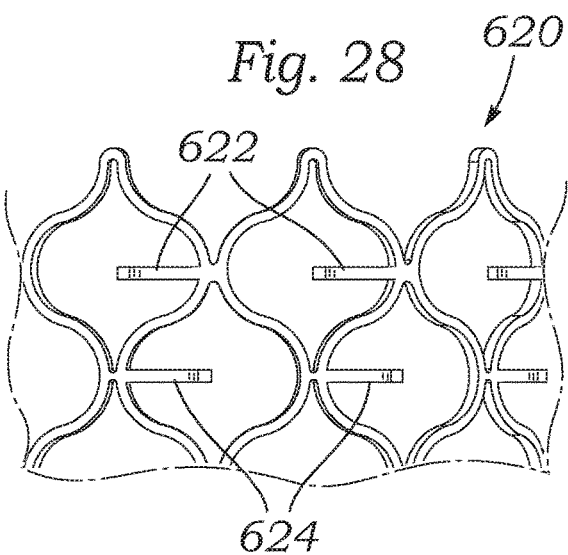
FIG. 28 is a perspective view of a portion of an alternative tubular adapter frame having horizontally-oriented barbs.

FIG. 28 is a portion of an alternative tubular adapter frame 620 adjacent and outflow end 604 having a number of horizontally-oriented barbs instead of being oriented vertically. A first series of barbs 622 oriented in a first circumferential direction (to the left) extend from the row of connection points between struts adjacent to the outflow end 604. A second series of barbs 624 oriented in the opposite circumferential direction (to the right) extend from the next row of connection points away from the outflow end 604. Again, these barbs at 622, 624 may free ends that are curved inwardly or outwardly, but are desirably curved outwardly adjacent the outflow end 604.

The tubular adapter frame 600 could be covered in cloth to help prevent blood leakage through the open cells defined between the serpentine struts. Preferably, a cloth with a high friction coefficient is used. Additionally, a velour type of cloth could also be used on the inside or outside to further help prevent leakage. Another possibility is to coat the tubular frame 600 in a soft polymer, such as silicone, such that the metallic struts are covered to reduce blood interactions and potentially increase retention fiction.

The wall thickness and diameter of the tubular adapter frame 600 could be specific to certain combinations of primary surgical valves and secondary expandable valves. For example, if implanting a 29 millimeter expandable valve within a 29 mm surgical valve, the wall thickness could be about 0.5 mm with an outside diameter in the expanded state of the frame of about 28 mm. For a 29 mm secondary expandable valve placed within a 31 mm surgical valve, the wall thickness could be increased to about 1.0 mm and the frame 600 has an outside diameter in its expanded state of about 30 mm.

Figure 29A:
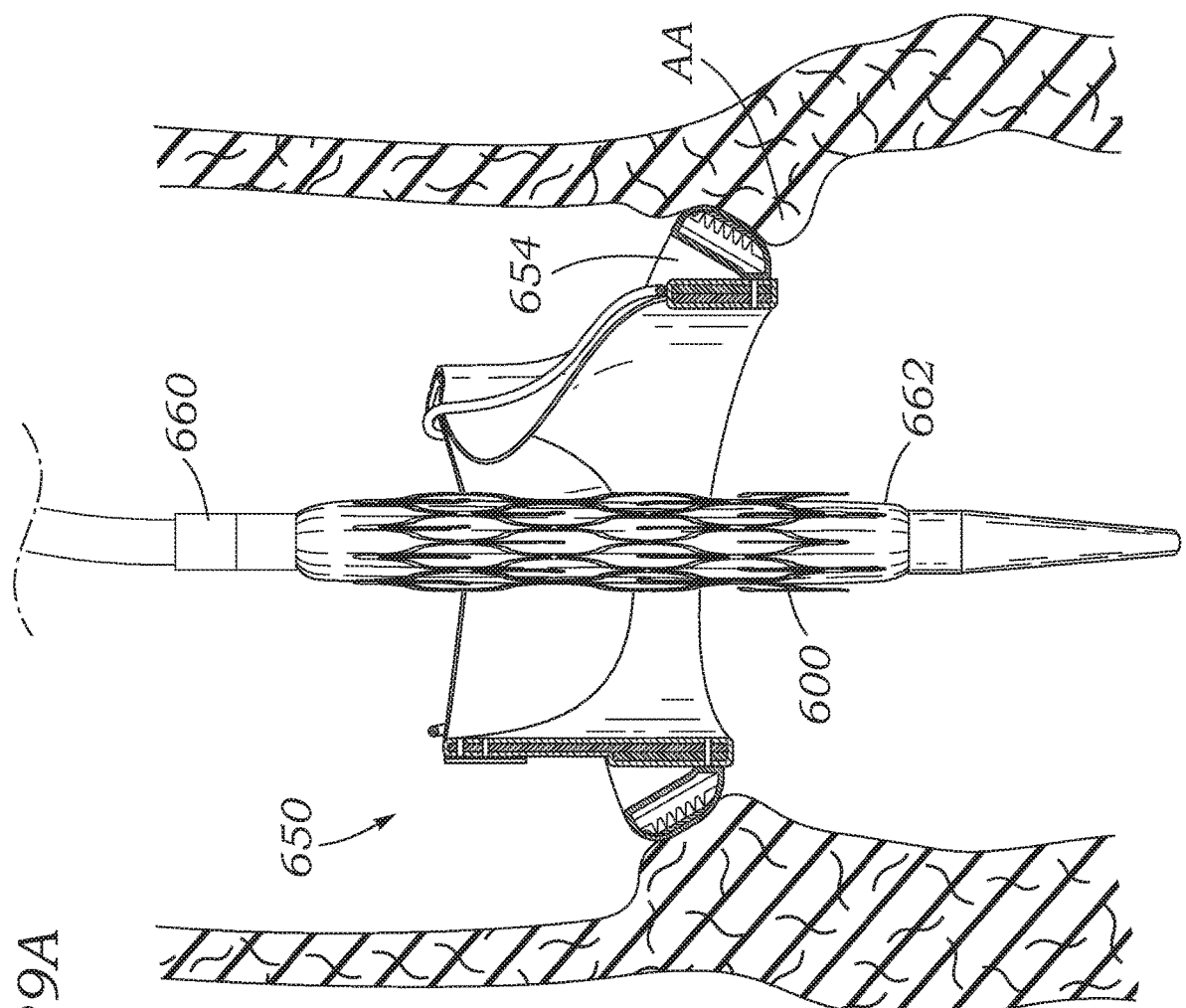
FIG. 29A-29C schematically illustrate implant of a secondary expandable valve within an expandable tubular adapter frame first expanded within a previously-implanted prosthetic heart valve.
Figure 29B:
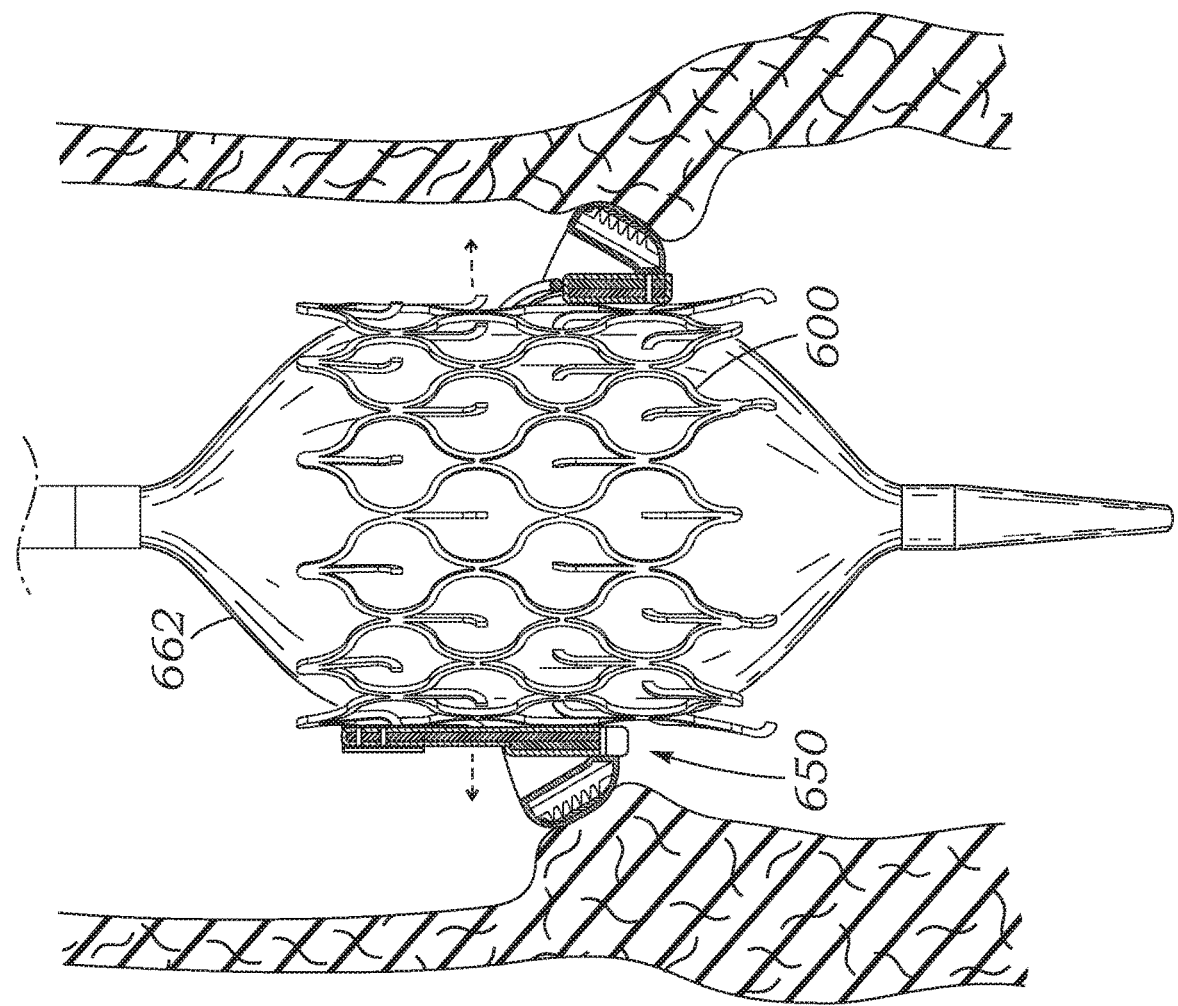
Figure 29C:
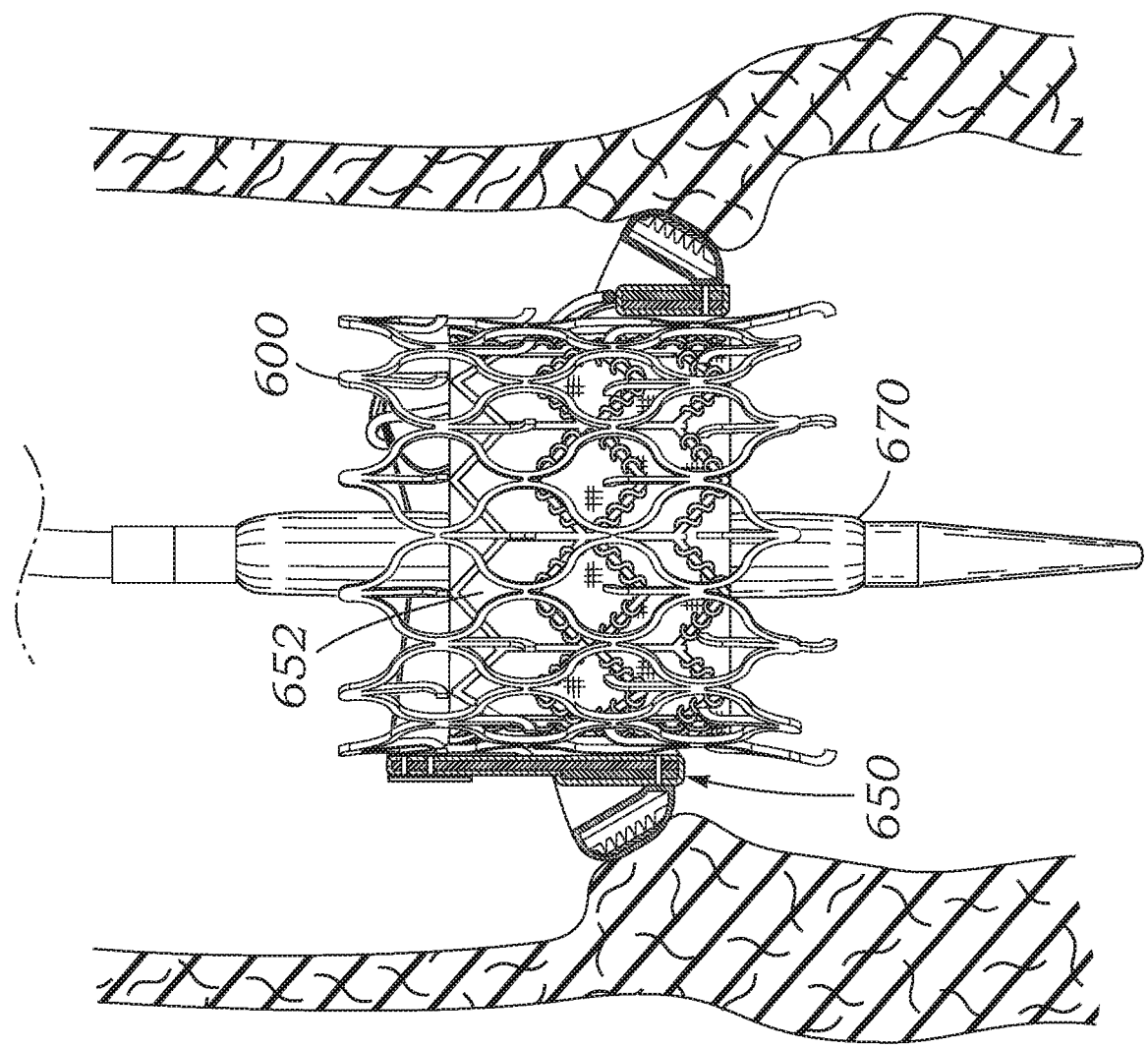

FIG. 29A-29C schematically illustrate a sequence where the adapter frame 600 is used between a previously-implanted or primary prosthetic heart valve 650 and a secondary expandable valve 652. The primary heart valve 650 is shown in FIG. 29A implanted at an aortic annulus AA. In the illustrated embodiment, the heart valve 650 is shown as a modified Perimount™ valve manufactured by Edwards Lifesciences of Irvine, Calif., though it is representative of a number of other surgical valves, as explained elsewhere herein. The surgical valve 650 is modified to enable post-implant expansion. The valve 650 typically includes a sewing ring 654 through which sutures (not shown) are threaded to secure the valve to the annulus AA.

A balloon catheter 660 extends in a retrograde fashion downward from the ascending aorta until a balloon 662 having the adapter frame 600 thereon is positioned directly within the valve 650. The axial height of the adapter frame 600 is shown longer than the actual height of the valve 650, although a shorter frame may be effectively used.

FIG. 29B illustrate outward expansion of the balloon 662 to cause commensurate expansion of the tubular adapter frame 600 which, in turn, outwardly expands the surgical valve 650. In a preferred embodiment, the magnitude of expansion of the balloon 662 is sufficient to cause outward expansion of the surgical valve 650 until the inner diameter of the adapter frame 600 is at least as large as the original inner diameter of the surgical valve. More preferably, the balloon 662 outwardly expands the frame 600 to an extent that the inner diameter of the frame is larger than the original inner diameter of the surgical valve so as to enable subsequent expansion of the secondary valve they are within and end up with the same orifice size as the original valve.

Finally, FIG. 29C shows the secondary expandable valve 652 after having been outwardly expanded into intimate contact with the inner surface of the tubular frame 600. This effectively sandwiches into a frame 600 between the two valves, creating additional interference and enhanced retention force, and decreasing the likelihood of migration. This is particularly useful for larger sized surgical valves. Again, the orifice defined by the expanded valve 652 is desirably at least as large as the original inner diameter of the surgical valve 650. The secondary valve 652 may be expanded using a balloon 670, as shown, or via a mechanical expander. Alternatively, the secondary valve 652 may be self-expanding, with the adapter frame 600 being plastically-expandable to provide a robust force holding the primary surgical valve 650 in its expanded configuration. A self-expanding secondary valve 652 thus comes into intimate contact with the tubular frame 600, and the frictional contact therebetween may be supplemented by the aforementioned barbs described above with respect to FIGS. 27-28.

Advantageously, the adapter frame 600 can be crimped to a relatively small diameter and delivered through a small catheter. Because of the smaller profile, the adapter frame 600 and its delivery system can be integrated into an existing secondary valve delivery catheter system. In that case, the overall delivery system can be advanced to align the adapter frame 600 with the existing surgical valve 650, the frame 600 deployed, and then the delivery system used to advance and deploy the secondary expandable valve 652 within the frame. All this reduces the procedure time.

As mentioned, the frame 600 can be either plastically-expandable, such as stainless steel or cobalt-chromium alloy, or self-expanding, such as Nitinol. In the latter case, a series of loops with tethers can be used on the distal end of the frame 600 to control expansion as it is pushed out of a catheter. However, the outward spring force of the frame 600 can be made relatively low, because it is later sandwiched by the secondary valve 652, in which case the frame does not have a great tendency to "jump" out of the catheter. A self-expanding adapter frame 600 can even be made from a suitable polymer, as the spring constant requirements are relatively low.

While the invention has been described with reference to particular embodiments, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular embodiments disclosed herein, but that the invention will include all embodiments falling within the scope of the appended claims.

What is claimed is:

1. A prosthetic heart valve adapted for post-implant expansion and having an inflow end and an outflow end, comprising:

a one-piece inner structural support stent including a generally circular solid lower band having three upstanding commissure posts, the stent defining an implant circumference that is substantially non-compressible in normal physiological use and has a first diameter, and wherein the lower band is a continuous solid band except for a point of discontinuity around its periphery between adjacent abutting ends of the solid band, the adjacent abutting ends being only separated by a perforated junction defining the point of discontinuity that permits expansion of the support stent from the first diameter to a second diameter larger than the first diameter upon application of an outward dilatory force from within the support stent substantially larger than forces associated with normal physiological use but prevents contraction of the lower band; and a plurality of flexible leaflets supported by the stent and configured to ensure one-way blood flow therethrough.

2. The prosthetic heart valve of claim 1, wherein the perforated junction is configured to break upon application of an outward dilatory force from within the support stent of at least 1 atmosphere.

3. The prosthetic heart valve of claim 1, wherein the perforated junction is configured to resist breaking until application of an outward dilatory force from within the support stent of up to 12 atmospheres.

4. The prosthetic heart valve of claim 1, wherein each commissure post has a gap between two sides and the lower band extends across the gaps in two wall segments, wherein the point of discontinuity is located where the wall segments come together defining the adjacent abutting ends.

5. The prosthetic heart valve of claim 1, wherein there is a single point of discontinuity located below only one of the commissure posts.

6. The prosthetic heart valve of claim 1, wherein there is a point of discontinuity located below each of the commissure posts.

7. The prosthetic heart valve of claim 1, further including a unique identifier on the support stent visible from outside the body after implant that identifies the support stent as being expandable, and the unique identifier is a numerical valve size in odd 2-millimeter increments between 15-33 mm.

8. The prosthetic heart valve of claim 1, wherein the one-piece inner structural support stent is made of titanium.

9. The prosthetic heart valve of claim 8, wherein each commissure post has a gap between two sides and the lower band extends across the gaps in two wall segments, wherein the point of discontinuity is located where the wall segments come together defining the adjacent abutting ends.

10. The prosthetic heart valve of claim 1, wherein the one-piece inner structural support stent is made of an acetal copolymer.

11. The prosthetic heart valve of claim 10, wherein each commissure post has a gap between two sides and the lower band extends across the gaps in two wall segments, wherein the point of discontinuity is located where the wall segments come together defining the adjacent abutting ends.

12. A prosthetic heart valve adapted for post-implant expansion and having an inflow end and an outflow end, comprising:

a one-piece inner structural support stent including a generally circular solid lower band having three upstanding commissure posts, the stent defining an implant circumference that is substantially non-compressible in normal physiological use and has a first diameter, and wherein the lower band is a continuous solid band except for a point of discontinuity around its periphery between adjacent ends of the solid band, the adjacent ends being only connected by mutually interlaced tabs defining the point of discontinuity, the interlaced tabs maintaining alignment and circularity of the solid band while being arranged to slide away from one another and permit expansion of the support stent from the first diameter to a second diameter larger than the first diameter upon application of an outward dilatory force from within the support stent substantially larger than forces associated with normal physiological use but preventing contraction of the lower band less than the first diameter; and a plurality of flexible leaflets supported by the stent and configured to ensure one-way blood flow therethrough.

13. The prosthetic heart valve of claim 12, wherein each commissure post has a gap between two sides and the lower band extends across the gaps in two wall segments, wherein the point of discontinuity is located where the wall segments come together defining the adjacent ends.

14. The prosthetic heart valve of claim 12, wherein there is a single point of discontinuity located below only one of the commissure posts.

15. The prosthetic heart valve of claim 12, wherein there is a point of discontinuity located below each of the commissure posts.

16. The prosthetic heart valve of claim 12, further including a unique identifier on the support stent visible from outside the body after implant that identifies the support stent as being expandable, and the unique identifier is a numerical valve size in odd 2-millimeter increments between 15-33 mm.

17. The prosthetic heart valve of claim 12, wherein the one-piece inner structural support stent is made of titanium.

18. The prosthetic heart valve of claim 17, wherein each commissure post has a gap between two sides and the lower band extends across the gaps in two wall segments, wherein the point of discontinuity is located where the wall segments come together defining the adjacent ends.

19. The prosthetic heart valve of claim 12, wherein the one-piece inner structural support stent is made of an acetal copolymer.

20. The prosthetic heart valve of claim 19, wherein each commissure post has a gap between two sides and the lower band extends across the gaps in two wall segments, wherein the point of discontinuity is located where the wall segments come together defining the adjacent ends.

\* \* \* \* \*